(12) United States Patent
Doerner et al.

(10) Patent No.: US 11,235,063 B2
(45) Date of Patent: Feb. 1, 2022

(54) BI-SPECIFIC ANTIBODIES FOR ENHANCED TUMOR SELECTIVITY AND INHIBITION AND USES THEREOF

(71) Applicant: MERCK PATENT GMBH, Darmstadt (DE)

(72) Inventors: Achim Doerner, Darmstadt (DE); Lars Toleikis, Kleinniedesheim (DE); Vanita D. Sood, Somerville, MA (US); Carolin Sellmann, Darmstadt (DE); Christine Knuehl, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 680 days.

(21) Appl. No.: 15/773,555

(22) PCT Filed: Oct. 27, 2016

(86) PCT No.: PCT/EP2016/001791
§ 371 (c)(1),
(2) Date: May 3, 2018

(87) PCT Pub. No.: WO2017/076492
PCT Pub. Date: May 11, 2017

(65) Prior Publication Data
US 2018/0326085 A1    Nov. 15, 2018

(30) Foreign Application Priority Data

Nov. 3, 2015 (EP) ..................... 15192851
Jul. 5, 2016 (EP) ..................... 16178010

(51) Int. Cl.
| C07K 16/00 | (2006.01) |
| A61K 47/68 | (2017.01) |
| C07K 16/28 | (2006.01) |
| A61P 35/00 | (2006.01) |

(52) U.S. Cl.
CPC .......... *A61K 47/6803* (2017.08); *A61K 47/68* (2017.08); *A61K 47/6849* (2017.08); *A61K 47/6879* (2017.08); *A61P 35/00* (2018.01); *C07K 16/2863* (2013.01); *C07K 2317/24* (2013.01); *C07K 2317/31* (2013.01); *C07K 2317/52* (2013.01); *C07K 2317/526* (2013.01); *C07K 2317/54* (2013.01); *C07K 2317/56* (2013.01); *C07K 2317/569* (2013.01); *C07K 2317/622* (2013.01); *C07K 2317/64* (2013.01); *C07K 2317/732* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 4,444,887 A | 4/1984 | Hoffman |
| 4,716,111 A | 12/1987 | Osband et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,814,318 A | 9/1998 | Lonberg et al. |
| 5,892,019 A | 4/1999 | Schlom et al. |
| 9,505,848 B2 * | 11/2016 | Davis ............... C07K 16/00 |

FOREIGN PATENT DOCUMENTS

| EP | 0 239 400 | 9/1987 |
| EP | 0 519 596 | 12/1992 |
| EP | 0 592 106 | 4/1994 |
| EP | 2 832 748 | 2/2015 |
| WO | 1991/009967 | 7/1991 |
| WO | 1991/010741 | 7/1991 |
| WO | 1992/022653 | 12/1992 |
| WO | 1996/033735 | 10/1996 |
| WO | 1996/034096 | 10/1996 |
| WO | 1998/016654 | 4/1998 |
| WO | 1998/024893 | 6/1998 |
| WO | 1998/046645 | 10/1998 |

(Continued)

OTHER PUBLICATIONS

Almagro & Fransson, Frontiers in Bioscience 2008; 13:1619-33 (Year: 2008).*
Castoldi et al. (Oncogene, 32, pp. 5593-5601, 2013). (Year: 2013).*
Lifely et al., "Glycosylation and biological activity of CAMPATH-1H expressed in different cell lines and grown under different culture conditions," 1995, Glycobiology, vol. 5, Iss. 8, pp. 813-822.
Albrecht et al., "Production of Soluble ScFvs with C-Terminal-Free Thiol for Site-Specific Conjugation or Stable Dimeric ScFvs on Demand," 2004, Bioconjugate Chem., 15, pp. 16-26.
Alivisatos AP, "Perspectives on the Physical Chemistry of Semiconductor Nanocrystals," 1996, J. Phys. Chem., 100, pp. 13226-13239.

(Continued)

*Primary Examiner* — Meera Natarajan
(74) *Attorney, Agent, or Firm* — Grüneberg and Myers PLLC

(57) ABSTRACT

A heterodimeric bispecific immunoglobulin molecule includes a first Fab or scFv fragment which specifically binds to EGFR, and a second Fab or scFv fragment which specifically binds to c-MET, and an antibody hinge region, an antibody CH2 domain and an antibody CH3 domain including a hybrid protein-protein interaction interface domain. Each of the interaction interface domains is formed by an amino acid segment of the CH3 domain of a first member and an amino acid segment of the CH3 domain of a second member. The hybrid protein-protein interface domain of the first chain is interacting with the protein-protein-interface of the second chain by homodimerization of a corresponding amino acid segment of the same member of the immunoglobulin superfamily within interaction domains.

28 Claims, 26 Drawing Sheets

Specification includes a Sequence Listing.

(56) References Cited

FOREIGN PATENT DOCUMENTS

| WO | 1998/050433 | 11/1998 |
|---|---|---|
| WO | 2007/062037 | 5/2007 |
| WO | 2007/110205 | 10/2007 |
| WO | 2009/032661 | 3/2009 |
| WO | 2010/115551 | 10/2010 |
| WO | 2010/138719 | 12/2010 |
| WO | 2014/001325 | 1/2014 |
| WO | 2014/081954 | 5/2014 |
| WO | 2014/093379 | 6/2014 |
| WO | 2014/150973 | 9/2014 |

OTHER PUBLICATIONS

Alivisatos AP, "Semiconductor Clusters, Nanocrystals, and Quantum Dots," 1996, Science, 271, pp. 933-937.

Andrew et al., "Fragmentation of Immunoglobulin G," 2000, Current Protocols in Cell Biology, pp. 16.4.1-16.4.10.

Bardelli et al., "Molecular Mechanisms of Resistance to Cetuximab and Panitumumab in Colorectal Cancer," 2010, Journal of Clinical Oncology, 28(7); pp. 1254-1261.

Bird et al., "Single-chain Antigen-Binding Proteins," 1988, Science, 242, pp. 423-427.

Bobrovnik SA, "Determination of antibody affinity," 2003, Journal of Biochemical and Biophysical Methods, 57, pp. 213-236.

Cipriani et al., "MET as a target for treatment of chest tumours," 2009, Lung Cancer; 63(2), pp. 169-179.

Clynes et al., "Inhibitory Fc receptors modulate in vivo cytoxicity against tumor targets," 2000, Nature Medicine, 6(4), pp. 443-446.

Elgersma et al., "Design, Synthesis, and Evaluation of Linker-Duocarmycin Payloads: Toward Selection of HER2-Targeting Antibody-Drug Conjugate SYD985," 2015, Mol. Pharmaceutics, 12, pp. 1813-1835.

Engelman et al., "MET Amplification Leads to Gefitinib Resistance in Lung Cancer by Activating ERBB3 Signaling," 2007, Science, 316, pp. 1039-1044.

Glaser et al., "Novel Antibody Hinge Regions for Efficient Production of CH2 Domain-deleted Antibodies*," 2005, Journal of Biological Chemistry, 280(50), pp. 41494-41503.

Hamblett et al., "Effects of Drug Loading on the Antitumor Activity of Monoclonal Antibody Drug Conjugate," 2004, Clinical Cancer Research, 10, pp. 7063-7070.

Hamers-Casterman et al., "Naturally occurring antibodies devoid of light chains," 1993, Nature, 363, pp. 446-448.

Ho et al., "Site-directed mutagenesis by overlap extension using the polymerase chain reaction," 1989, Gene, 77, pp. 51-99.

Jefferis et al., "IgG—Fc-mediated effector functions: molecular definition of interaction sites for effector ligands and the role of glycosylation," 1998, Immunoligical Reviews, 163, pp. 59-76.

King et al.; "Applications and Engineering of Monoclonal Antibodies," 1998, Applications and Engineering of Monoclonal Antibodies, CRC Press, Cp. 2.4.1, pp. 39-50.

Kornberger et al., "Sortase-catalyzed in vitro functionalization of a HER2-specific recombinant Fab for tumor targeting of the plant cytotoxin gelonin," 2014, mAbs, 6(2), pp. 354-366.

Krinner et al., "A highly stable polyethylene glycol-conjugated human single-chain antibody neutralizing granulocyte-macrophage colony stimulating factor at low nanomolar concentration," 2006, Protein Engineering, Design, & Selection, 19(10), pp. 461-470.

Mansur et al., "Biomolecule-quantum dot systems for bioconjugation applications," 2011, Colloids and Surfaces B: Biointerfaces, 84, pp. 360-368.

Marty et al., "Production of Functionalized Single-Chain Fv Antibody Fragments Binding to the ED-B Domain of the B-isoform of Fibronectin in Pichia pastoris," 2001, Protein Expression and Purification, 21, pp. 156-164.

Milenic et al., "Construction, Binding Properties, Metabolism, and Tumor Targeting of a Single-Chain Fv Derived from the Pancarcinoma Monoclonal Antibody CC49," 1991, Cancer Research, 51, pp. 6363-6371.

Murphy et al., "Using Biacore to Measure the Binding Kinetics of an Antibody-Antigen interaction," 2006, Current Protocols in Protein Science, pp. 19.14.1-19.14.17.

Natarajan et al., "Characterization of Site-Specific ScFv PEGylation for Tumor-Targeting Pharmaceuticals" 2005, Bioconjugate Chem., 16, pp. 113-121.

Neuber et al., "Characterization and screening og IgG binding to the neonatal Fc receptor," 2014, mAbs, 6(4), pp. 928-942.

Padlan EA, "A Possible Procedure for Reducing the Immunogenicity of Antibody Possible Procedure for Reducing the Immunogenicity of Antibody Variable Domains While Preserving Their Ligand Binding Properties," 1991, Molecular Immunology, 28(4/5), pp. 489-498.

Pantoliano et al., "Conformational Stability, Folding, and Ligand-Binding Affinity of Single-Chain Fv Immunoglobulin Fragments Expressed in *Escherichia coli*," 1991, Biochemistry, 30, pp. 10117-10125.

Perez et al., "Antibody-drug conjugates: current status and future directions," 2014, Drug Discovery Today, 19(7), pp. 869-881.

Popp et al., "Making and Breaking Peptide Bonds: Protein Engineering Using Sortase," Angew. Chem. Int. Ed., 50, pp. 5024-5032.

Roguska et al., "Humanization of murine monoclonal antibodies through variable domain resurfacing," 1994 Proc. Nat. Acad. Sci., 91, pp. 969-973.

Roopenian et al., "FcRn: the neonatal Fc receptor comes of age," 2007, Nature Reviews Immunolog, 7, pp. 715-725.

Schmidt et al., "Germline and somatic mutations in the tyrosine kinase domain of the MET proto-oncogene in papillary renal carcinomas," 1997, Nature Genetics, 16(1), pp. 68-73.

Shields et al., "High Resolution Mapping of the Binding Site on Human IgG1 for FcγRI, FcγRII, FcγRIII, and FcRn and Design of IgG1 Variants with improved Binding to the FcγR*," 2001, J. Bio. Chem., 276(9), pp. 6591-6604.

Song et al., "Principles of conjugating quantum dots to proteins via carbodiimide chemistry," 2011, Nanotechnology, 22, pp. 494066-494012.

Studnicka et al., "Human-engineered monoclonal antibodies retain full specific binding activity by preserving non-CDR complementarity-modulating residues," 1994 Proc. Natl. Acad. Sci, 91, pp. 969-973.

Takaoka et al., "Protein Organic Chemistry and Applications for Labeling and Engineering in Live-Cell Systems," 2013, Angew. Chem. Int. Ed., 52, pp. 4088-4106.

Takkienen et al.,"An active single-chain antibody containing a cellulase linker domain is secreted by *Escherichia coli*," 1991, Protein Engineering, 4(7), pp. 837-841.

Castoldi et al.; "A novel bispecific EGFR/Met antibody blocks tumor-promoting phenotypic effects inducted by resistance to EGFR inhibition and has potent antitumor activity," Oncogene, vol. 32, No. 50, Jul. 1, 2013, pp. 5593-5601.

Jarantow et al., "Impact of Cell-surface Antigen Expression on Target Engagement and Function of an Epidermal Growth Factor Receptor x c-MET Bispecific Antibody," Journal of Biological Chemistry, vol. 290, No. 41, Aug. 10, 2015, pp. 24689-24704.

Moores et al. "Abstract B241: Bispecific antibody targeting EGFR and cMet demonstrates superior activity compared to the combination of single pathway inhibitors," Molecular Cancer Therapuetics, vol. 12, No. 11, Nov. 1, 2013, p. B241.

Wu et al., "Fab-based bispecific antibody formats with robust biophysical properties and biological activity," MABS, Landes Bioscience, US, vol. 3, Jan. 1, 2015, pp. 470-482.

Krumbach et al., "Primary resistance to cetuximab in a panel of patient-derived tumour xenograft models: Activation of MET as one mechanism for drug resistance," European Journal of Cancer, vol. 47, No. 8, May 1, 2011, pp. 1231-1243.

Sattler et al., "The role of the c-Met pathway in lung cancer and the potential for targeted therapy," Therapeutic Advances in Medical Oncology, vol. 3, No. 4, Jul. 1, 2011, pp. 171-184.

International Search Report mailed in PCT/EP2016/001791 and dated Nov. 5, 2017.

Written Opinion of the International Searching Authority mailed in PCT/EP2016/001791 and dated Nov. 5, 2017.

Terskikh et al., ""Peptabody": A new type of high avidity binding protein," 1997, Proc. Natl. Acad. Sci., 94, pp. 1663-1668.

(56) References Cited

OTHER PUBLICATIONS

Weller, "Colloidal Semiconductor Q-Particles: Chemistry in the Transition Region Between Solid State and Molecules," 1993, Angew Chem Int Ed Engl, 32, pp. 41-53.
Wright et al., "Effect of glycosylation on antibody function: implications for genetic engineering," 1997, Trends Biotechnol, 15, pp. 26-32.
Zhao et al., "Two routes for production and purification of Fab fragments in biopharmaceutical discovery research: Papain digestion of mAb and transient expression in mammalian cells," 2009, Protein Expression and Purification, 67, pp. 182-189.

* cited by examiner

A
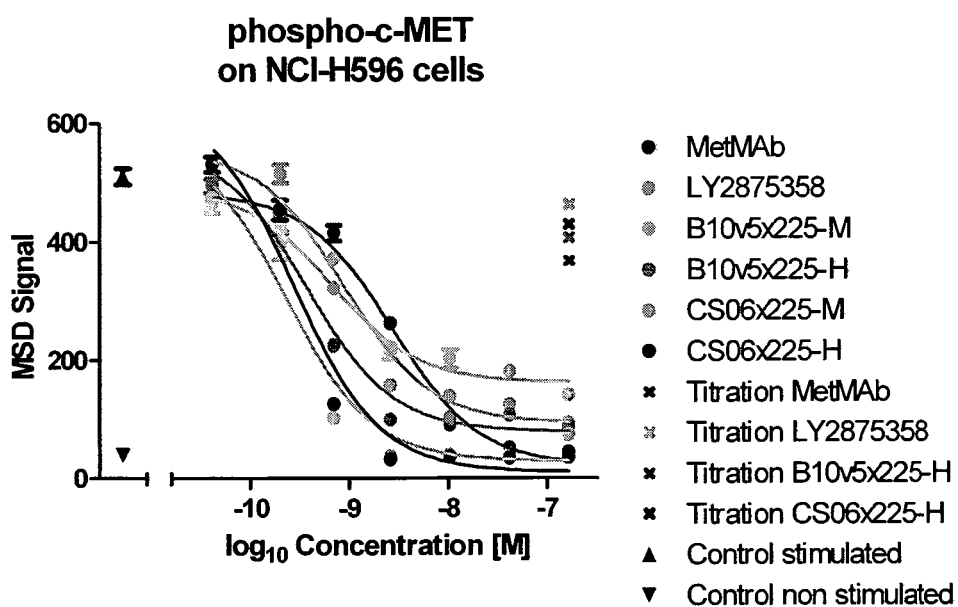
B
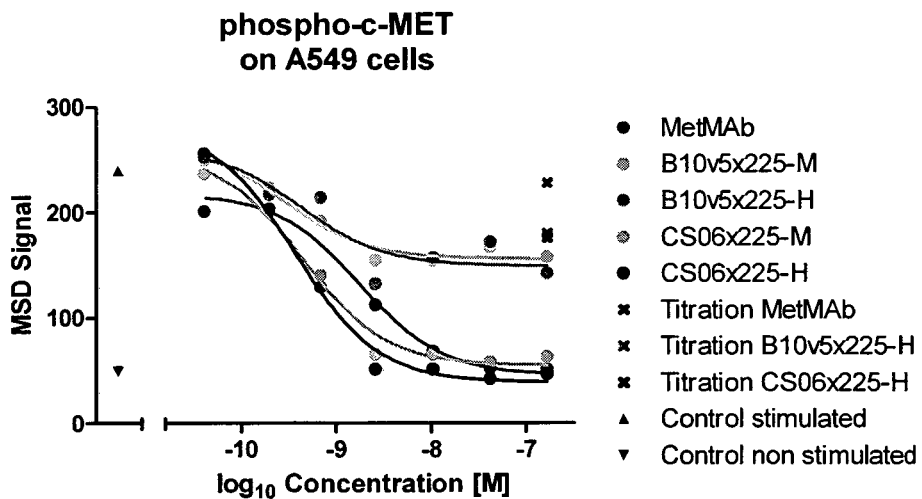
FIGURE 6

A

| Antibody | Potency IC$_{50}$ [M] | Efficacy % Effect |
|---|---|---|
| MetMAb | NANOMOLAR | 100% |
| LY2875358 | | 90% |
| B10v5x225-M | | 80% |
| B10v5x225-H | | 90% |
| CS06x225-M | SUBNANOMOLAR | 93% |
| CS06x225-H | | 100% |

B

| Antibody | Potency IC$_{50}$ [M] | Efficacy % Effect |
|---|---|---|
| MetMAb | NANOMOLAR | 100% |
| B10v5x225-M | SUBNANOMOLAR | 43% |
| B10v5x225-H | | 52% |
| CS06x225-M | SUBNANOMOLAR | 93% |
| CS06x225-H | | 100% |

FIGURE 7

A
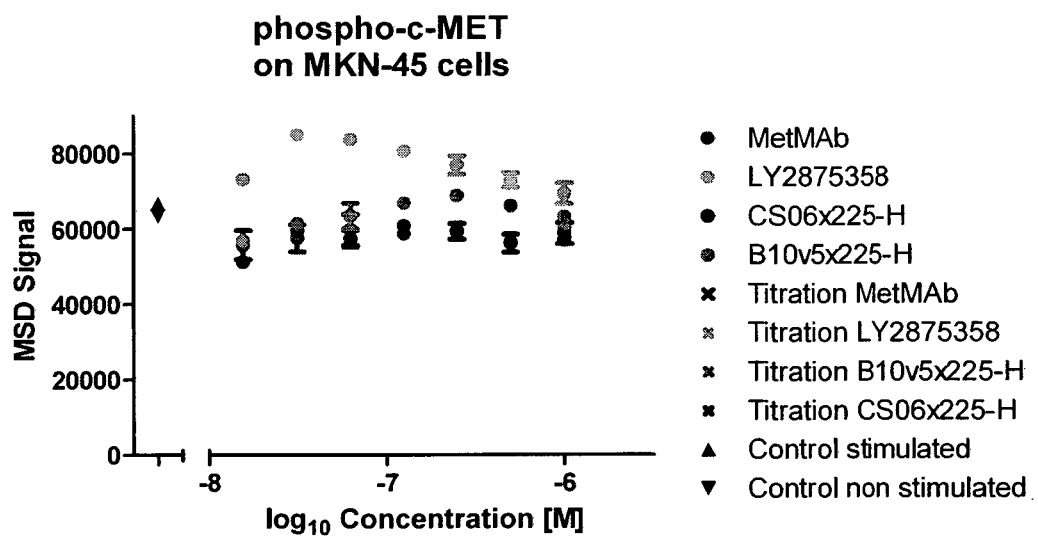
B
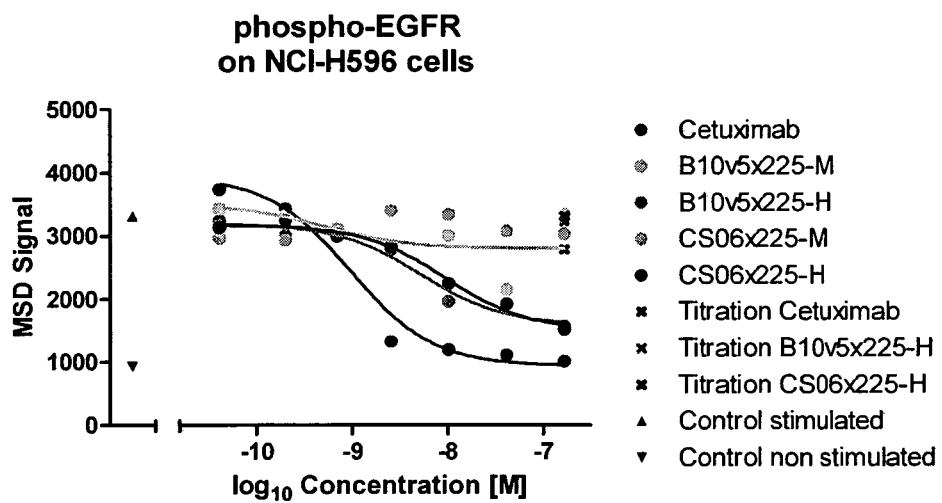
FIGURE 8

A
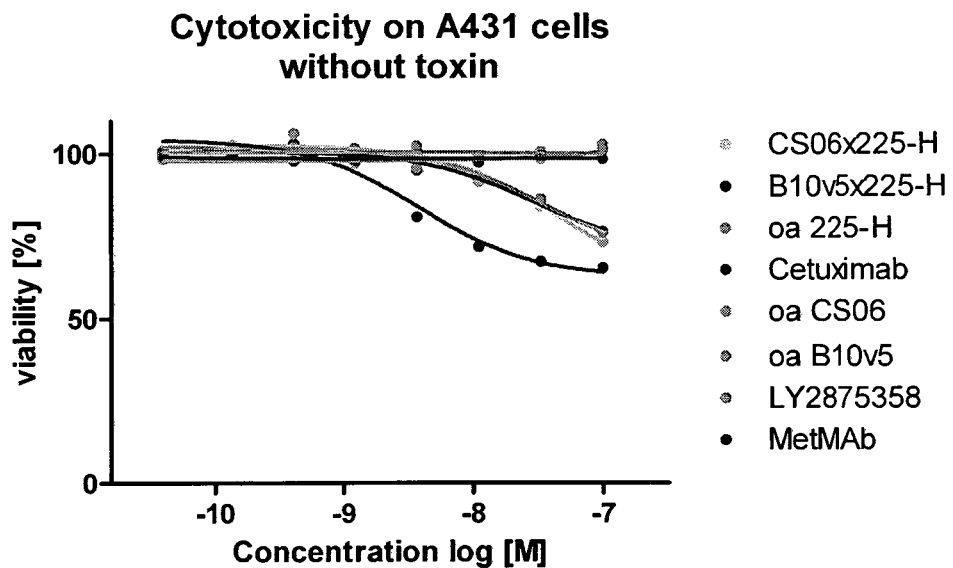
B
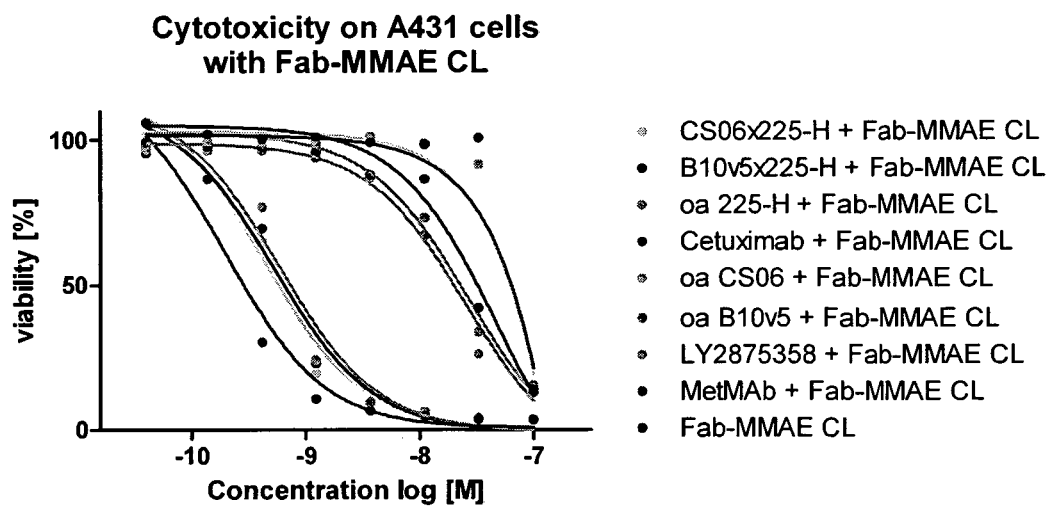
FIGURE 9

A
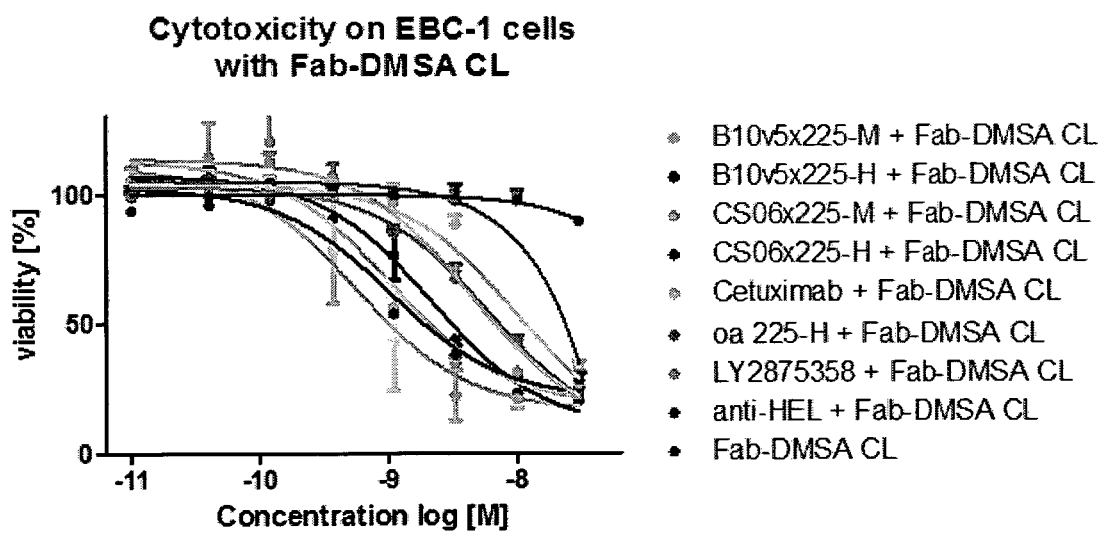
B
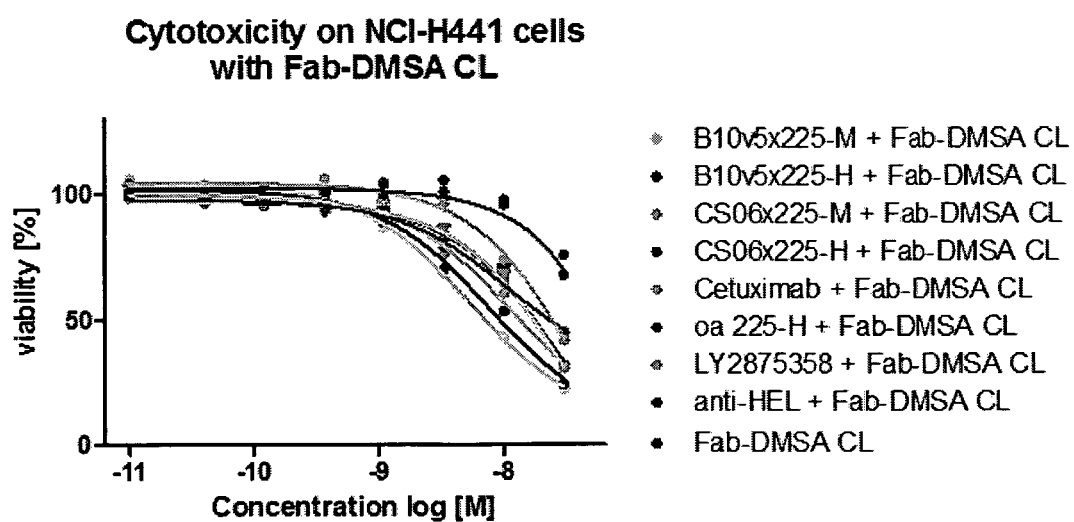
FIGURE 10

A
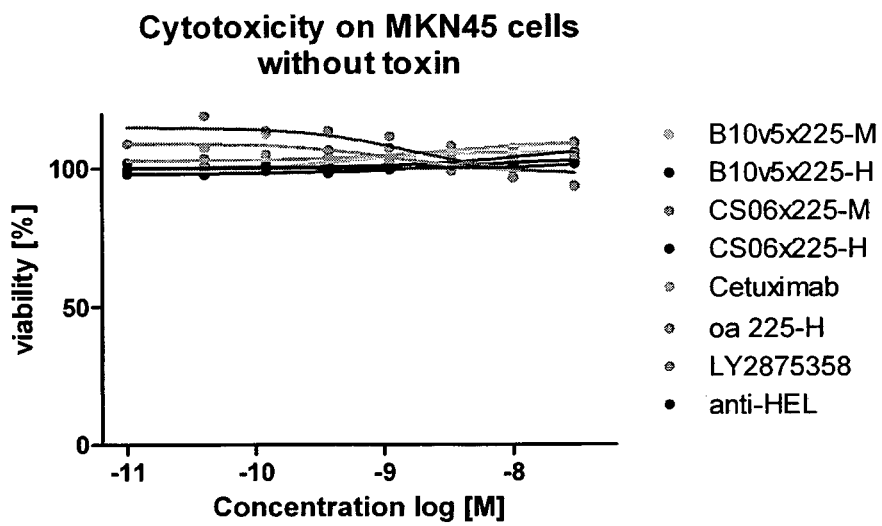
B
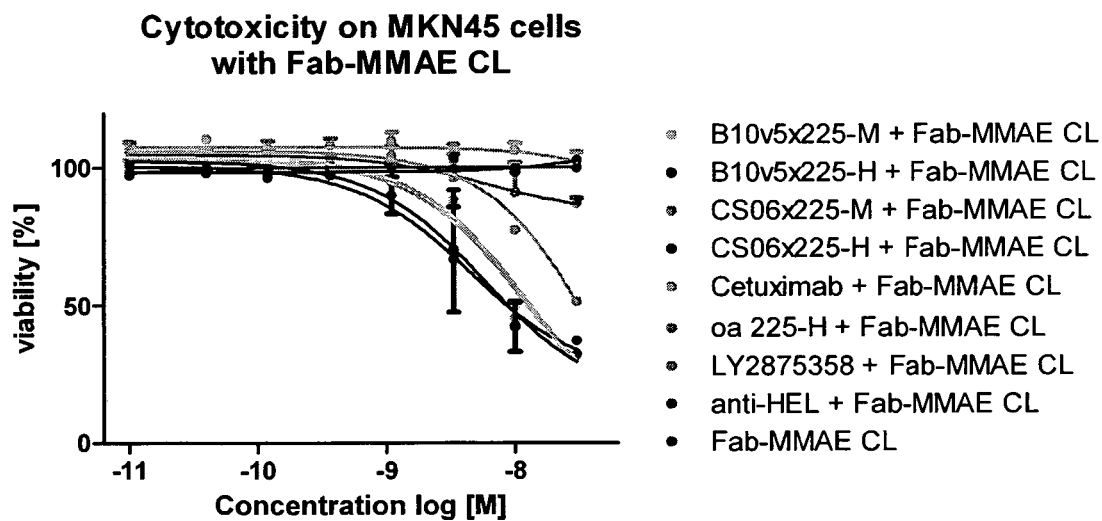
FIGURE 11

A
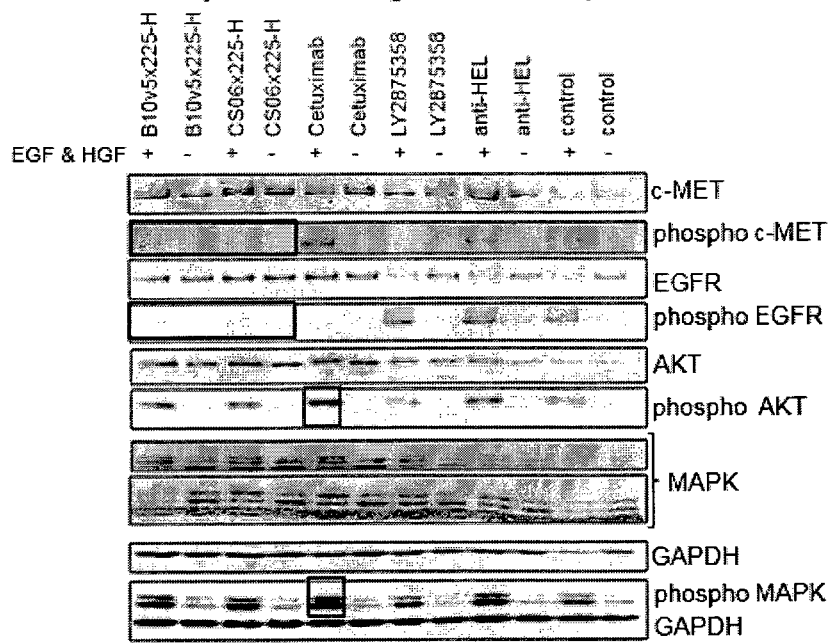
B
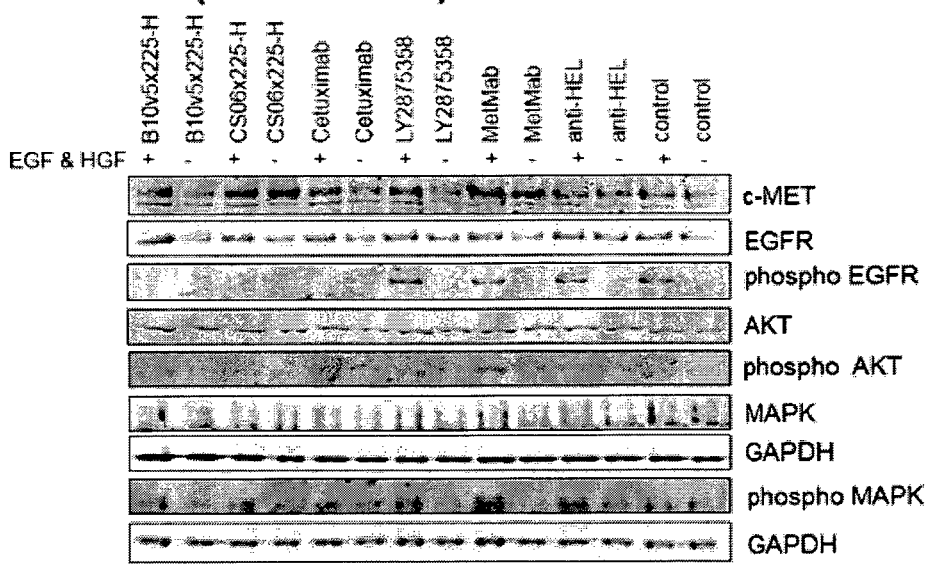
FIGURE 12

| | Cellular Binding - Flow Cytometry ( MFI at 100 nM) | | | | | | |
|---|---|---|---|---|---|---|---|
| Construct name | EBC-1 c-MET+++ EGFR++ | A431 c-MET+ EGFR+++ | MKN-45 c-MET+++ EGFR++ | A549 c-MET+ EGFR++ | SK-MEL2 c-MET+ EGFR- | HepG2 c-MET+ EGFR+ | CHO-S c-MET- EGFR- |
| B10x225-L | 434 | 947 | 1221 | 192 | 23 | 85 | 17 |
| B10x225-M | 671 | 1476 | 1787 | 572 | 53 | 84 | 36 |
| B10x225-H | 948 | 1980 | 1318 | 454 | 64 | 100 | 46 |
| B10x425 | 361 | 1123 | 1265 | 270 | 25 | 101 | 19 |
| F06x225-L | 801 | 1198 | 1173 | 215 | 68 | 98 | 29 |
| F06x225-M | 793 | 1899 | 1221 | 303 | 58 | 74 | 15 |
| F06x225-H | 793 | 3242 | 1195 | 303 | 56 | 87 | 15 |
| F06x425 | 656 | 1266 | 1161 | 265 | 67 | 76 | 23 |
| B10v5x225-L | 2041 | 847 | 1217 | 249 | 341 | 451 | 129 |
| B10v5x225-M | 2284 | 1291 | 1268 | 383 | 457 | 793 | 276 |
| B10v5x225-H | 2060 | 1762 | 1330 | 335 | 222 | 352 | 94 |
| B10v5x425 | 1962 | 1428 | 1280 | 328 | 213 | 348 | 108 |
| CS06x225-L | 2048 | 890 | 1531 | 212 | 188 | 254 | 17 |
| CS06x225-M | 1871 | 1174 | 1470 | 264 | 236 | 330 | 41 |
| CS06x225-H | 1558 | 1855 | 1553 | 292 | 164 | 198 | 14 |
| CS06x425 | 1371 | 1351 | 1454 | 268 | 132 | 164 | 12 |
| oa 225-L | 137 | 1256 | 83 | 91 | 17 | 22 | 14 |
| oa225-M | 189 | 1498 | 144 | 138 | 19 | 40 | 25 |
| oa 225-H | 287 | 2230 | 199 | 184 | 20 | 53 | 15 |
| oa 425 | 212 | 1150 | 184 | 170 | 17 | 50 | 15 |
| oa F06 | 667 | 40 | 1276 | 91 | 32 | 28 | 13 |
| oa B10 | 952 | 103 | 916 | 130 | 39 | 69 | 47 |
| oa CS06 | 2627 | 37 | 1490 | 147 | 213 | 296 | 11 |
| oa B10v5 | 2312 | 49 | 1503 | 91 | 272 | 399 | 88 |

"oa": one-armed heterodimeric immunoglobulin molecule

Cellular binding assays of the indicated immunoglobulin molecules to cells expressing different levels of EGFR and/or c-MET with +++ indicating high expression levels, ++ moderate expression levels, + low expression levels. The numbers provided indicate mean fluorescent intensities as determined by flow-cytometry at an immunoglobulin molecule concentration of 100nM.

FIGURE 15

| Mutation | $K_D$[a] | $\Delta\Delta G_{exp}$[b] | $\Delta\Delta G_{calc}$[c] | $\Delta\Delta E_{pair}$[d] | $\Delta\Delta E_{Hbnd}$[e] | $E_{Hbnd\_sc}$[f] | $\Delta\Delta G_{Ab}$[g] |
|---|---|---|---|---|---|---|---|
| WT | 1.52 ± 0.29 | 0 | 0 | 0 | 0 | 0 | 0 |
| C225-L | NQ | | -0.7 | -0.4 | -0.4 | -1.1 | 1.6 |
| C225-M | 15.26 | 1.36 | -0.7 | 0.1 | -0.8 | -1.1 | 6.3 |
| C225-H1 | 0.77 ± 0.09 | -0.41 | -2.0 | -1.1 | -1.2 | -2.2 | -0.7 |
| C225-H2 | 1.09 ± 0.13 | -0.20 | -0.2 | -0.1 | -0.7 | -1.1 | 3.1 |
| C225-H3 | 0.37 ± 0.04 | -0.84 | -0.9 | -0.6 | -0.2 | -0.2 | 0.4 |
| C225-H | 0.08 ± 0.03 | -1.75 | -3.2 | | | | -6.3 |

FIGURE 16

| Antibody | Analyte | $K_D$ [M] | $k_a$ [M$^{-1}$s$^{-1}$] | $k_d$ [s$^{-1}$] | $T_m$ [°C] |
|---|---|---|---|---|---|
| oa B10 | c-MET | 1.2E-08 | 1.0 E+05 | 1.2E-03 | 65.7 ± 0.001 |
| oa B10v5 | c-MET | 3.8E-10 | 4.0 E+05 | 1.6E-04 | 64.0 ± 0.172 |
| B10v5xhu225-M | c-MET | 3.7E-10 | 4.0 E+05 | 1.5E-04 | 64.5 ± 0.001 |
| B10v5xhu225-H | c-MET | 3.6E-10 | 4.0 E+05 | 1.5E-04 | 62.8 ± 0.174 |
| oa F06 | c-MET | 4.2E-09 | 2.5E+06 | 1.1E-02 | 64.8 ± 0.172 |
| oa CS06 | c-MET | 1.9E-10 | 1.1E+06 | 2.1E-04 | 64.9 ± 0.001 |
| CS06xhu225-M | c-MET | 2.1E-10 | 1.1E+06 | 2.2E-04 | 64.8 ± 0.126 |
| CS06xhu225-H | c-MET | 1.2E-10 | 3.3E+06 | 3.9E-04 | 62.2 ± 0.172 |
| oa hu225-L | EGFR | 2.2E-07 | 6.1E+05 | 1.4E-01 | n.d. |
| oa hu225-M | EGFR | 4.4E-09 | 3.7E+06 | 1.6E-02 | 65.2 ± 0.174 |
| B10v5xhu225-M | EGFR | 4.7E-09 | 3.6E+06 | 1.7E-02 | 64.5 ± 0.001 |
| CS06xhu225-M | EGFR | 3.9E-09 | 4.6E+06 | 1.8E-02 | 64.8 ± 0.126 |
| oa hu225-H | EGFR | 1.4E-10 | 3.6E+06 | 4.9E-04 | 62.7 ± 0.001 |
| B10v5xhu225-H | EGFR | 1.5E-10 | 3.5E+06 | 5.3E-04 | 62.8 ± 0.174 |
| CS06xhu225-H | EGFR | 1.2E-10 | 3.3E+06 | 3.9E-04 | 62.2 ± 0.172 |
| cetuximab (C225) | EGFR | 1.2E-09 | 6.1E+05 | 7.4E-04 | 67.3 ± 0.172 |
| oa hu425 | EGFR | 2.2E-08 | 5.3E+05 | 1.2E-02 | n.d. |
| matuzumab (425) | EGFR | 1.2E-08 | 6.4E+05 | 7.8E-03 | n.d. |

FIGURE 17

| Cell line | Origin | c-MET density [x $10^3$ ± s.d %] | EGFR density [x $10^3$ ± s.d %] |
|---|---|---|---|
| A431 | epidermoid CA | 14.7 ± 0.2 | 661.0 ± 1.4 |
| A549 | lung ACA | 18.0 ± 0.6 | 39.3 ± 0.6 |
| EBC-1 | lung SCC | 261.6 ± 1.1 | 62.2 ± 1.1 |
| HepG2 | hepatocellular CA | 11.1 ± 1.4 | 1.3 ± 4.7 |
| KP-4 | pancreatic CA | 7.7 ± 0.5 | 50.8 ± 0.9 |
| MDA-MB-468 | breast ACA | 14.2 ± 1.0 | 1825.5 ± 0.1 |
| MKN-45 | gastric ACA | 171.7 ± 1.0 | 45.4 ± 0.3 |
| NCI-H1975 | lung ACA | 35.5 ± 0.7 | 37.8 ± 0.7 |
| NCI-H441 | lung ACA | 52.2 ± 0.8 | 46.6 ± 3.7 |
| NCI-H596 | lung ACA | 6.7 ± 1.0 | 148.5 ± 1.4 |
| NHEK.f-c. | keratinocytes | 7.1 ± 8.9 | 128.7 ± 8.7 |
| T47D | breast ACA | 0.0 | 13.2 ± 0.9 |

FIGURE 18

| Antibody | Receptor | A549 | | NHEK.f-c. | |
|---|---|---|---|---|---|
| | | $IC_{50}$ [nM] ± s.d. | n | $IC_{50}$ [nM] ± s.d. | n |
| CS06x225-H | phospho-c-MET | 0.3 ± 0.2 | 4 | 0.1 | 1 |
| | phospho-EGFR | 0.8 | 1 | 0.8 | 1 |
| B10v5x225-H | phospho-c-MET | 0.3 ± 0.2 | 2 | 0.2 | 1 |
| | phospho-EGFR | 1.1 ± 0.4 | 2 | 1.7 ± 0.3 | 2 |
| oa 5D5 | phospho-c-MET | 0.8 ± 0.5 | 4 | 0.7 | 1 |
| cetuximab | phospho-EGFR | 0.4 ± 0.1 | 3 | 0.3 ± 0.2 | 2 |

FIGURE 19

| Antibody | A431 | | | | NHEK.f-c. | | | | therapeutic window | |
|---|---|---|---|---|---|---|---|---|---|---|
| | $EC_{50}$ [nM] | $ED_{80}$ [nM] | % cell killing at 50 nM | n | $IC_{50}$ [nM] | $TD_{20}$ [nM] | % cell killing at 50 nM | n | $IC_{50}$-$EC_{50}$ [nM] | $TD_{20}$/$ED_{80}$ |
| B10v5x225-H-vc-MMAE | 0.4 ± 0.1 | 2.1 ± 0.7 | 93 ± 1.3 | 5 | 5.9 ± 2.9 | 3.7 ± 1.1 | 37 ± 12 | 5 | 5.6 | 2 |
| B10v5x225-M-vc-MMAE | 1.0 ± 0.3 | 5.0 ± 1.5 | 91 ± 0.4 | 3 | 19 ± 7* | 25 ± 8 | 30 ± 9 | 3 | 28.1* | 6 |
| B10x225-M-vc-MMAE | 0.7 ± 0.2 | 3.6 ± 0.9 | 90 ± 0.5 | 3 | 20 ± 10* | 19 ± 8 | 27 ± 11 | 3 | 18.8* | 5 |
| cetuximab-vc-MMAE | 0.1 ± 0.04 | 0.7 ± 0.3 | 92 ± 1.4 | 5 | 1.0 ± 0.5 | 0.8 ± 0.5 | 34 ± 10 | 5 | 0.9 | 1 |

FIGURE 23

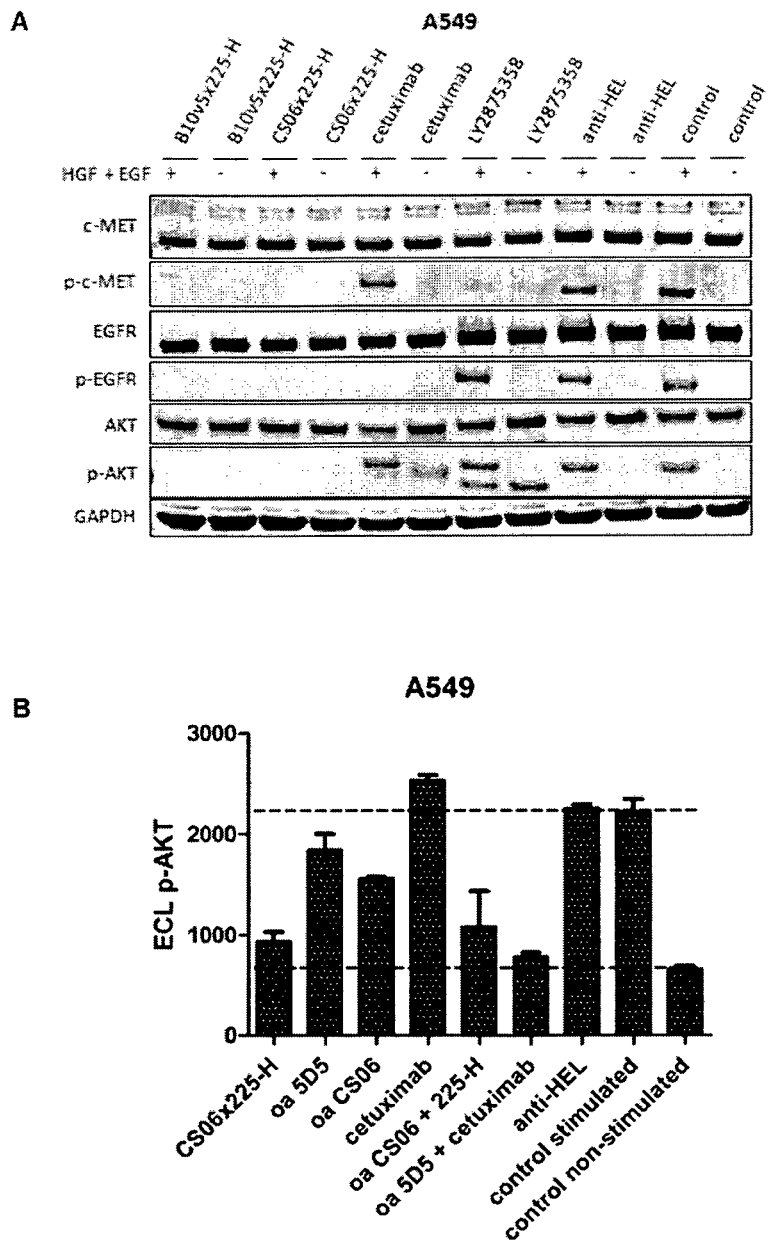
FIGURE 25 A, B

C
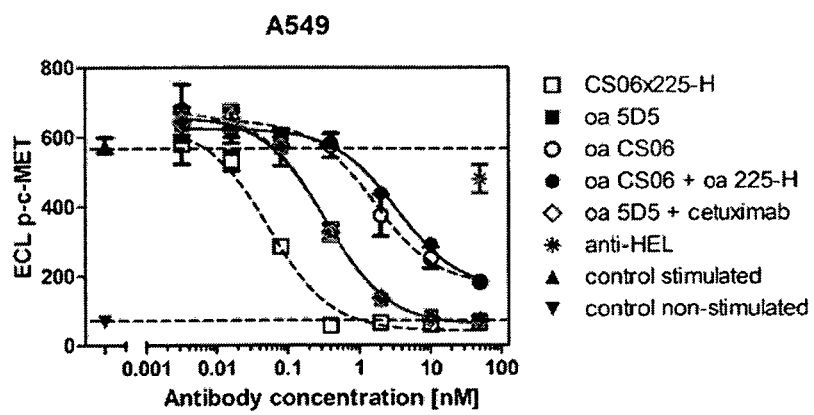
D
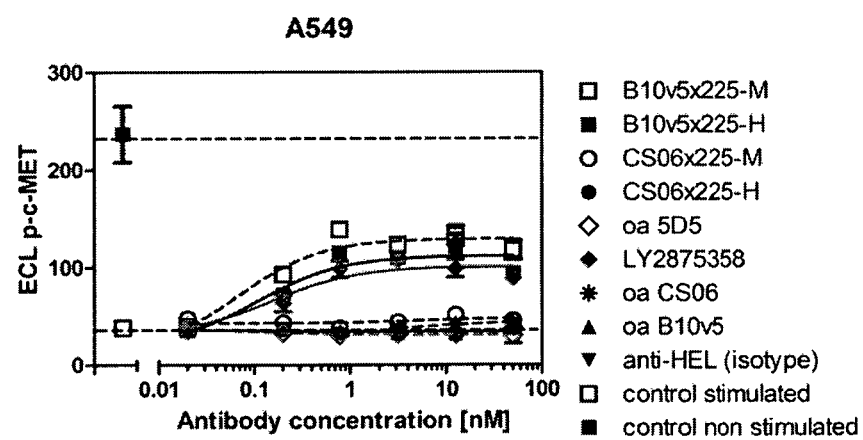
FIGURE 25 C, D

SEQUENCE LISTING

```
<160> NUMBER OF SEQ ID NOS: 54

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu225 VL kinetic variants
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 1

Gly Gln Pro Phe Arg Pro Glu Val His Leu Leu Pro Pro Ser Arg Glu
1               5                   10                  15

Glu Met Thr Lys Asn Gln Val Ser Leu Thr Cys Leu Ala Arg Gly Phe
            20                  25                  30

Tyr Pro Xaa Asp Ile Ala Val Glu Trp Glu Ser Asn Gly Gln Pro Glu
        35                  40                  45

Asn Asn Tyr Lys Thr Thr Pro Ser Arg Gln Glu Pro Ser Gln Gly Thr
    50                  55                  60
```

-continued

```
Thr Thr Phe Ala Val Thr Ser Lys Leu Thr Xaa Asp Lys Ser Arg Trp
 65                  70                  75                  80

Gln Gln Gly Asn Val Phe Ser Cys Ser Val Met His Glu Ala Leu His
                 85                  90                  95

Asn His Tyr Thr Gln Lys Xaa Ile Ser Leu
            100                 105

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AG-SEED
<220> FEATURE:
<221> NAME/KEY: MOD_RES
<222> LOCATION: (35)..(35)
<223> OTHER INFORMATION: Lys or Ser
<220> FEATURE:
<221> NAME/KEY: MOD_RES
<222> LOCATION: (75)..(75)
<223> OTHER INFORMATION: Val or Thr
<220> FEATURE:
<221> NAME/KEY: MOD_RES
<222> LOCATION: (103)..(103)
<223> OTHER INFORMATION: Thr or Ser

<400> SEQUENCE: 2

Gly Gln Pro Phe Arg Pro Glu Val His Leu Leu Pro Pro Ser Arg Glu
 1               5                  10                  15

Glu Met Thr Lys Asn Gln Val Ser Leu Thr Cys Leu Ala Arg Gly Phe
                 20                  25                  30

Tyr Pro Xaa Asp Ile Ala Val Glu Trp Glu Ser Asn Gly Gln Pro Glu
             35                  40                  45

Asn Asn Tyr Lys Thr Thr Pro Ser Arg Gln Glu Pro Ser Gln Gly Thr
 50                  55                  60

Thr Thr Phe Ala Val Thr Ser Lys Leu Thr Xaa Asp Lys Ser Arg Trp
 65                  70                  75                  80

Gln Gln Gly Asn Val Phe Ser Cys Ser Val Met His Glu Ala Leu His
                 85                  90                  95

Asn His Tyr Thr Gln Lys Xaa Ile Ser Leu
            100                 105

<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GA-SEED
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
```

```
<222> LOCATION: (67)..(67)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 3
```

Gly Gln Pro Arg Glu Pro Gln Val Tyr Thr Leu Pro Pro Ser Glu
1               5                   10                  15

Glu Leu Ala Leu Asn Glu Xaa Val Thr Leu Thr Cys Leu Val Lys Gly
            20                  25                  30

Phe Tyr Pro Ser Asp Ile Ala Val Glu Trp Leu Gln Gly Ser Gln Glu
        35                  40                  45

Leu Pro Arg Glu Lys Tyr Leu Thr Trp Xaa Pro Val Xaa Asp Ser Asp
    50                  55                  60

Gly Ser Xaa Phe Leu Tyr Ser Ile Leu Arg Val Xaa Ala Xaa Asp Trp
65              70                  75                  80

Lys Lys Gly Asp Thr Phe Ser Cys Ser Val Met His Glu Ala Leu His
                85                  90                  95

Asn His Tyr Thr Gln Lys Ser Leu Asp Arg
                100                 105

```
<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GA-SEED
<220> FEATURE:
<221> NAME/KEY: MOD_RES
<222> LOCATION: (23)..(23)
<223> OTHER INFORMATION: Leu or Gln
<220> FEATURE:
<221> NAME/KEY: MOD_RES
<222> LOCATION: (58)..(58)
<223> OTHER INFORMATION: Ala or Thr
<220> FEATURE:
<221> NAME/KEY: MOD_RES
<222> LOCATION: (61)..(61)
<223> OTHER INFORMATION: Leu, Val, Asp or Thr
<220> FEATURE:
<221> NAME/KEY: MOD_RES
<222> LOCATION: (67)..(67)
<223> OTHER INFORMATION: Phe, Ala, Asp, Glu, Gly, His, Lys, Asn, Pro,
      Gln, Arg, Ser or Thr
<220> FEATURE:
<221> NAME/KEY: MOD_RES
<222> LOCATION: (76)..(76)
<223> OTHER INFORMATION: Ala or Thr
<220> FEATURE:
<221> NAME/KEY: MOD_RES
<222> LOCATION: (78)..(78)
<223> OTHER INFORMATION: Glu or Asp

<400> SEQUENCE: 4
```

Gly Gln Pro Arg Glu Pro Gln Val Tyr Thr Leu Pro Pro Ser Glu
1               5                   10                  15

Glu Leu Ala Leu Asn Glu Xaa Val Thr Leu Thr Cys Leu Val Lys Gly
            20                  25                  30

Phe Tyr Pro Ser Asp Ile Ala Val Glu Trp Leu Gln Gly Ser Gln Glu

```
                35                  40                  45
Leu Pro Arg Glu Lys Tyr Leu Thr Trp Xaa Pro Val Xaa Asp Ser Asp
 50                  55                  60

Gly Ser Xaa Phe Leu Tyr Ser Ile Leu Arg Val Xaa Ala Xaa Asp Trp
 65                  70                  75                  80

Lys Lys Gly Asp Thr Phe Ser Cys Ser Val Met His Glu Ala Leu His
                 85                  90                  95

Asn His Tyr Thr Gln Lys Ser Leu Asp Arg
                100                 105

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AG-SEED

<400> SEQUENCE: 5

Gly Gln Pro Phe Arg Pro Glu Val His Leu Leu Pro Pro Ser Arg Glu
 1               5                  10                  15

Glu Met Thr Lys Asn Gln Val Ser Leu Thr Cys Leu Ala Arg Gly Phe
                20                  25                  30

Tyr Pro Lys Asp Ile Ala Val Glu Trp Glu Ser Asn Gly Gln Pro Glu
                35                  40                  45

Asn Asn Tyr Lys Thr Thr Pro Ser Arg Gln Glu Pro Ser Gln Gly Thr
 50                  55                  60

Thr Thr Phe Ala Val Thr Ser Lys Leu Thr Val Asp Lys Ser Arg Trp
 65                  70                  75                  80

Gln Gln Gly Asn Val Phe Ser Cys Ser Val Met His Glu Ala Leu His
                 85                  90                  95

Asn His Tyr Thr Gln Lys Thr Ile Ser Leu
                100                 105

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GA-SEED

<400> SEQUENCE: 6

Gly Gln Pro Arg Glu Pro Gln Val Tyr Thr Leu Pro Pro Ser Glu
 1               5                  10                  15

Glu Leu Ala Leu Asn Glu Leu Val Thr Leu Thr Cys Leu Val Lys Gly
                20                  25                  30

Phe Tyr Pro Ser Asp Ile Ala Val Glu Trp Leu Gln Gly Ser Gln Glu
                35                  40                  45

Leu Pro Arg Glu Lys Tyr Leu Thr Trp Ala Pro Val Leu Asp Ser Asp
 50                  55                  60

Gly Ser Phe Phe Leu Tyr Ser Ile Leu Arg Val Ala Ala Glu Asp Trp
 65                  70                  75                  80

Lys Lys Gly Asp Thr Phe Ser Cys Ser Val Met His Glu Ala Leu His
                 85                  90                  95
```

Asn His Tyr Thr Gln Lys Ser Leu Asp Arg
            100                 105

<210> SEQ ID NO 7
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AG-SEED

<400> SEQUENCE: 7

Gly Gln Pro Phe Glu Pro Glu Val His Thr Leu Pro Pro Ser Arg Glu
1               5                   10                  15

Glu Met Thr Lys Asn Gln Val Ser Leu Thr Cys Leu Val Arg Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Ser Arg Leu Glu Pro Ser Gln Gly Thr
    50                  55                  60

Thr Thr Phe Ala Val Thr Ser Lys Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu
            100                 105

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GA-SEED

<400> SEQUENCE: 8

Gly Gln Pro Arg Glu Pro Gln Val Tyr Thr Leu Pro Pro Ser Glu
1               5                   10                  15

Glu Leu Ala Leu Asn Asn Gln Val Thr Leu Thr Cys Leu Val Lys Gly
            20                  25                  30

Phe Tyr Pro Ser Asp Ile Ala Val Glu Trp Glu Ser Asn Gly Gln Pro
        35                  40                  45

Glu Pro Arg Glu Lys Tyr Leu Thr Trp Ala Pro Val Leu Asp Ser Asp
    50                  55                  60

Gly Ser Phe Phe Leu Tyr Ser Ile Leu Arg Val Asp Ala Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<223> OTHER INFORMATION: hu225 VL sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gln Asn Asn Asn Trp Pro Thr
                85                  90                  95

Thr Phe Gly Gln Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu225 kinetic variants
<220> FEATURE:
<221> NAME/KEY: MOD_RES
<222> LOCATION: (1)..(1)
<223> OTHER INFORMATION: Asp or Leu
<220> FEATURE:
<221> NAME/KEY: MOD_RES
<222> LOCATION: (27)..(27)
<223> OTHER INFORMATION: Gln, Met or Arg
<220> FEATURE:
<221> NAME/KEY: MOD_RES
<222> LOCATION: (31)..(31)
<223> OTHER INFORMATION: Thr or Val
<220> FEATURE:
<221> NAME/KEY: MOD_RES
<222> LOCATION: (32)..(32)
<223> OTHER INFORMATION: Asn, Arg, Phe or Met
<220> FEATURE:
<221> NAME/KEY: MOD_RES
<222> LOCATION: (49)..(49)
<223> OTHER INFORMATION: Lys or Met
<220> FEATURE:
<221> NAME/KEY: MOD_RES
<222> LOCATION: (50)..(50)
<223> OTHER INFORMATION: Tyr or Trp
<220> FEATURE:
<221> NAME/KEY: MOD_RES
<222> LOCATION: (92)..(92)
<223> OTHER INFORMATION: Asn, Arg, Ser, Tyr, or Met
<220> FEATURE:
<221> NAME/KEY: MOD_RES
<222> LOCATION: (93)..(93)
<223> OTHER INFORMATION: Asn or Glu
<220> FEATURE:
<221> NAME/KEY: MOD_RES
<222> LOCATION: (96)..(96)
<223> OTHER INFORMATION: Thr or Asn

<400> SEQUENCE: 10

Xaa Ile Gln Met Thr Gln Ser Pro Ser Ser Leu Ser Ala Ser Val Gly
1               5                   10                  15

Asp Arg Val Thr Ile Thr Cys Arg Ala Ser Xaa Ser Ile Gly Xaa Xaa
```

```
                20                  25                  30
Ile His Trp Tyr Gln Gln Lys Pro Gly Lys Ala Pro Lys Leu Leu Ile
            35                  40                  45

Xaa Xaa Ala Ser Glu Ser Ile Ser Gly Val Pro Ser Arg Phe Ser Gly
        50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gln Asn Xaa Xaa Trp Pro Xaa
                85                  90                  95

Thr Phe Gly Gln Gly Thr Lys Val Glu Ile Lys
            100                 105

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu225 VH sequence

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Phe Ser Leu Thr Asn Tyr
            20                  25                  30

Gly Val His Trp Met Arg Gln Ala Pro Gly Gln Gly Leu Glu Trp Ile
        35                  40                  45

Gly Val Ile Trp Ser Gly Gly Asn Thr Asp Tyr Asn Thr Pro Phe Thr
    50                  55                  60

Ser Arg Val Thr Ile Thr Ser Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu225 VH kinetic variants
<220> FEATURE:
<221> NAME/KEY: MOD_RES
<222> LOCATION: (28)..(28)
<223> OTHER INFORMATION: Ser or Trp
<220> FEATURE:
<221> NAME/KEY: MOD_RES
<222> LOCATION: (53)..(53)
<223> OTHER INFORMATION: Ser, Ala, Glu, His, Gln or Arg
<220> FEATURE:
<221> NAME/KEY: MOD_RES
<222> LOCATION: (56)..(56)
<223> OTHER INFORMATION: Asn, Ile, Leu, Met, Lys or Arg
<220> FEATURE:
<221> NAME/KEY: MOD_RES
<222> LOCATION: (58)..(58)
```

```
<223> OTHER INFORMATION: Asp, Glu, Gln or Arg
<220> FEATURE:
<221> NAME/KEY: MOD_RES
<222> LOCATION: (74)..(74)
<223> OTHER INFORMATION: Ser or Trp
<220> FEATURE:
<221> NAME/KEY: MOD_RES
<222> LOCATION: (100)..(100)
<223> OTHER INFORMATION: Thr, Phe, Trp or Asp
<220> FEATURE:
<221> NAME/KEY: MOD_RES
<222> LOCATION: (101)..(101)
<223> OTHER INFORMATION: Tyr or Trp
<220> FEATURE:
<221> NAME/KEY: MOD_RES
<222> LOCATION: (103)..(103)
<223> OTHER INFORMATION: Asp or Glu

<400> SEQUENCE: 12

Glu Val Gln Leu Val Gln Ser Gly Ala Glu Val Lys Lys Pro Gly Ala
1               5                   10                  15

Ser Val Lys Val Ser Cys Lys Ala Ser Gly Phe Xaa Leu Thr Asn Tyr
            20                  25                  30

Gly Val His Trp Met Arg Gln Ala Pro Gly Gln Gly Leu Glu Trp Ile
        35                  40                  45

Gly Val Ile Trp Xaa Gly Gly Xaa Thr Xaa Tyr Asn Thr Pro Phe Thr
    50                  55                  60

Ser Arg Val Thr Ile Thr Ser Asp Lys Xaa Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Xaa Xaa Tyr Xaa Tyr Glu Phe Ala Tyr Trp Gly Gln Gly
            100                 105                 110

Thr Leu Val Thr Val Ser Ser
        115

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu425 VL sequence

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg
            100                 105
```

-continued

```
<210> SEQ ID NO 14
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu425 VH sequence

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ser
        115                 120

<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder A12 VL sequence

<400> SEQUENCE: 15

Gln Ala Gly Leu Thr Gln Pro Pro Ser Val Ser Val Ala Pro Gly Gln
1               5                   10                  15

Thr Ala Arg Ile Thr Cys Gly Gly Asn Asn Ile Ala Arg Lys Ser Val
            20                  25                  30

His Trp Tyr Gln Gln Arg Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Gln
                85                  90                  95

Leu Tyr Val Phe Gly Thr Gly Thr Lys Val Thr Val Leu Gly Gln Pro
            100                 105                 110

Lys Ala Gly
        115

<210> SEQ ID NO 16
<211> LENGTH: 127
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: c-MET binder A12 VH sequence

<400> SEQUENCE: 16

Gln Val Gln Leu Gln Gln Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Gly Val Pro Tyr Tyr Gly Ser Gly Arg Tyr Gly Asp Gly Asn
            100                 105                 110

Trp Phe Asp Pro Trp Gly Gln Gly Thr Leu Val Thr Val Ser Ser
        115                 120                 125

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder B10 VL sequence

<400> SEQUENCE: 17

Gln Ser Val Leu Thr Gln Pro Pro Ser Thr Ser Gly Thr Pro Gly Gln
1               5                   10                  15

Arg Val Thr Ile Ser Cys Phe Gly Ser Ser Ser Asn Val Gly Val Asn
            20                  25                  30

Thr Val Asn Trp Tyr Arg Gln Leu Pro Gly Thr Ala Pro Lys Leu Leu
        35                  40                  45

Ile Tyr Asp Asn Asn Leu Arg Pro Ser Gly Val Pro Glu Arg Phe Ser
50                  55                  60

Gly Ser Lys Ser Gly Thr Ser Ala Ser Leu Ala Ile Thr Gly Leu Gln
65                  70                  75                  80

Ala Glu Asp Glu Gly Asp Tyr Tyr Cys Gln Ser Tyr Asp Ser Ser Leu
                85                  90                  95

Ser Asp Val Val Phe Gly Gly Gly Thr Lys Leu Thr Val Leu Gly Gln
            100                 105                 110

Pro Lys Ala Gly
        115

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder B10 VH sequence

```
<400> SEQUENCE: 18

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Ile Thr His Thr Tyr Trp Gly Gln Gly Thr Leu
            100                 105                 110

Val Thr Val Ser Ser
        115

<210> SEQ ID NO 19
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder C10 VL sequence

<400> SEQUENCE: 19

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Leu
                85                  90                  95

Trp Val Phe Gly Gly Gly Thr Lys Leu Thr Val Leu Gly Gln Pro Lys
            100                 105                 110

Ala Gly

<210> SEQ ID NO 20
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder C10 VH sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
```

```
                    20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Ser Leu Asn Phe Pro Asp Ile Ala Val Ala Gly Tyr Gly Asp Tyr
            100                 105                 110

Trp Gly Gln Gly Thr Leu Val Thr Val Ser Ser
        115                 120

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder E07 VL sequence

<400> SEQUENCE: 21

Gln Ser Ala Leu Thr Gln Pro Ala Ser Val Ser Gly Ser Leu Gly Gln
 1               5                  10                  15

Ser Ile Thr Ile Ser Cys Thr Gly Thr Ser Ser Asp Val Gly Gly Tyr
            20                  25                  30

Asp Tyr Val Ser Trp Tyr Gln Gln His Pro Gly Lys Ala Pro Gln Leu
        35                  40                  45

Met Ile Tyr Asp Val Thr Ser Arg Pro Ser Glu Val Ser Asn Arg Phe
    50                  55                  60

Ser Gly Ser Lys Ser Gly Thr Ser Ala Ser Leu Ala Ile Thr Gly Leu
 65                  70                  75                  80

Gln Ala Asp Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu Gly
            100                 105                 110

Gln Pro Lys Ala Gly
        115

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder E07 VH sequence

<400> SEQUENCE: 22

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45
```

-continued

```
Ile Gly Glu Ile Tyr His Ser Gly Ser Thr Asn Tyr Asn Pro Ser Leu
         50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Ser Gly Tyr Asp Phe Asp Tyr Trp Gly Gln Gly Thr
            100                 105                 110

Leu Val Thr Val Ser Ser
        115

<210> SEQ ID NO 23
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder G02 VL sequence

<400> SEQUENCE: 23

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
             20                  25                  30

Asn Tyr Val Ser Trp Tyr Gln Gln His Pro Gly Glu Ala Pro Lys Leu
         35                  40                  45

Met Ile Tyr Glu Val Ser Lys Arg Pro Ser Gly Val Pro Asp Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Trp Ser Tyr Ala Gly Ser
                 85                  90                  95

Tyr Thr Tyr Val Phe Gly Ala Gly Thr Lys Val Ser Val Leu Gly Gln
            100                 105                 110

Pro Lys Ala Gly
        115

<210> SEQ ID NO 24
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder G02 VH sequence

<400> SEQUENCE: 24

Glu Val Gln Leu Val Glu Thr Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Ala
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Met Gly Tyr Gly Thr Gly Ala Phe Asp Ile Trp Gly Gln Gly
            100                 105                 110

Thr Met Val Thr Val Ser Ser
        115

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder H06 VL sequence

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln His Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Gly Asp Tyr Tyr Cys Ala Ser Trp Asp Asp Asn Leu
                85                  90                  95

Asn Ala His Trp Val Phe Gly Gly Gly Thr Lys Leu Thr Val Val Ser
            100                 105                 110

Gln Pro Lys Ala Gly
        115

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder H06 VH sequence

<400> SEQUENCE: 26

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Thr Phe Thr Asn Leu
            20                  25                  30

Asp Ile Asn Trp Val Arg Gln Ala Ser Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Ser Thr Ser Val Ser Thr Ala Tyr
65                  70                  75                  80

Met Glu Leu Ser Ser Leu Glu Ala Glu Asp Thr Ala Val Tyr Tyr Cys
                85                  90                  95

Ala Arg Asn Arg Pro Glu Thr Gly Asp Phe Asp Tyr Trp Gly Gln Gly
```

Thr Leu Val Thr Val Ser Ser
        115

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder F03 VL sequence

<400> SEQUENCE: 27

Leu Pro Val Leu Thr Gln Pro His Ser Val Ser Gly Ser Pro Gly Lys
1               5                   10                  15

Thr Val Thr Ile Ser Cys Thr Gly Ser Ser Asp Tyr Ile Ala Ser Asn
            20                  25                  30

Tyr Val His Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Ser
                85                  90                  95

Ser Asn His Val Val Phe Gly Gly Gly Thr Lys Leu Thr Val Val Gly
            100                 105                 110

Gln Pro Lys Ala Gly
        115

<210> SEQ ID NO 28
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder F03 VH sequence

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ile Tyr
            20                  25                  30

Gly Met His Trp Val Arg Gln Ala Pro Gly Lys Gly Leu Glu Trp Leu
        35                  40                  45

Ala Phe Ile Arg His Asp Gly Gly Asn Asn Pro Tyr Ala Asp Ser Val
50                  55                  60

Lys Gly Arg Phe Thr Ile Ser Arg Asp Asn Ser Lys Asn Thr Leu Tyr
65                  70                  75                  80

Met Gln Met Ser Ser Leu Arg Pro Glu Asp Thr Ala Val Tyr Tyr Cys
                85                  90                  95

Ala Lys Asp Phe Ala Met Thr Gln Trp Leu Pro Glu Arg Gly Met Asp
            100                 105                 110

Val Trp Gly Gln Gly Thr Thr Val Thr Val Ser Ser
        115                 120

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder F06 VL sequence

<400> SEQUENCE: 29

Gln Leu Val Leu Thr Gln Ser Pro Ser Val Ser Val Ala Pro Gly Lys
1               5                   10                  15

Thr Ala Arg Ile Thr Cys Gly Gly Asn Asn Ile Arg Asn Val Gly Val
                20                  25                  30

His Trp Tyr Gln Lys Lys Pro Gly Gln Ala Pro Ile Leu Val Val Tyr
            35                  40                  45

Asp Asp Asp Asp Arg Pro Ser Gly Val Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ala Thr Asp Gln
                85                  90                  95

Ala Arg Gln Val Phe Gly Gly Gly Thr Lys Leu Thr Val Leu Gly Gln
            100                 105                 110

Pro Lys Ala Gly Cys
        115

<210> SEQ ID NO 30
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder F06 VH sequence

<400> SEQUENCE: 30

Gln Val Gln Leu Gln Gln Ser Gly Ala Glu Val Lys Lys Pro Gly Ser
1               5                   10                  15

Ser Ala Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Arg Gly Tyr Asp Tyr Tyr Tyr Tyr Gly Met Asp
            100                 105                 110

Val Trp Gly Gln Gly Thr Thr Val Thr Val Ser Ser
        115                 120

<210> SEQ ID NO 31
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder B10v5 VL sequence

<400> SEQUENCE: 31

Glu Pro Val Leu Thr Gln Pro Pro Ser Val Ser Val Ala Pro Gly Glu
1               5                   10                  15

Thr Ala Thr Ile Pro Cys Gly Gly Asp Ser Leu Gly Ser Lys Ile Val
            20                  25                  30

His Trp Tyr Gln Gln Arg Pro Gly Gln Ala Pro Leu Leu Val Val Tyr
        35                  40                  45

Asp Asp Ala Ala Arg Pro Ser Gly Ile Pro Glu Arg Phe Ser Gly Ser
    50                  55                  60

Lys Ser Gly Thr Thr Ala Thr Leu Thr Ile Ser Ser Val Glu Ala Gly
65                  70                  75                  80

Asp Glu Ala Asp Tyr Phe Cys Gln Val Tyr Asp Tyr His Ser Asp Val
                85                  90                  95

Glu Val Phe Gly Gly Gly Thr Lys Leu Thr Val Leu Gly Gln Pro Lys
            100                 105                 110

Ala Ala

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder B10v5 VH sequence

<400> SEQUENCE: 32

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Ile Thr His Thr Tyr Trp Gly Gln Gly Thr Leu
            100                 105                 110

Val Thr Val Ser Ser
        115

<210> SEQ ID NO 33
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder CS06 VL sequence

```
<400> SEQUENCE: 33

Gln Leu Val Leu Thr Gln Ser Pro Ser Val Ser Val Ala Pro Gly Lys
1               5                   10                  15

Thr Ala Arg Ile Thr Cys Gly Gly Asn Asn Ile Arg Asn Val Gly Val
            20                  25                  30

His Trp Tyr Gln Lys Lys Pro Gly Gln Ala Pro Ile Leu Val Val Tyr
        35                  40                  45

Asp Asp Asp Asp Arg Pro Ser Gly Val Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ala Thr Asp Gln
                85                  90                  95

Arg Val Phe Gly Gly Gly Thr Lys Leu Thr Val Leu Gly Gln Pro Lys
            100                 105                 110

Ala Gly

<210> SEQ ID NO 34
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder CS06 VH sequence

<400> SEQUENCE: 34

Gln Val Gln Leu Gln Gln Ser Gly Ala Glu Val Lys Lys Pro Gly Ser
1               5                   10                  15

Ser Ala Lys Val Ser Cys Lys Ala Ser Gly Gly Thr Phe Ser Ser Asn
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ile Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Arg Gly Tyr Tyr Tyr Tyr Tyr Tyr Gly Met Asp
            100                 105                 110

Val Trp Gly Gln Gly Thr Thr Val Thr Val Ser Ser
        115                 120

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: glycine-serine linker

<400> SEQUENCE: 35

Gly Gly Gly Gly Ser Gly Gly Gly Gly Ser Gly Gly Gly Gly Ser
1               5                   10                  15

Gly Gly Gly Ser
```

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: hinge 1

<400> SEQUENCE: 36

Glu Pro Lys Ser Ser Asp Lys Thr His Thr Cys Pro Pro Cys Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: hinge 2

<400> SEQUENCE: 37

Glu Pro Lys Ser Cys Asp Lys Thr His Thr Cys Pro Pro Cys Pro
1               5                   10                  15

<210> SEQ ID NO 38
<211> LENGTH: 99
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: CL sequence

<400> SEQUENCE: 38

Pro Ser Val Thr Leu Phe Pro Pro Ser Ser Glu Glu Leu Gln Ala Asn
1               5                   10                  15

Lys Ala Thr Leu Val Cys Leu Ile Ser Asp Phe Tyr Pro Gly Ala Val
            20                  25                  30

Thr Val Ala Trp Lys Ala Asp Ser Ser Pro Val Lys Ala Gly Val Glu
        35                  40                  45

Thr Thr Thr Pro Ser Lys Gln Ser Asn Asn Lys Tyr Ala Ala Ser Ser
    50                  55                  60

Tyr Leu Ser Leu Thr Pro Glu Gln Trp Lys Ser His Arg Ser Tyr Ser
65                  70                  75                  80

Cys Gln Val Thr His Glu Gly Ser Thr Val Glu Lys Thr Val Ala Pro
                85                  90                  95

Thr Glu Cys

<210> SEQ ID NO 39
<211> LENGTH: 98
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: CH1 sequence

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH2 domain

<400> SEQUENCE: 40

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 41
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH3 domain (AG)

<400> SEQUENCE: 41

Gly Gln Pro Phe Arg Pro Glu Val His Leu Leu Pro Pro Ser Arg Glu
1               5                   10                  15

Glu Met Thr Lys Asn Gln Val Ser Leu Thr Cys Leu Ala Arg Gly Phe
            20                  25                  30

Tyr Pro Lys Asp Ile Ala Val Glu Trp Glu Ser Asn Gly Gln Pro Glu
            35                  40                  45

Asn Asn Tyr Lys Thr Thr Pro Ser Arg Gln Glu Pro Ser Gln Gly Thr
        50                  55                  60

```
Thr Thr Phe Ala Val Thr Ser Lys Leu Thr Val Asp Lys Ser Arg Trp
 65                  70                  75                  80

Gln Gln Gly Asn Val Phe Ser Cys Ser Val Met His Glu Ala Leu His
             85                  90                  95

Asn His Tyr Thr Gln Lys Thr Ile Ser Leu Ser Pro Gly Lys
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH3 domain (GA)

<400> SEQUENCE: 42

Gly Gln Pro Arg Glu Pro Gln Val Tyr Thr Leu Pro Pro Ser Glu
1               5                   10                  15

Glu Leu Ala Leu Asn Glu Leu Val Thr Leu Thr Cys Leu Val Lys Gly
             20                  25                  30

Phe Tyr Pro Ser Asp Ile Ala Val Glu Trp Leu Gln Gly Ser Gln Glu
         35                  40                  45

Leu Pro Arg Glu Lys Tyr Leu Thr Trp Ala Pro Val Leu Asp Ser Asp
 50                  55                  60

Gly Ser Phe Phe Leu Tyr Ser Ile Leu Arg Val Ala Ala Glu Asp Trp
 65                  70                  75                  80

Lys Lys Gly Asp Thr Phe Ser Cys Ser Val Met His Glu Ala Leu His
             85                  90                  95

Asn His Tyr Thr Gln Lys Ser Leu Asp Arg Ser Pro Gly Lys
            100                 105                 110

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: humanized C225 VH kinetic variant S58R (IMGT
      numbering) hu225-L

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Phe Ser Leu Thr Asn Tyr
             20                  25                  30

Gly Val His Trp Met Arg Gln Ala Pro Gly Gln Gly Leu Glu Trp Ile
         35                  40                  45

Gly Val Ile Trp Arg Gly Gly Asn Thr Asp Tyr Asn Thr Pro Phe Thr
 50                  55                  60

Ser Arg Val Thr Ile Thr Ser Asp Lys Ser Thr Ser Thr Ala Tyr Met
 65                  70                  75                  80

Glu Leu Ser Ser Leu Arg Ser Glu Asp Thr Ala Val Tyr Tyr Cys Ala
             85                  90                  95

Arg Ala Leu Thr Tyr Tyr Asp Tyr Glu Phe Ala Tyr Trp Gly Gln Gly
            100                 105                 110
```

```
Thr Leu Val Thr Val Ser Ser
        115
```

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: humanized C225 VL kinetic variant N108Y (IMGT
      numbering) hu225-M

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gln Asn Tyr Asn Trp Pro Thr
                85                  90                  95

Thr Phe Gly Gln Gly Thr Lys Val Glu Ile Lys
            100                 105
```

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: humanized c225 VH T109D kinetic variant
      (hu225-H)

<400> SEQUENCE: 45

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Ser Leu Thr Asn Tyr
            20                  25                  30

Gly Val His Trp Met Arg Gln Ala Pro Gly Gln Gly Leu Glu Trp Ile
        35                  40                  45

Gly Val Ile Trp Ser Gly Gly Asn Thr Asp Tyr Asn Thr Pro Phe Thr
    50                  55                  60

Ser Arg Val Thr Ile Thr Ser Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Asp Tyr Tyr Asp Tyr Glu Phe Ala Tyr Trp Gly Gln Gly
            100                 105                 110

Thr Leu Val Thr Val Ser Ser
        115
```

<210> SEQ ID NO 46
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: humanized C225 VL N109E, T116N kinetic variant
      (hu225-H)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gln Asn Asn Glu Trp Pro Asn
                85                  90                  95

Thr Phe Gly Gln Gly Thr Lys Val Glu Ile Lys
            100                 105

<210> SEQ ID NO 47
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-Met binder BIO VL variants comprising single
      or multiple amino acid substitutions selected from V3A, T11V,
      T14S, R18S, R43Q, L45P, E74D, T85N, S86T, A90T, T92S G100A
      (numbering according to IMGT numbering)
<220> FEATURE:
<221> NAME/KEY: MOD_RES
<222> LOCATION: (3)..(3)
<223> OTHER INFORMATION: Val or Ala
<220> FEATURE:
<221> NAME/KEY: MOD_RES
<222> LOCATION: (10)..(10)
<223> OTHER INFORMATION: Thr or Val
<220> FEATURE:
<221> NAME/KEY: MOD_RES
<222> LOCATION: (13)..(13)
<223> OTHER INFORMATION: Thr or Ser
<220> FEATURE:
<221> NAME/KEY: MOD_RES
<222> LOCATION: (17)..(17)
<223> OTHER INFORMATION: Arg or Ser
<220> FEATURE:
<221> NAME/KEY: MOD_RES
<222> LOCATION: (38)..(38)
<223> OTHER INFORMATION: Arg or Gln
<220> FEATURE:
<221> NAME/KEY: MOD_RES
<222> LOCATION: (40)..(40)
<223> OTHER INFORMATION: Leu or Pro
<220> FEATURE:
<221> NAME/KEY: MOD_RES
<222> LOCATION: (61)..(61)
<223> OTHER INFORMATION: Glu or Asp
<220> FEATURE:
<221> NAME/KEY: MOD_RES
<222> LOCATION: (70)..(70)
<223> OTHER INFORMATION: Thr or Asn
<220> FEATURE:
<221> NAME/KEY: MOD_RES
```

```
<222> LOCATION: (71)..(71)
<223> OTHER INFORMATION: Ser or Thr
<220> FEATURE:
<221> NAME/KEY: MOD_RES
<222> LOCATION: (75)..(75)
<223> OTHER INFORMATION: Ala or Thr
<220> FEATURE:
<221> NAME/KEY: MOD_RES
<222> LOCATION: (77)..(77)
<223> OTHER INFORMATION: Thr or Ser
<220> FEATURE:
<221> NAME/KEY: MOD_RES
<222> LOCATION: (85)..(85)
<223> OTHER INFORMATION: Gly or Ala

<400> SEQUENCE: 47

Gln Ser Xaa Leu Thr Gln Pro Pro Ser Xaa Ser Gly Xaa Pro Gly Gln
1               5                   10                  15

Xaa Val Thr Ile Ser Cys Phe Gly Ser Ser Ser Asn Val Gly Val Asn
            20                  25                  30

Thr Val Asn Trp Tyr Xaa Gln Xaa Pro Gly Thr Ala Pro Lys Leu Leu
        35                  40                  45

Ile Tyr Asp Asn Asn Leu Arg Pro Ser Gly Val Pro Xaa Arg Phe Ser
    50                  55                  60

Gly Ser Lys Ser Gly Xaa Xaa Ala Ser Leu Xaa Ile Xaa Gly Leu Gln
65                  70                  75                  80

Ala Glu Asp Glu Xaa Asp Tyr Tyr Cys Gln Ser Tyr Asp Ser Ser Leu
                85                  90                  95

Ser Asp Val Val Phe Gly Gly Gly Thr Lys Leu Thr Val Leu Gly Gln
            100                 105                 110

Pro Lys Ala Gly
        115

<210> SEQ ID NO 48
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder B10 VH kinetic variant Q6E (IMGT
      numbering)
<220> FEATURE:
<221> NAME/KEY: MOD_RES
<222> LOCATION: (6)..(6)
<223> OTHER INFORMATION: Gln or Glu

<400> SEQUENCE: 48

Glu Val Gln Leu Val Xaa Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Ile Thr His Thr Tyr Trp Gly Gln Gly Thr Leu
            100                 105                 110
```

<210> SEQ ID NO 49
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-MET binder F06 VL sequence variants
      comprising single or multiple amino acid substitutions selected
      from Q1S, L2Y, S7P, K44Q, I51V, V71I (numbering acc. To IMGT
      numbering)
<220> FEATURE:
<221> NAME/KEY: MOD_RES
<222> LOCATION: (1)..(1)
<223> OTHER INFORMATION: Gln or Ser
<220> FEATURE:
<221> NAME/KEY: MOD_RES
<222> LOCATION: (2)..(2)
<223> OTHER INFORMATION: Leu or Tyr
<220> FEATURE:
<221> NAME/KEY: MOD_RES
<222> LOCATION: (7)..(7)
<223> OTHER INFORMATION: Ser or Pro
<220> FEATURE:
<221> NAME/KEY: MOD_RES
<222> LOCATION: (37)..(37)
<223> OTHER INFORMATION: Lys or Gln
<220> FEATURE:
<221> NAME/KEY: MOD_RES
<222> LOCATION: (44)..(44)
<223> OTHER INFORMATION: Ile or Val
<220> FEATURE:
<221> NAME/KEY: MOD_RES
<222> LOCATION: (57)..(57)
<223> OTHER INFORMATION: Val or Ile

<400> SEQUENCE: 49

Xaa Xaa Val Leu Thr Gln Xaa Pro Ser Val Ser Val Ala Pro Gly Lys
1               5                   10                  15

Thr Ala Arg Ile Thr Cys Gly Gly Asn Asn Ile Arg Asn Val Gly Val
            20                  25                  30

His Trp Tyr Gln Xaa Lys Pro Gly Gln Ala Pro Xaa Leu Val Val Tyr
        35                  40                  45

Asp Asp Asp Asp Arg Pro Ser Gly Xaa Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ala Thr Asp Gln
                85                  90                  95

Arg Val Phe Gly Gly Gly Thr Lys Leu Thr Val Leu Gly Gln Pro Lys
            100                 105                 110

Ala Gly Cys
        115

<210> SEQ ID NO 50
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder F06 VH variants comprising single
      or multiple amino acid substitutions selected from Q5V, A19V, M115I, M115L, M115V, M115A, M115F (numbering according to IMGT
numbering)
<220> FEATURE:
<221> NAME/KEY: MOD_RES
<222> LOCATION: (5)..(5)
<223> OTHER INFORMATION: Gln or Val
<220> FEATURE:
<221> NAME/KEY: MOD_RES
<222> LOCATION: (18)..(18)
<223> OTHER INFORMATION: Ala or Val
<220> FEATURE:
<221> NAME/KEY: MOD_RES
<222> LOCATION: (111)..(111)
<223> OTHER INFORMATION: Met, Ile, Leu, Val, Ala or Phe

<400> SEQUENCE: 50

Gln Val Gln Leu Xaa Gln Ser Gly Ala Glu Val Lys Lys Pro Gly Ser
1               5                   10                  15

Ser Xaa Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Arg Gly Tyr Asp Tyr Tyr Tyr Tyr Gly Xaa Asp
            100                 105                 110

Val Trp Gly Gln Gly Thr Thr Val Thr Val Ser Ser
        115                 120

<210> SEQ ID NO 51
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder B10v5 VL variants comprising
      single or multiple amino acid substitutions selected from E1S,
      P2Y, E17Q, T20R, P22T, R45K, L51V, T85N, S93R, F103Y (IMGT
      numbering)
<220> FEATURE:
<221> NAME/KEY: MOD_RES
<222> LOCATION: (1)..(1)
<223> OTHER INFORMATION: Glu or Ser
<220> FEATURE:
<221> NAME/KEY: MOD_RES
<222> LOCATION: (2)..(2)
<223> OTHER INFORMATION: Pro or Tyr
<220> FEATURE:
<221> NAME/KEY: MOD_RES
<222> LOCATION: (16)..(16)
<223> OTHER INFORMATION: Glu or Gln
<220> FEATURE:
<221> NAME/KEY: MOD_RES
<222> LOCATION: (19)..(19)
<223> OTHER INFORMATION: Thr or Arg
<220> FEATURE:
<221> NAME/KEY: MOD_RES
<222> LOCATION: (21)..(21)
<223> OTHER INFORMATION: Pro or Thr
<220> FEATURE:
<221> NAME/KEY: MOD_RES
<222> LOCATION: (38)..(38)
<223> OTHER INFORMATION: Arg or Lys
<220> FEATURE:

```
<221> NAME/KEY: MOD_RES
<222> LOCATION: (44)..(44)
<223> OTHER INFORMATION: Leu or Val
<220> FEATURE:
<221> NAME/KEY: MOD_RES
<222> LOCATION: (68)..(68)
<223> OTHER INFORMATION: Thr or Asn
<220> FEATURE:
<221> NAME/KEY: MOD_RES
<222> LOCATION: (76)..(76)
<223> OTHER INFORMATION: Ser or Arg
<220> FEATURE:
<221> NAME/KEY: MOD_RES
<222> LOCATION: (86)..(86)
<223> OTHER INFORMATION: Phe or Tyr

<400> SEQUENCE: 51

Xaa Xaa Val Leu Thr Gln Pro Pro Ser Val Ser Val Ala Pro Gly Xaa
1               5                   10                  15

Thr Ala Xaa Ile Xaa Cys Gly Gly Asp Ser Leu Gly Ser Lys Ile Val
            20                  25                  30

His Trp Tyr Gln Gln Xaa Pro Gly Gln Ala Pro Xaa Leu Val Val Tyr
        35                  40                  45

Asp Asp Ala Ala Arg Pro Ser Gly Ile Pro Glu Arg Phe Ser Gly Ser
    50                  55                  60

Lys Ser Gly Xaa Thr Ala Thr Leu Thr Ile Ser Xaa Val Glu Ala Gly
65              70                  75                  80

Asp Glu Ala Asp Tyr Xaa Cys Gln Val Tyr Asp Tyr His Ser Asp Val
                85                  90                  95

Glu Val Phe Gly Gly Gly Thr Lys Leu Thr Val Leu Gly Gln Pro Lys
            100                 105                 110

Ala Ala

<210> SEQ ID NO 52
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-MET binder CS06 VH kinetic variants
      comprising including single, double, triple or quadruple
      combination of the following listed mutations: Q3R, Y37N, N66I,
      G110S, D111.1Y, Y111.2D, S126Y (IMGT numbering)
<220> FEATURE:
<221> NAME/KEY: MOD_RES
<222> LOCATION: (3)..(3)
<223> OTHER INFORMATION: Gln or Arg
<220> FEATURE:
<221> NAME/KEY: MOD_RES
<222> LOCATION: (32)..(32)
<223> OTHER INFORMATION: Asn or Tyr
<220> FEATURE:
<221> NAME/KEY: MOD_RES
<222> LOCATION: (59)..(59)
<223> OTHER INFORMATION: Asn or Ile
<220> FEATURE:
<221> NAME/KEY: MOD_RES
<222> LOCATION: (102)..(102)
<223> OTHER INFORMATION: Ser or Gly
<220> FEATURE:
<221> NAME/KEY: MOD_RES
<222> LOCATION: (104)..(105)
<223> OTHER INFORMATION: Tyr or Asp
<220> FEATURE:
<221> NAME/KEY: MOD_RES
<222> LOCATION: (123)..(123)
<223> OTHER INFORMATION: Tyr or Ser
```

```
<400> SEQUENCE: 52

Gln Val Xaa Leu Gln Gln Ser Gly Ala Glu Val Lys Lys Pro Gly Ser
1               5                   10                  15

Ser Ala Lys Val Ser Cys Lys Ala Ser Gly Gly Thr Phe Ser Ser Xaa
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Xaa Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Arg Xaa Tyr Xaa Xaa Tyr Tyr Tyr Tyr Gly Met Asp
                100                 105                 110

Val Trp Gly Gln Gly Thr Thr Val Thr Val Xaa Ser
            115                 120

<210> SEQ ID NO 53
<211> LENGTH: 5
<212> TYPE: PRT
<213> ORGANISM: Unknown
<220> FEATURE:
<223> OTHER INFORMATION: Description of Unknown: SrtA signal motif
      sequence
<220> FEATURE:
<221> NAME/KEY: MOD_RES
<222> LOCATION: (3)..(3)
<223> OTHER INFORMATION: Asp, Glu, Ala, Asn, Gln or Lys

<400> SEQUENCE: 53

Leu Pro Xaa Thr Gly
1               5

<210> SEQ ID NO 54
<211> LENGTH: 5
<212> TYPE: PRT
<213> ORGANISM: Unknown
<220> FEATURE:
<223> OTHER INFORMATION: Description of Unknown: SrtA signal motif
      sequence
<220> FEATURE:
<221> NAME/KEY: MOD_RES
<222> LOCATION: (3)..(3)
<223> OTHER INFORMATION: Any amino acid

<400> SEQUENCE: 54

Leu Pro Xaa Thr Gly
1               5
```

BI-SPECIFIC ANTIBODIES FOR ENHANCED TUMOR SELECTIVITY AND INHIBITION AND USES THEREOF

This application is a National Stage entry under § 371 of International Application No. PCT/EP2016/001791, filed on Oct. 27, 2016, and which claims priority to European Patent Application Nos. i) 15192851.2, filed on Nov. 3, 2015; and ii) 16178010.1, filed on Jul. 5, 2016.

The instant application contains a Sequence Listing which has been submitted electronically in ASCII format and is hereby incorporated by reference in its entirety. Said ASCII copy, created on Mar. 23, 2018, is named 000588US_SL.txt and is 64,620 bytes in size.

FIELD OF THE INVENTION

The present invention concerns bi-specific antibodies, in particular EGFR×c-MET bi-specific antibodies, for enhanced tumor selectivity and inhibition, their use in the treatment of cancer and methods of producing the same.

BACKGROUND OF THE INVENTION

Cancer cells are often characterized by an aberrant expression of cell surface molecules, such as receptor tyrosine kinases one of which is the epidermal growth factor receptor (EGFR). EGFR is activated upon binding to the Epidermal Growth Factor (EGF) and other growth factor ligands, such as TGF-α, amphiregulin (AR), epiregulin (EP), betacelluin (BC), or HB-EGF (Normanno et al., Gene 366 (2006) 2-16). Upon ligand-induced dimerization and activation, several downstream signaling pathways are triggered, including RAS/MAPK, PI3K/Akt and STAT that regulate different cellular processes, including DNA synthesis and proliferation. EGFR signaling is commonly found deregulated in cancer through different mechanisms, including genetic mutations of the receptor. Signaling properties of mutant forms of EGFR in addition also show an altered cellular trafficking compared to wild type EGFR, since some of the regulatory proteins that balance the EGFR pathway present altered expression in cancer. Mutated EGFR is for example found in non small cell lung cancer (NSCLC) and 60-80% of colorectal cancers express a mutated EGFR.

In the advent of anti-EGFR based cancer therapy it was hypothesized that EGFR targeted therapy would be most effective in tumors overexpressing the protein, however studies quickly revealed that the levels of EGFR expression were not correlated with response to anti-EGFR antibodies, such as cetuximab (Liska Clin Cancer Res 17(3) February, 2011). Increased EGFR gene copy number, overexpression of EGFR ligand and TP53 mutations were shown to be associated with response to EGFR inhibitors in CRC (Khambata-Ford et al., J Clin Oncol 2007; 25:3230-7; Moroni et al., Lancet Oncol 2005; 6:279-86; Oden-Gangloff et al. Br J Cancer 2009; 100:1330-5; Tabernero J, J Clin Oncol. 2010 Mar. 1; 28(7):1181-9).

Side effects of current EGFR-targeted therapies targeting EGFR overexpressing cells suffer from toxicities due to basal expression of EGFR in tissues other than the tumor. For example, cetuximab which is a chimeric human-murine monoclonal antibody against EGFR, often causes skin toxicities, a phenomenon which is also observed in EGFR therapy with gefitinib (J Eur Acad Dermatol Venereol. 2010 April; 24(4):453-9); SpringerPlus 2013, 2:22).

Functionally, receptor tyrosine kinases also often times also show redundancy, which will compensate for the loss of one family member. One example is sustained ERBB3 signaling which is observed in some cases of EGFR mutant tumors treated with gefitinib (Science Vol. 316, 18 May 2007: p. 1039-1043). This functional redundancy can ultimately result in acquired tumor resistance to a therapeutic blockade of one family member (Engelmann et al. Science 316, 1039 (2007)). Acquired tumor resistance often results in relapse during a RTK inihibitor monotherapy.

Studies revealed that intrinsic resistance to EGFR-targeted therapy can be the result of downstream effector molecule activation such as KRAS which is seen in 35%-40% of CRCs (Knickelbein et al. Genes Dis. 2015 March; 2(1):4-12). Multiple studies have now shown that KRAS mutations in CRC confer resistance to cetuximab because of which it is recommended to limit cetuximab therapy to patients with wild-type KRAS tumors. However, about 25% of colorectal cancer (CRC) patients that are wild-type for KRAS, BRAF, PIK3CA and PTEN do not respond to treatment with EGFR inhibitors (J Clin Oncol. 2010 Mar. 1; 28(7):1254-61). Molecular analysis of the patients not responding to treatment by BEAMing revealed an amplification of the MET gene in these patients following treatment (Bardelli et al. Cancer Discov; 3(6); 658-73). Upregulation of hepatocyte growth factor receptor (HGFR, c-MET) expression and of its ligand HGF appears to be one of the major escape routes of tumors during EGFR-targeted monotherapy. This is also often accompanied by amplification of the gene encoding c-MET (Engelmann et al. Science 316, 1039 (2007); Clin Cancer Res 2011; 17:472-482). In vitro experiments with gefitinib treated HCC827 cells revealed a c-MET amplification of 5-10 fold (Engelmann et al. Science 316, 1039 (2007)).

The MET gene encodes the for hepatocyte growth factor receptor (HGFR, c-MET), which is a heterodimeric transmembrane receptor tyrosine kinase composed of an extracellular α-chain and a membrane-spanning β-chain linked via disulfide bonds and which has a single ligand, HGF, also known as scatter factor. Structurally, c-MET comprises several conserved protein domains, including sema, PSI (in plexins, semaphorins, integrins), 4 IPT repeats (in immunoglobulins, plexins, transcription factors), TM (transmembrane), JM (juxtamembrane), and TK (tyrosine kinase) domains. Binding of HGF to MET triggers receptor dimerization and transphosphorylation, leading to conformational changes in MET that activate the TK domain. C-MET mediates activation of downstream signaling pathways, including phosphoinositide 3-kinase (PI3K)/AKT, Ras-Rac/Rho, mitogen-activated protein kinase, and phospholipase C, that stimulate morphogenic, proliferative, and antiapoptotic activities as well as stimulating pathways involved in cell detachment, motility, and invasiveness.

Consistent with the role of c-MET in cell motility and morphogenesis, metastatic lesions typically exhibit higher expression levels of MET than primary tumors (Cipriani et al. Lung Cancer 2009, 63:169-179). Several approaches have been pursued to inhibit either the ligand HBF or the receptor to inhibit c-MET signaling. For example, AMG102/Rilotumumab binds preferentially to the mature biologically active form of HGF, interacting with the amino-terminal portion of the β-chain thereby inhibiting HGF binding. Another monoclonal antiobody (mAb) which was explored to inhibit HGF activity is Ficlatuzumab. Ficlatuzumab is a humanized IgG1 antibody that binds HGF ligand with high affinity and specificity thereby inhibiting c-MET/HGF biological activities.

Rilotumumab has been tested as monotherapy in patients carrying recurrent glioblastomas, metastatic renal carcinomas or ovarian cancers and in combination with chemotherapy in prostate cancers or with antiangiogenic agents in advanced solid tumors. Ficlatuzumab was tested both as monotherapy and in association with EGFR inhibitors in NSCLC (Biologics 2013; 7: 61-68). However, a phase II trial with ficlatuzumab did not reach its primary endpoint.

Thus, despite the fact that progress has been made in the development of both, anti-EGFR and anti-c-MET therapies, either as monotherapy or in combination, there is a continued need for improved anti-EGFR cancer therapies, which overcome the current limitations of anti-EGFR based therapies and prevent c-MET-driven tumor resistance.

SUMMARY OF THE INVENTION

The present inventors have surprisingly found that bispecific heterodimeric immunoglobulin molecules which bind to both EGFR and c-MET are effective in the treatment of EGFR and c-MET-expressing tumors.

In a first embodiment the present invention provides heterodimeric bispecific immunoglobulin molecule which comprises
  (i) a first Fab or scFv fragment which specifically binds to EGFR, and
  (ii) a second Fab or scFv fragment which specifically binds to c-MET, and
  (iii) an antibody hinge region, an antibody CH2 domain and an antibody CH3 domain comprising a hybrid protein-protein interaction interface domain wherein each of said interaction interface domain is formed by amino acid segments of the CH3 domain of a first member and amino acid segments of the CH3 domain of said second member, wherein said protein-protein interface domain of the first chain is interacting with the protein-protein-interface of the second chain by homodimerization of the corresponding amino acid segments of the same member of the immunoglobulin superfamily within said interaction domains,
  wherein the first or second engineered immunoglobulin chain has the polypeptide sequence ("AG-SEED"):
GQPFRPEVHLLPPSREEMTKNQVSLTCLARGFYPX$_1$DIAVEWESNGQPENNYKTTP SRQEPSQGTT TFAVTSKLTX$_2$DKSRWQQGNVFSCSVMHEALHNHYTQKX$_3$ISL (SEQ ID NO:1), wherein X$_1$, X$_2$ and X$_3$ may be any amino acid.

In one embodiment, in the heterodimeric bispecific immunoglobulin molecule of the invention the first member of the immunoglobulin super family is IgG and the second member is IgA.

In one embodiment X1 is K or S, X2 is V or T, and X3 is T or S in the heterodimeric bispecific immunoglobulin molecule of the invention as disclosed above (SEQ ID NO: 2).

In one embodiment, the first or second engineered immunoglobulin chain of the heterodimeric bispecific immunoglobulin molecule according to the invention has the polypeptide sequence ("GA-SEED"):
GQPREPQVYTLPPPSEELALNEX1VTLTCLVKGFYPSDIAVEWLQGSQELPRE KYLTWX2PVX3DSD GSX4FLYSILRVX5AX6DWKKGDTFSCSVMHEALHNHYTQKSLDR, wherein X1, X2, X3, X4, X5 and X6 may be any amino acid (SEQ ID NO: 3).

According to one embodiment, X1 is L or Q, X2 is A or T, X3 is L, V, D, or T; X4 is F, A, D, E, G, H, K, N, P, Q, R, S, or T; X5 is A or T, and X6 is E or D in the inventive heterodimeric bispecific immunoglobulin molecule (SEQ ID NO: 4).

In one embodiment, the first engineered immunoglobulin chain of the inventive heterodimeric bispecific immunoglobulin molecule comprises the polypeptide sequence ("AG-SEED"):
GQPFRPEVHLLPPSREEMTKNQVSLTCLARGFYPK-DIAVEWESNGQPENNYK TTPSRQEPSQGTT TFAVTSKLTVDKSRWQQGNVFSCSVMHEALHN-HYTQKTISL (SEQ ID NO: 5) and the second engineered immunoglobulin chain of the inventive heterodimeric bispecific immunoglobulin molecule comprises the polypeptide sequence ("GA-SEED"):
GQPREPQVYTLPPPSEELALNELVTLTCLVKGFYPS-DIAVEWLQGSQELPREK YLTWAPVLDSDG SFFLYSILRVAAEDWKKGDTFSCSVMHEALHN-HYTQKSLDR (SEQ ID NO: 6).

According to one embodiment, the first engineered immunoglobulin chain of the inventive heterodimeric bispecific immunoglobulin molecule as disclosed above has the polypeptide sequence ("AG-SEED"):
GQPFEPEVHTLPPSREEMTKNQVSLTCLVRGFYPS-DIAVEWESNGQPENNYKT TPSRLEPSQGTT TFAVTSKLTVDKSRWQQGNVFSCSVMHEALHN-HYTQKSLSL (SEQ ID NO: 7) and the second engineered immunoglobulin chain of the inventive heterodimeric bispecific immunoglobulin molecule as disclosed above has the polypeptide sequence ("GA-SEED"):
GQPREPQVYTLPPPSEELALNNQVTLTCLVKGF-YPSDIAVEWESNGQPEPREK YLTWAPVLDSDG SFFLYSILRVDASRWQQGNVFSCSVMHEALHN-HYTQKSLSL (SEQ ID NO: 8).

In one embodiment, the first Fab or scFv fragment of the inventive heterodimeric bispecific immunoglobulin molecule as disclosed above binds EGFR with an K$_D$ of at least $5 \times 10^{-8}$ M.

In one embodiment, the second Fab or scFv fragment of the inventive heterodimeric bispecific immunoglobulin molecule as disclosed above binds c-MET with an K$_D$ of at least $5 \times 10^{-8}$ M.

According to one embodiment, the first Fab or scFv fragment of the inventive heterodimeric bispecific immunoglobulin molecule is derived from cetuximab (C225).

In a preferred embodiment, the first Fab or scFv fragment comprises VL and VH sequences selected form the group consisting of SEQ ID NO: 9, SEQ ID NO:10, SEQ ID NO: 11, SEQ ID NO: 12, SEQ ID NO: 43, SEQ ID NO: 44, SEQ ID NO: 45, SEQ ID NO: 46.

In a preferred embodiment, the wherein the second Fab or scFv fragment comprises VL sequences selected form the group consisting of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 47, SEQ ID NO: 49, SEQ ID NO: 51.

In a preferred embodiment, the VL sequences of the first Fab or scFv fragment of the inventive heterodimeric bispecific immunoglobulin molecule are selected the VH sequences of said second Fab fragment are selected from the group consisting of SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO:34, SEQ ID NO: 48, SEQ ID NO: 50, or SEQ ID NO: 52.

According to a more preferred embodiment, the first and second Fab or scFv fragments of the inventive heterodimeric bispecific immunoglobulin molecule as disclosed above comprise the amino acid sequences SEQ ID NO: 9, SEQ ID NO: 43, SEQ ID NO: 17, SEQ ID NO:18, or SEQ ID NO: 47, SEQ ID NO: 48, or SEQ ID NO: 11, SEQ ID NO: 44, SEQ ID NO: 31, SEQ ID NO: 51, SEQ ID NO:32, or SEQ ID NO:45, SEQ ID NO: 46, SEQ ID NO: 29, SEQ ID NO: 49, SEQ ID NO: 30, SEQ ID NO: 50, or SEQ ID NO: 45, SEQ ID NO: 46, SEQ ID NO: 33, SEQ ID NO: 34, SEQ ID NO: 52, or SEQ ID NO: 11, SEQ ID NO: 44, SEQ ID NO: 33, SEQ ID NO: 34, SEQ ID NO: 52.

According to a more preferred embodiment the first and second Fab or scFv fragments of the inventive heterdimeric bispecific immunoglobulin molecule as disclosed above comprise the amino acid sequences SEQ ID NO: 11, SEQ ID NO: 44, SEQ ID NO: 33, SEQ ID NO: 34, SEQ ID NO: 52, or SEQ ID NO:45, SEQ ID NO: 46, SEQ ID NO: 29, SEQ ID NO: 49, SEQ ID NO: 30, SEQ ID NO: 50.

In one embodiment, the Fc domain of the heterodimeric bispecific immunoglobulin molecule according to the invention interacts with FcRn.

In one embodiment, the amino acids of the inventive heterodimeric bispecific immunoglobulin molecule which interact with FcRn are derived from human IgG1.

In one embodiment the inventive heterodimeric bispecific immunoglobulin molecule as disclosed above mediates antibody-dependent cellular cytotoxicity.

In one embodiment, the invention provides an isolated polynucleotide encoding any of the amino acid sequences as disclosed above.

In one embodiment, the invention provides a vector, which comprises at least one inventive polynucleotide.

According to one embodiment, the invention provides for a host cell which comprises at least one polynucleotide according to the invention, or which comprises at least one vector according to the invention.

In one embodiment, the invention provides a method for producing a heterodimeric bispecific immunoglobulin molecule of the invention as disclosed above, with the inventive process comprising:
 culturing a host cell according to the invention under conditions sufficient for the heterologous expression of said heterodimeric bispecific immunoglobulin molecule
 purifying said heterodimeric bispecific immunoglobulin molecule In one embodiment the invention provides the heterodimeric bispecific immunoglobulin molecule of the invention which is obtainable by the inventive method as disclosed above.

According to one embodiment, the heterodimeric bispecific immunoglobulin molecule according to the invention as disclosed above is covalently coupled to at least one linker.

In one embodiment the linker of the inventive heterodimeric bispecific immunoglobulin molecule is coupled to a dye, radioisotope or cytotoxin.

In one embodiment, at least one of the Fab or scFv light chains of the inventive heterodimeric bispecific immunoglobulin molecule is coupled to a dye, radioisotope, or cytotoxin.

In one embodiment at least one linker as disclosed above is covalently coupled to at least one of the Fab or scFv light chains of the inventive heterodimeric bispecific immunoglobulin molecule as disclosed above.

According to one embodiment the inventive heterodimeric bispecific immunoglobulin molecule comprises two linkers covalently coupled to the Fab or scFv light chains the heterodimeric bispecific immunoglobulin molecule.

In one embodiment, the Fab or scFv light chains and/or the CH3 domains and/or the CH2 domains of the inventive heterodimeric bispecific immunoglobulin molecule are coupled to a linker, whereby said linker is covalently coupled to a dye, radioisotope, or cytotoxin.

According to one embodiment, the heterodimeric bispecific immunoglobulin molecule of the invention is for use in the treatment of cancer.

In one embodiment, the inventive heterodimeric bispecific immunoglobulin molecule is for use in the treatment of cancer.

In one embodiment, the invention provides a composition, which comprises the heterodimeric bispecific immunoglobulin molecule of the invention as disclosed above and at least one further ingredient.

In one embodiment, the invention provides a pharmaceutical composition which comprises the inventive heterodimeric bispecific immunoglobulin molecule above and at least one further ingredient, or the inventive composition as disclosed above.

In one embodiment, the pharmaceutical composition of the invention is for use in the treatment of cancer.

In one embodiment, the invention provides a method of treating a subject in need thereof inflicted with cancer, wherein the treatment comprises administering to said subject a therapeutically effective amount of the inventive pharmaceutical composition as disclosed above.

BRIEF DESCRIPTION OF THE DRAWINGS

FIG. 6: Inhibition of c-MET phosphorylation in (A) NCI-H596 cells, (B) in A549 cells.

FIG. 7: Quantitative summary of the c-MET phosphorylation inhibition (A) NCI-H596 cells, (B) A549 cells.

FIG. 8: (A) Inhibition of c-MET phosphorylation in MKN-45 cells using the immunoglobulin molecules indicated, (B) inhibition of EGFR phosphorylation in NCI-H596 cells using the immunoglobulin molecules as indicated.

FIG. 9: Cytotoxicity assays on A549 cells. (A) control with no toxin conjugated, (B) assay using Fab-MMAE-CL coupled antibodies as indicated, MMAE: monomethyl auristatin E.

FIG. 10: Cytotoxicity assays on (A) EBC-1 cells, (B) NCI-H441 cells.

FIG. 11: Cytotoxicity assay on MKN-45 cells which express high levels of c-Met and moderate levels of EGFR.

FIG. 12: Depicted is the enhanced inhibition of c-MET phosphorylation in HGF-dependent cancer cell lines: (A) NCI-H596, (B) KP-4.

FIG. 15: Depicted are the results of a cellular binding assay using the antibody and immunoglobulin molecules indicated.

FIG. 16: Experimental and calculated binding affinity for computationally designed point mutants of C225. Letters in superscript denote the following: a—The KD (nM) for wild type (C225) and mutant mAbs was determined by surface plasmon resonance (SPR). Where n>1, the standard deviation is given. Mutations that improved affinity (p<0.01) are in boldface. b—Experimental binding affinity relative to wild type (kcal/mol). c—Predicted binding affinity relative to wild type using Rosetta. d—Predicted change in Rosetta pair energy across the interface. e—Predicted change hydrogen bond energy across the interface. f—Calculated hydrogen bond energy of mutated residue side chain. g—Predicted change in folding energy of the isolated antibody. NQ: Not Quantifiable, very weak binding.

FIG. 17: Kinetic parameters of monovalent parental SEED antibodies in comparison to—METxEGFR bsAbs binding to soluble c-MET and EGFR extracellular domains. Kinetic constants were determined for cetuximab and matuzumab as references. Antibodies were captured by anti-human Fc Octet biosensors and binding kinetics were analyzed at indicated analyte concentrations (25 to 0.8 nM or alternatively 50 to 3.1 nM). Melting temperatures (Tm) were determined by thermal shift assays. Legend: n.d.=not determined; $K_D$=affinity constant, ka=association constant; kd=dissociation constant; Tm=melting temperature; oa=one-armed.

FIG. 18: Cell surface receptor densities of human c-MET and EGFR on several tumor cell lines from various indications. Keratinocytes (NHEK.f-c.) were used to evaluate EGFR-related skin toxicity and the liver cell line HepG2 for c-MET mediated liver toxicity. Density values are presented as mean molecules per cell of triplicates with standard deviations given in percent. Legend: ACA=adenocarcinoma, CA=carcinoma.

FIG. 19: Inhibition of c-MET and EGFR phosphorylation by c-METxEGFR bsAbs. IC50 values were calculated upon 3PL fitting of dose-response curves using GraphPad Prism. Standard deviations (s.d.) were calculated for at least two independent experiments carried out in duplicates. n=number of independent experiments.

FIG. 23: Cytotoxicity of bispecific c-METxEGFR ADC on tumor cell line A431 and keratinocytes. $EC_{50}$ values for A431 cells and $IC_{50}$ values for keratinocytes (NHEK.f-c.) were calculated by sigmoidal curve fitting using GraphPad Prism 5 (GraphPad Software, Inc). Asterisks indicate poor fitting results because curves do not reach a saturating plateau at the highest concentration (*). $ED_{80}$ represents the ADC concentration at which 80% of cells are killed in A431 cells in comparison to untreated cells, $TD_{20}$ indicates the dose at which cell viability in keratinocytes is reduced by 20%. Two definitions for an in vitro translational therapeutic index or therapeutic window were calculated: The difference of $IC_{50}$ and $EC_{50}$ as well as the ratio of $TD_{20}$ to $ED_{80}$.

FIG. 25: Synergistic effect of CS06x225-H on inhibition of c-MET, EGFR, and AKT phosphorylation. (A) A549 cells were incubated with 300 nM of the respective mAbs as indicated for 3 h and stimulated with HGF and EGF. Cell lysates were subjected to Western blotting and both phosphorylated and total EGFR, c-MET, and AKT were detected. GAPDH was used as a loading control. (B) Quantification of phospho-AKT levels in A549 cells after treatment with 500 nM mAbs as well as combinations of control mAbs (500 nM each) and stimulation with HGF and EGF. Cell lysates were subjected to electrochemiluminescence (ECL) ELISA. (C) ECL ELISA of mAbs treated and HGF-stimulated A549 cell lysates for phosphorylated c-MET indicated increased potency of CS06x225-H in comparison to the combination of oa CS06 and oa 225-H. (D) A549 cells were treated with varying concentrations of mAbs without stimulation and lysates were subjected to ECL ELISA detecting phosphorylated c-MET levels. B10v5x225-M and B10v5x225-H demonstrated comparable partial agonism to LY2875358.

Figure 1:
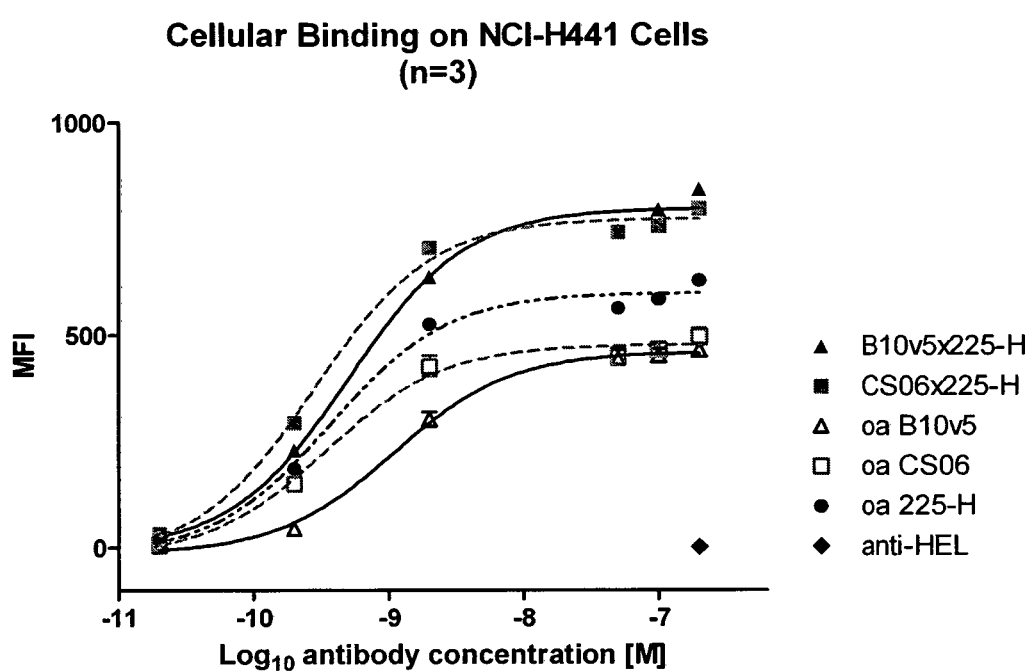
FIG. 1: Depicted is the cellular binding on NCI-H441 cells of two heterodimeric bispecific immunoglobulin molecules of the invention (B10v5x225-H; CS06x225-H) and "one-armed" (oa) heterodimeric immunoglobulin molecules. Anti-HEL: anti-hen egg lysozyme (isotype control).

| SEQUENCE LISTING | |
|---|---|
| SEQ ID NO: 1 | AG-SEED |
| SEQ ID NO: 2 | AG-SEED |
| SEQ ID NO: 3 | GA-SEED |
| SEQ ID NO: 4 | GA-SEED |
| SEQ ID NO: 5 | AG-SEED |
| SEQ ID NO: 6 | GA-SEED |
| SEQ ID NO: 7 | AG-SEED |
| SEQ ID NO: 8 | GA-SEED |
| SEQ ID NO: 9 | humanized C225 VL sequence |
| SEQ ID NO: 10 | humanized C225 VL kinetic variants |
| SEQ ID NO: 11 | humanized C225 VH sequence |
| SEQ ID NO: 12 | humanized C225 VH kinetic variants |
| SEQ ID NO: 13 | humanized C425 VL sequence |
| SEQ ID NO: 14 | humanized C425 VH sequence |
| SEQ ID NO: 15 | c-MET binder A12 VL sequence |
| SEQ ID NO: 16 | c-MET binder A12 VH sequence |
| SEQ ID NO: 17 | c-Met binder B10 VL sequence |
| SEQ ID NO: 18 | c-MET binder B10 VH sequence |
| SEQ ID NO: 19 | c-MET binder C10 VL sequence |
| SEQ ID NO: 20 | c-MET binder C10 VH sequence |
| SEQ ID NO: 21 | c-MET binder E07 VL sequence |
| SEQ ID NO: 22 | c-MET binder E07 VH sequence |
| SEQ ID NO: 23 | c-MET binder G02 VL sequence |
| SEQ ID NO: 24 | c-MET binder G02 VH sequence |
| SEQ ID NO: 25 | c-MET binder H06 VL sequence |
| SEQ ID NO: 26 | c-MET binder H06 VH sequence |
| SEQ ID NO: 27 | c-MET binder F03 VL sequence |
| SEQ ID NO: 28 | c-MET binder F03 VH sequence |
| SEQ ID NO: 29 | c-MET Binder F06 VL sequence |
| SEQ ID NO: 30 | c-MET binder F06 VH sequence |
| SEQ ID NO: 31 | c-MET binder B10v5 VL sequence |
| SEQ ID NO: 32 | c-MET binder B10v5 VH sequence |
| SEQ ID NO: 33 | c-MET binder CS06 VL sequence |
| SEQ ID NO: 34 | c-MET binder CS06 VH sequence |
| SEQ ID NO: 35 | glycine-serine linker |
| SEQ ID NO: 36 | hinge 1 |
| SEQ ID NO: 37 | hinge 2 |
| SEQ ID NO: 38 | CL sequence |
| SEQ ID NO: 39 | CH1 sequence |
| SEQ ID NO: 40 | CH2 domain |
| SEQ ID NO: 41 | CH3 domain (AG) |
| SEQ ID NO: 42 | CH3 domain (GA) |
| SEQ ID NO: 43 | humanized C225 VH S58R kinetic variant (hu225-L) |
| SEQ ID NO: 44 | humanized C225 VL N108Y kinetic variant (hu225-M) |
| SEQ ID NO: 45 | humanized C225 VH T109D kinetic variant (hu225-H) |
| SEQ ID NO 46 | humanized C225 VL N109E, T116N kinetic variant (hu225-H) |
| SEQ ID NO: 47 | c-Met binder B10 VL variants comprising single or multiple amino acid substitutions |
| SEQ ID NO: 48 | c-MET binder B10 VH kinetic variant Q6E (IMGT numbering) |
| SEQ ID NO: 49 | c-Met binder F06 VL sequence variants comprising single or multiple amino acid substitutions |
| SEQ ID NO: 50 | c-Met binder F06 VH variants comprising single or multiple amino acid substitutions |
| SEQ ID NO: 51 | c-Met binder B10v5 VL variants comprising single or multiple amino acid substitutions |
| SEQ ID NO: 52 | c-Met binder CS06 VH kinetic variants |

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The described objectives are solved by the present invention, preferably by the subject matter of the appended claims. The inventors have surprisingly found that heterodimeric bispecific immunoglobulin molecules according to the invention can be used to overcome the resistance to EGFR- or c-MET-targeted monotherapies. In addition, the inventive heterodimeric bispecific immunoglobulin molecules have surprisingly been found to bind cells which express one of EGFR or c-MET with a lower abundance with high selectivity.

The described objective is solved according to a first embodiment by the inventive heterodimeric bispecific immunoglobulin molecule which comprises (i) a first Fab or scFv fragment which specifically binds to EGFR, and
(ii) a second Fab or scFv fragment which specifically binds to c-MET, and
(iii) an antibody hinge region, an antibody CH2 domain and an antibody CH3 domain comprising a hybrid protein-protein interaction interface domain wherein each of said interaction interface domain is formed by amino acid segments of the CH3 domain of a first member and amino acid segments of the CH3 domain of said second member, wherein said protein-protein interface domain of the first chain is interacting with the protein-protein-interface of the second chain by homodimerization of the corresponding amino acid segments of the same member of the immunoglobulin superfamily within said interaction domains, wherein the first or second engineered immunoglobulin chain has the polypeptide sequence ("AG-SEED"): GQP-FRPEVHLLPPSREEMTKNQVSLTCLARGFYPX$_1$DIA-VEWESNGQPENNYKTTPSRQEP SQGTTTFAVTSK-LTX$_2$DKSRWQQGNVFSCSVMHEALHNHYTQKX$_3$ISL (SEQ ID NO:1), wherein X$_1$, X$_2$ and X$_3$ may be any amino acid. For example, amino acids represented by X$_1$, X$_2$ and X$_3$ may each independently from each other be selected from the group of naturally occurring amino acids. Engineered immunoglobulin chains which are comprised in the inventive heterodimeric bispecific immunoglobulin molecule and the respective sequences thereof have been described in WO 2007/110205. In the inventive heterodimeric bispecific immunoglobulin molecule the term heterodimeric.

A "heteromultimeric protein" according to the invention is a protein molecule comprising at least a first subunit and a second subunit, whereby each subunit contains a nonidentical domain. The inventive heterodimeric bispecific immunoglobulin molecule comprises two non-identical protein domains, e.g. "AG-SEED" and "GA-SEED" which will result in a heterodimerization of the non-identical protein domains in a ratio of 1:1. The inventive heterodimeric bispecific immunoglobulin molecule according to a first embodiment comprises a first Fab or scFv fragment which specifically binds to EGFR. The term Fab fragment refers to an antigen binding antibody fragment which can e.g. be obtained by papain treatment of IgG type immunoglobulins, which will result in two Fab fragment and an Fc domain. Functional aspects and pmthods to obtain Fab fragments are described e.g. in "Applications and Engineering of Monoclonal Antibodies" by D. J. King, CRC Press, 1998, chapter 2.4.1; Zaho et al. Protein Expression and Purification 67 (2009) 182-189; S. M. Andrew, J. A. Titus, Fragmentation of immunoglobulin G, Curr. Protoc. Cell Biol. (2003) Unit 16.14 (Chapter 16). The inventive heterodimeric bispecific immunoglobulin molecule may e.g. also comprise a first scFv fragment that specifically binds to EGFR. The term "scFv" as used in the present invention refers to a molecule comprising an antibody heavy chain variable domain (or region; VH) and an antibody light chain variable domain (or region; VL) connected by a linker, and lacks constant domains, e.g. an scFv fragment according to the invention may e.g. include binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an linker interposed between the VH domain and the VL domain, which may e.g. include a peptide sequence comprised of the amino acids glycine and serine. For example, the peptide sequence may comprise the amino acid sequence (Gly$_4$ Ser)$_n$, whereby n is an integer from 1-6, e.g. n may be 1, 2, 3, 4, 5, or 6, preferably n=4. scFv molecules and methods of obtaining them are known in the art and are described, e.g., in U.S. Pat. No. 5,892,019, Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837.

A first Fab or scFv fragment of the inventive heterodimeric bispecific immunoglobulin molecule specifically binds to human epidermal growth factor receptor (EGFR). Specific binding, or any grammatical variant thereof, refers to a binding of the first Fab or scFv fragement with an Kd of at least $1\times10^{-6}$ M, e.g. $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ to EGFR. EGFR according to the invention refers to EGFR having the sequences as provided by UniProtKB database entry P00533, including all of its isoforms and sequence variants (UniProtKB database entries P00533-1, P00533-2, P00533-3, P00533-4), or any of the mutations described in Cai et al., PLoS ONE 9(4): e95228, such as e.g. c.2126A>C, c.2155G>T, c.2156G>C, c.2235_2249 del15, c.2236_2250 del15, c.2237_2251 del, c.2239_2248 ATTAAGAGGAG>C, c.2240_2257 del18, c2248G>C, c.2303G>T, c.2573T>G, c.2582T>A, p745del_frameshift, p.L858R, p.S768I.

The inventive heterodimeric bispecific immunoglobulin molecule further comprises a second Fab or scFv fragment which specifically binds to c-MET. c-MET as used herein refers to MET Proto-Oncogene, Receptor Tyrosine Kinase (UniProtKB database antry P08581), which may also be referred to as Hepatocyte Growth Factor Receptor. For example, c-MET also includes sequence variants such as those disclosed in Nat Genet. 1997 May; 16(1):68-73, e.g. c-MET R970C (MET$^{R970C}$), c-MET T992I (MET$^{T992I}$), MET$^{M1149T}$, MET$^{V1206L}$, MET$^{V1238I}$, MET$^{D1246N}$, MET$^{Y1248C}$, MET$^{L1213V}$, MET$^{D1246H}$, MET$^{Y1248H}$, MET$^{M1268T}$, MET$^{A320V}$, MET$^{N375S}$. Specific binding of the second Fab or scFv fragment to c-MET refers to a binding of the second Fab or scFv fragment with an K$_d$ of at least $1\times10^{-6}$ M, e.g. $1\times10^{-6}$ M, $1\times10^{-7}$ M, $1\times10^{-8}$ M, $1\times10^{-9}$ M, $1\times10^{-10}$ M, $1\times10^{-11}$M, $1\times10^{-12}$ to c-MET.

The inventive heterodimeric bispecific immunoglobulin molecule according to a first embodiment of the invention further comprises antibody hinge region, an antibody CH2 domain and an antibody CH3. For example, there are five classes of immunoglobulins (IgA, IgD, IgE, IgG, and IgM) all of which contain a hinge region and which may be comprised in the inventive heterodimeric bispecific immunoglobulin molecule. Additionally, some of these classes of immunoglobulins have subclasses, e.g., IgG has four subclasses (IgG1, IgG2, IgG3, and IgG4). (Alberts, B. et al., Chapter 23: The Immune System, In Molecular Biology of the Cell, 3d Edition, Garland Publishing, Inc., New York, N.Y.), the hinge regions of which may also be comprised in the heterodimeric bispecific immunoglobulin molecule of the invention. The hinge region may e.g. be divided into three regions: the upper, middle, and lower hinge. The upper hinge is defined as the number of amino acids between the end of the first domain of the heavy chain (CH1) and the first cysteine forming an inter heavy chain disulfide bridge. The middle hinge is high in proline and contains the inter-heavy chain cysteine disulfide bridges. The lower hinge connects the middle hinge to the CH2 domain (see e.g. Sandlie, I. and Michaelsen, T., Chapter 3: Engineering the Hinge Region to Optimize Complement-induced Cytolysis, In Antibody Engineering: A Practical Guide, W. H. Freeman and Co., New York, N.Y.; Hamers-Casterman, C., Naturally Occurring Antibodies Devoid of Light Chains, 363 Nature 446 (1993) and Terskikh, A. V., "Peptabody": A New Type of High Avidity Binding Protein, 94 Proc. Natl. Acad. Sci. USA 1663 (1997)). The hinge region of the inventive inventive heterodimeric bispecific immunoglobulin molecule may e.g. also comprise any of the amino acid sequences of the hinge regions disclosed in J. of Biological Chem. VOL. 280, NO. 50, pp. 41494-41503, Dec. 16, 2005.

In one embodiment, the heterodimeric bispecific immunoglobulin molecule of the invention comprises as first member IgG of the immunoglobulin super family and as second member IgA. For example, the inventive heterodimeric bispecific immunoglobulin molecule may in one embodiment comprise the hinge region according to the amino acid sequence of SEQ ID NO: 1, or SEQ ID NO: 2. For example, the inventive heterodimeric bispecific immunoglobulin molecule may comprise derivatives of human IgG and IgA CH3 domains which create complementary human strand-exchange engineered domain (SEED) CH3 heterodimers that are composed of alternating segments of human IgA and IgG CH3 sequences as described in Protein Engineering, Design & Selection vol. 23 no. 4 pp. 195-202, 2010; or WO 2007/110205 A1). The resulting pair of SEED CH3 domains preferentially associates to form heterodimers when expressed in mammalian cells. SEEDbody (Sb) fusion proteins consist of [IgG1 hinge]-CH2-[SEED CH3].

In one embodiment the heterodimeric bispecific immunoglobulin molecule of the invention as disclosed above comprises a first or second engineered immunoglobulin chain ("AG-SEED") which has the polypeptide sequence according to SEQ ID NO:2 in which $X_1$ is K or S, $X_2$ is V or T, and $X_3$ is T or S. For example, the first or second engineered immunoglobulin chain of the of the inventive heterodimeric bispecific immunoglobulin molecule may comprise an amino acid sequence according to SEQ ID NO: 2 in which $X_1$ is K, $X_2$ is V, and $X_3$ is S, $X_1$ is K, $X_2$ is V, and $X_3$ is T, $X_1$ is K, $X_2$ is T, and $X_3$ is S, $X_1$ is K, $X_2$ is T, and $X_3$ is T, $X_1$ is S, $X_2$ is V, and $X_3$ is S, $X_1$ is 5, $X_2$ is V, and $X_3$ is T, $X_1$ is S, $X_2$ is T, and $X_3$ is S, or $X_1$ is S, $X_2$ is T, and $X_3$ is T.

In one embodiment the inventive heterodimeric bispecific immunoglobulin molecule as disclosed above comprises a first or second engineered immunoglobulin chain which has the polypeptide sequence according to SEQ ID NO: 3 ("GA-SEED"), whereby wherein $X_1$, $X_2$, $X_3$, $X_4$, $X_5$ and $X_6$ may be any amino acid, e.g. $X_1$, $X_2$, $X_3$, $X_4$, $X_5$, $X_6$ may be independently selected from alanine, arginine, asparagine, aspartic acid, asparagine or aspartic acid, cysteine, glutamic acid, glutamine, glycine, histidine, isoleucine, leucine, lysine, methionine, phenylalanine, proline, serine, threonine, tryptophan, tyrosine, or valine. According to a one embodiment, the first or second engineered immunoglobulin chain of the inventive heterodimeric bispecific immunoglobulin molecule as disclosed above has the amino acid sequence according to SEQ ID NO:3, wherein $X_1$ is L or Q, $X_2$ is A or T, $X_3$ is L, V, D or T; $X_4$ is F, A, D, E, G, H, K, N, P, Q, R, S or T; $X_5$ is A or T, and $X_6$ is E or D. In a preferred embodiment, the first engineered immunoglobulin chain comprises the amino acid sequence according to SEQ ID NO: 5 ("AG-SEED") and the second engineered immunoglobulin chain of the inventive heterodimeric bispecific immunoglobulin molecule as disclosed above comprises the amino acid sequence according to SEQ ID NO: 6 ("GA-SEED").

In one embodiment the inventive heterodimeric bispecific immunoglobulin molecule binds to EGFR as disclosed above with an affinity of at least $K_D=5\times10^{-8}$M, $1\times10^{-9}$ M, $1\times10^{-10}$ M, $1\times10^{-11}$M, $1\times10^{-12}$ to EGFR. According to one embodiment the inventive heterodimeric bispecific immunoglobulin molecule binds to c-MET as disclosed above with an affinity of at least $K_D=5\times10^{-8}$M, $1\times10^{-9}$ M, $1\times10^{-10}$ M, $1\times10^{-11}$M, $1\times10^{12}$ to c-MET. For example, the heterodimeric bispecific immunoglobulin molecule of the invention as disclosed above binds via a first and second Fab or scFv fragment c-MET and EGFR with an affinity of $K_D=5\times10^{-8}$M, $1\times10^{-9}$ M, $1\times10^{-10}$ M, $1\times10^{-11}$ M, $1\times10^{-12}$ M. EGFR and c-Met may e.g. be present on a single cell, such as a cancer cell, or e.g. to a cell, such as e.g. cancer cell, which may be single cell, a plurality of cells, or tumor tissue that expresses both c-MET and EGFR. The cells may, e.g. also be in suspension, or detached from tissue and may circulate in the blood stream of an individual, such as a human inflicted with cancer. For example, the affinity of first and second Fab and/or scFv fragments of the inventive heterodimeric bispecific immunoglobulin molecule may be determined by ELISA, or surface plasmon resonance as described in J. Biochem. Biophys. Methods 57 (2003) 213-236, Current Protocols in Protein Science (2006) 19.14.1-19.14.17.

According to one embodiment the first Fab or scFv fragment of the heterodimeric bispecific immunoglobulin molecule of the invention as disclosed above is derived from cetuximab (C225). For example, the first Fab or scFv fragment of the heterodimeric bispecific immunoglobulin molecule may comprise VL and VH sequences of cetuximab, or e.g. VL and VH sequences of cetuximab which have been humanized. For example, humanized as used for the inventive heterodimeric bispecific immunoglobulin molecule refers to a chimeric antibody or antibody fragment which contain minimal sequence derived from non-human immunoglobulin. Humanization of a given antibody sequence will result in a reduction of the immunogenicity of a xenogenic antibody, such as a murine antibody, or chimeric antibody which already comprises human sequences, for introduction into a human, while maintaining the full antigen binding affinity and specificity of the antibody. For example, cetuximab is a chimeric antibody which is composed of the Fv (variable; antigen-binding) regions of the 225 murine EGFR monoclonal antibody specific for the N-terminal portion of human EGFR with human IgG1 heavy and kappa light chain constant (framework) regions.

Humanization may e.g. comprise CDR grafting technology which involves substituting the complementarity determining regions of, for example, a mouse antibody, into a human framework domain, e.g., see WO 92/22653. Strategies and methods for the resurfacing of antibodies, and other methods for reducing immunogenicity of antibodies within a different host, are disclosed in U.S. Pat. No. 5,639,641. Antibodies can be humanized using a variety of other techniques including CDR-grafting (see e.g. EP 0 239 400 B1; WO 91/09967; U.S. Pat. Nos. 5,530,101; 5,585,089), veneering or resurfacing (see e.g. EP 0 592 106; EP 0 519 596; Padlan E. A., 1991, Molecular Immunology 28(4/5): 489-498; Studnicka G. M. et al., 1994, Protein Engineering, 7(6): 805-814; Roguska M. A. et al., 1994, PNAS, 91: 969-973), chain shuffling (see e.g. U.S. Pat. No. 5,565,332), and identification of flexible residues (see e.g. WO2009032661). Human antibodies can be made by a variety of methods known in the art including phage display methods, such as. g. U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, WO 91/10741. Accordingly, the first Fab or scFv fragment of the heterodimeric bispecific immunoglobulin molecule of the invention as disclosed above may comprise VL and VH sequences according to to any one of SEQ ID NO: 9, SEQ ID NO:10, SEQ ID NO: 11, SEQ ID NO: 12, SEQ ID NO: 43, SEQ ID NO: 44, SEQ ID NO: 45, SEQ ID NO: 46. For example, the VL amino acid sequence of first Fab or scFv fragment of the heterodimeric bispecific immunoglobulin molecule may comprise the amino acid sequence according to SEQ ID NO: 9, SEQ ID NO: 10, SEQ ID NO: 44, SEQ ID NO: 46 and VH amino acid sequences selected from SEQ ID NO: 43, SEQ ID NO: 45, SEQ ID NO: 11, SEQ ID NO: 12. VL and VH sequences of the first Fab or scFv fragment as disclosed above may e.g. comprise SEQ ID NO:43 and SEQ ID NO: 9, SEQ ID NO: 44 and SEQ ID NO: 9, or SEQ ID NO: 45 and SEQ ID NO: 9, or e.g. SEQ ID NO: 43 and SEQ ID NO: 9, or SEQ ID NO:45 and SEQ ID NO: 9, or SEQ ID NO: 46 and SEQ ID NO: 11.

According to one embodiment the second Fab or scFv fragment of the inventive heterodimeric bispecific immunoglobulin molecule has disclosed above comprises VL sequences selected from the group consisting of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 47, SEQ ID NO: 49, SEQ ID NO: 51.

In one embodiment the second Fab or scFv fragment of the inventive heterodimeric bispecific immunoglobulin molecule has disclosed above comprises VH sequences selected from the group consisting of SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO:34, SEQ ID NO: 48, SEQ ID NO: 50, or SEQ ID NO: 52.

According to one embodiment, the first and second Fab or scFv fragments of the heterodimeric bispecific immunoglobulin molecule of the invention as disclosed above comprise the amino acid sequences selected from SEQ ID NO: 9, SEQ ID NO: 43, SEQ ID NO: 17, SEQ ID NO:18, or SEQ ID NO: 47, SEQ ID NO: 48 (e.g. which may be comprised in the inventive molecule "225-LxB10"), or SEQ ID NO: 11, SEQ ID NO: 44, SEQ ID NO: 31, SEQ ID NO: 51, SEQ ID NO:32 (e.g. which may be comprised in the inventive molecule "225-MxB10v5"), or SEQ ID NO:45, SEQ ID NO: 46, SEQ ID NO: 29, SEQ ID NO: 49, SEQ ID NO: 30, SEQ ID NO: 50, (e.g. which may be comprised in the inventive molecule "225-HxF06"), or SEQ ID NO: 45, SEQ ID NO: 46, SEQ ID NO: 33, SEQ ID NO: 34, SEQ ID NO: 52 (e.g. which may be comprised in the inventive molecule "225-HxCS06"), or SEQ ID NO: 11, SEQ ID NO: 44, SEQ ID NO: 33, SEQ ID NO: 34, SEQ ID NO: 52 (e.g. which may be comprised in the inventive molecule "225-MxCS06").

According to one embodiment the first and second Fab or scFv fragments of the heterodimeric bispecific immunoglobulin molecule of the invention as disclosed above comprise the amino acid sequences according to SEQ ID NO: 11, SEQ ID NO: 44, SEQ ID NO: 33, SEQ ID NO: 34, SEQ ID NO: 52 (e.g. corresponding to the inventive molecule "225-MxCS06"), or SEQ ID NO:45, SEQ ID NO: 46, SEQ ID NO: 29, SEQ ID NO: 49, SEQ ID NO: 30, SEQ ID NO: 50 (e.g. corresponding to the inventive molecule "225-HxCS06").

In one embodiment the inventive the Fc domain of the heterodimeric bispecific immunoglobulin molecule interacts with the neonatal Fc receptor (FcRn). FcRn is a major histocompatibility complex class I-like heterodimer composed of the soluble light chain β2-microglobulin (β2m) and a membrane-bound heavy chain. Crystal structure analysis revealed that the human FcRn (hFcRn) binds to the CH2-CH3 hinge region of both heavy chains of the Fc homodimer of an IgG, resulting in a 2:1 stoichiometry. The interaction between FcRn and Fc is mainly stabilized by salt bridges between anionic FcRn residues and histidine residues of the IgG, which are protonated at acidic pH. Site-directed mutagenesis studies and crystal structure analysis of the FcRn/IgG Fc complex show that the Fc amino acid residues at positions 252-256 in the CH2 domains and at 310, 433, 434, and 435 in the CH3 domains are at the core or in close proximity to the FcRn interaction site, and that the conserved histidine residues H310 and possibly H435 are responsible for the pH dependence (see e.g. mAbs 6:4, 928-942; July/August 2014; Nature Reviews Immunology 7, 715-725 (September 2007)). For example, the inventive heterodimeric bispecific immunoglobulin molecule may interact with the FcRn via salt bridges as disclosed above, or may interact with FcRn by salt bridges that involve other amino acids of both AG-SEED and GA-SEED, thereby protecting the inventive heterodimeric bispecific immunoglobulin molecule from degradation and extending its serum half-life. Extended half-life of the inventive heterodimeric bispecific immunoglobulin molecule may e.g. be employed to minimize adverse reactions caused by high doses of the inventive heterodimeric bispecific immunoglobulin molecule if administered to an individual e.g. by i.v. or i.m. application, which will e.g. also result in a decreased frequency of injection of the inventive heterodimeric bispecific immunoglobulin molecule. This will e.g. also reduce the financial burden on an individual which may be in need of a treatment with the inventive heterodimeric bispecific immunoglobulin molecule. For example, sequence variants of the AG-SEED and GA-SEED may be used to reduce the interaction of the inventive heterodimeric bispecific immunoglobulin molecule with FcRn thereby shortening its serum half-life. Sequence variants e.g. include those disclosed above, AG-SEED with $X_1$, $X_2$ and $X_3$ representing any amino acid, or e.g. preferably an AG-SEED in which $X_1$ is K or S, $X_2$ is V or T, and $X_3$ is T or S, or e.g. a GA-SEED as disclosed above wherein $X_1$, $X_2$, $X_3$, $X_4$, $X_5$ and $X_6$ may be any amino acid. It may e.g. be preferred that in the GA-SEED $X_1$ is L or Q, $X_2$ is A or T, $X_3$ is L, V, D or T; $X_4$ is F, A, D, E, G, H, K, N, P, Q, R, S or T; $X_5$ is A or T, and $X_6$ is E or D.

In one embodiment, the amino acids of the inventive heterodimeric bispecific immunoglobulin molecule as disclosed above which interact with FcRn are derived from IgG1, preferably human IgG1. For example, the amino acids which interact with FcRn comprise those of wildtype IgG1 as disclosed above, e.g. Fc amino acid residues at positions 252-256 in the CH2 domains and at 310, 433, 434, and 435 in the CH3 domains are at the core or in close proximity to the FcRn interaction site, whereby the conserved histidine residues H310 and possibly H435 may e.g. confer for the pH dependence of the interaction between the inventive heterodimeric immunoglobulin molecule and FcRn.

In one embodiment the inventive heterodimeric bispecific immunoglobulin molecule as disclosed above mediates antibody-dependent cellular cytotoxicity. For example, the inventive heterodimeric bispecific immunoglobulin molecule induces ADCC when bound to EGFR and c-MET expressed on the surface of the same cell cell, or e.g. when bound to two cells, one of which expresses EGFR and the second one of which expresses c-MET, whereby e.g. EGFR and c-Met are as defined above. Binding of the heterodimeric bispecific immunoglobulin molecule of the invention to EGFR and c-Met present on the same cell or on two individual cells, but preferably one the same cell, is as disclosed above. The term ADCC (antibody dependent cell cytotoxicity) as used for the inventive heterodimeric bispecific immunoglobulin molecule refers to a mechanism of cell-mediated immune defense whereby an effector cell of the immune system actively lyses a target cell, whose membrane-surface antigens have been bound by specific antibodies. ADCC is mediated by e.g. the binding of CD16 (FcγRIII) expressed on NK cells to the Fc domain of antibodies (see e.g. Clynes et al. (2000) Nature Medicine 6, 443-446). ADCC may e.g. be improved by amino acid substitutions in the Fc domain which affect the binding of the Fc domain to CD16. For example, Shields et al. (J Biol Chem 9(2), 6591-6604 (2001)) showed that amino acid substitutions at positions 298, 333, and/or 334 of the Fc region (EU numbering of residues) improve ADCC. Alternatively, increased Fc receptor binding and effector function may e.g. be obtained by altering the glycosylation of the Fc region. The two complex biantennary oligosaccharides attached to Asn 297 of the Fc domain are typically buried between the CH2 domains, forming extensive contacts with the polypeptide backbone, and their presence is essential for the antibody to mediate effector functions including ADCC (Lifely et al., Glycobiology 5, 813-822 (1995); Jefferis et al., Immunol Rev 163, 59-76 (1998); Wright and Morrison, Trends Biotechnol 15, 26-32 (1997)). Overexpression of e.g. β(1,4)-N-acetylglucosaminyltransferase III (GnTIII), a glycosyltransferase catalyzing the formation of bisected oligosaccharides, significantly increases the in vitro ADCC activity of antibodies. Thus overexpression of e.g. of GnTIII in cell lines used for the production of the inventive heterodimeric bispecific immunoglobulin molecule, may result in inventive fusion proteins enriched in bisected oligosaccharides, which are generally also non-fucosylated and may exhibit increased ADCC.

In one embodiment the invention provides an isolated polynucleotide which encodes at least one of the amino acid sequences according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO:17, SEQ ID NO: 18, SEQ ID NO: 19, SEQ ID NO:20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO:40, SEQ ID NO: 41, SEQ ID NO:42, SEQ ID NO:43, SEQ ID NO:44, SEQ ID NO:45, SEQ ID NO:46, SEQ ID NO: 47, SEQ ID NO: 48, SEQ ID NO: 49, SEQ ID NO: 50, SEQ ID NO:51, SEQ ID NO: 52 of the inventive bispecific heterodimeric immunoglobulin molecule. For example, the isolated polynucleotide of the invention may encode at least one, e.g. one, two, three, four, five, six, seven, eight, nine or ten of the amino acid sequences as disclosed above. For example, in one embodiment the isolated polynucleotide comprises polynucleotides which encode at least one of the amino acid sequences according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 31, SEQ ID NO: 32, SEQ ID NO: 33, SEQ ID NO: 34, SEQ ID NO:43, SEQ ID NO:44, SEQ ID NO:45, SEQ ID NO:46, SEQ ID NO: 47, SEQ ID NO: 48, SEQ ID NO: 49, SEQ ID NO: 50, SEQ ID NO:51, SEQ ID NO: 52 of the inventive bispecific heterodimeric immunoglobulin molecule. For example the isolated polynucleotide of the invention may comprise polynucleotides which encode amino acid sequences according to (225M, CS06) SEQ ID NO: 11, SEQ ID NO: 44, SEQ ID NO: 33, SEQ ID NO: 34, SEQ ID NO: 52, or (225H, CS06) SEQ ID NO:45, SEQ ID NO: 46, SEQ ID NO: 29, SEQ ID NO: 49, SEQ ID NO: 30, SEQ ID NO: 50. For example, in one embodiment the isolated polynucleotide according to the invention may e.g. comprise polynucleotides encoding the amino acid sequences according to SEQ ID NO: 31, SEQ ID NO: 32, SEQ ID NO: 43, SEQ ID NO:44, SEQ ID NO:45, SEQ ID NO:46. In one embodiment the polynucleotide according to the invention e.g. comprises polynucleotides which encode the amino according to SEQ ID NO: 31, SEQ ID NO: 32, SEQ ID NO:45, SEQ ID NO:46. For example, in one embodiment the inventive polynucleotide encodes amino acid sequences according to SEQ ID NO: 31, SEQ ID NO: 32, SEQ ID NO:45, SEQ ID NO:46. In one embodiment, the polynucleotide according to the invention comprises polynucleotides which encode the amino acid sequences selected from SEQ ID NO: 9, SEQ ID NO: 43, SEQ ID NO: 17, SEQ ID NO:18, or SEQ ID NO: 47, SEQ ID NO: 48 (e.g. which may be comprised in the inventive molecule "225-LxB10"), or SEQ ID NO: 11, SEQ ID NO: 44, SEQ ID NO: 31, SEQ ID NO: 51, SEQ ID NO:32 (e.g. which may be comprised in the inventive molecule "225-MxB10v5"), or SEQ ID NO:45, SEQ ID NO: 46, SEQ ID NO: 29, SEQ ID NO: 49, SEQ ID NO: 30, SEQ ID NO: 50, (e.g. which may be comprised in the inventive molecule "225-HxF06"), or SEQ ID NO: 45, SEQ ID NO: 46, SEQ ID NO: 33, SEQ ID NO: 34, SEQ ID NO: 52 (e.g. which may be comprised in the inventive molecule "225-HxCS06"), or SEQ ID NO: 11, SEQ ID NO: 44, SEQ ID NO: 33, SEQ ID NO: 34, SEQ ID NO: 52 (e.g. which may be comprised in the inventive molecule "225-MxCS06"), or SEQ ID NO: 11, SEQ ID NO: 44, SEQ ID NO: 33, SEQ ID NO: 34, SEQ ID NO: 52 (e.g. corresponding to the inventive molecule "225-MxCS06"), or SEQ ID NO:45, SEQ ID NO: 46, SEQ ID NO: 29, SEQ ID NO: 49, SEQ ID NO: 30, SEQ ID NO: 50 (e.g. corresponding to the inventive molecule "225-HxCS06"), or (225M, CS06) SEQ ID NO: 11, SEQ ID NO: 44, SEQ ID NO: 33, SEQ ID NO: 34, SEQ ID NO: 52, or (225H, CS06) SEQ ID NO:45, SEQ ID NO: 46, SEQ ID NO: 29, SEQ ID NO: 49, SEQ ID NO: 30, SEQ ID NO: 50, or (e.g. corresponding inventive molecule "225M, B10v5") SEQ ID NO: 11, SEQ ID NO: 44, SEQ ID NO: 31, SEQ ID NO: 51, SEQ ID NO:32, or (e.g. corresponding inventive molecule "225H, CS06") SEQ ID NO:45, SEQ ID NO: 46, SEQ ID NO: 29, SEQ ID NO: 49, SEQ ID NO: 30, SEQ ID NO: 50. For example, the nucleotide sequence of each of the above amino acid sequences of the invention may be obtained by translation using web-based tools, such as "Translate tool" (http://web.expasy.org/translate/) and may e.g. be codon-optimized accordance with the intended expression system or host (see e.g. Trends Mol Med. 2014 November; 20(11):604-13; Genome Res. 2007 April; 17(4): 401-4). For example, the polynucleotides encoding the amino acid sequences as disclosed above may be comprised on individual polynucleotides, each of which is considered a polynucleotide according to the invention, or e.g. the polynucleotide according to the invention may comprise polynucleotides encoding two of the amino acid sequences as disclosed above e.g. SEQ ID NO: 31, SEQ ID NO: 32, or SEQ ID NO: 33, SEQ ID NO: 34, or SEQ ID NO:45, SEQ ID NO:46, or SEQ ID NO: 29, SEQ ID NO: 30, or SEQ ID NO: 11, SEQ ID NO: 9, or SEQ ID NO 49, SEQ ID NO: 50.

The polynucleotides according to the invention as disclosed above may e.g. be used for the production of the inventive bispecific heterodimeric immunoglobulin molecule, e.g. by heterologous expression in a suitable host, or host cell.

The term "isolated" as used with the polynucleotides according to the invention refers to polynucleotides which are separated from e.g. constituents, cellular and otherwise, in which the polynucleotide are normally associated with in nature, e.g. the isolated polynucleotide is at least 80%, 90%, 95% pure by weight, i.e. devoid of contaminating constituents. For example, isolated polynucleotides of the invention may refer to a DNA molecule that is separated from sequences with which it is immediately contiguous (in the 5' and 3' directions) in the naturally occurring genome of the organism from which it was derived. For example, the "isolated polynucleotide" may comprise a DNA molecule inserted into a vector, such as a plasmid or virus vector, or integrated into the genomic DNA of a procaryote or eucaryote.

In one embodiment the present invention provides a vector which comprises at least one polynucleotide according to the invention as disclosed above. The term vector or expression vector according to the invention refers to a nucleic acid molecule capable of extra-chromosomal replication. Preferred vectors are those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. Nucleic acid sequences necessary for expression of the heterodimeric bispecific immunoglobulin molecule in eukaryotic cells comprise e.g. at least one promoter, and enhancers, termination and polyadenylation signals as well as a selectable marker, such as e.g. an antibiotic resistance. Expression vectors which may be used for expression of the inventive heterodimeric bispecific immunoglobulin molecule may e.g. comprise pCMV, pcDNA, p4X3, p4X4, p4X5, p4X6, pVL1392, pVL1393, pACYC177, PRS420, or if viral based vector systems are to be used e.g. pBABEpuro, pWPXL, pXP-derived vectors, may e.g. comprise pCMV, pcDNA, p4X3, p4X4, p4X5, p4X6, pVL1392, pVL1393, pACYC177, PRS420, or if viral based vector systems are to be used e.g. pBABEpuro, pWPXL, pXP-derived vectors.

In one embodiment, the present invention provides a host cell which comprises the polynucleotide sequence or vector as disclosed above, e.g. a polynucleotide or vector or expression vector which comprises at least one coding sequence for the inventive heterodimeric bispecific immunoglobulin molecule as disclosed above. For example, a host cell for use in the invention may be a yeast cell, insect cell or mammalian cell. For example, the host cell of the invention may be an insect cell selected from Sf9, Sf21, S2, Hi5, or BTI-TN-5B1-4 cells, or e.g. the host cell of the invention may be a yeast cell selected from *Saccharomyces cerevisiae*, *Hansenula polymorpha*, *Schizosaccharomyces pombe*, *Schwanniomyces occidentalis*, *Kluyveromyceslactis*, *Yarrowia lipolytica* and *Pichia pastoris*, or e.g. the host cell of the invention may be a mammalian cell selected from HEK293, HEK293T, HEK293E, HEK 293F, NSO, per.C6, MCF-7, HeLa, Cos-1, Cos-7, PC-12, 3T3, Vero, vero-76, PC3, U87, SAOS-2, LNCAP, DU145, A431, A549, B35, H1299, HUVEC, Jurkat, MDA-MB-231, MDA-MB-468, MDA-MB-435, Caco-2, CHO, CHO-K1, CHO-B11, CHO-DG44, BHK, AGE1.HN, Namalwa, WI-38, MRC-5, HepG2, L-929, RAB-9, SIRC, RK13, 11B11, 1D3, 2.4G2, A-10, B-35, C-6, F4/80, IEC-18, L2, MH1C1, NRK, NRK-49F, NRK-52E, RMC, CV-1, BT, MDBK, CPAE, MDCK.1, MDCK.2, and D-17.

In one embodiment the invention provides a method for producing the heterodimeric bispecific immunoglobulin molecule of the invention as disclosed above, whereby the inventive method comprises the steps of culturing a host cell according to the invention as disclosed above under conditions sufficient for the heterologous expression of said heterodimeric bispecific immunoglobulin molecule and purifying said heterodimeric bispecific immunoglobulin molecule. For example, host cells of the invention may be allowed to grow in DMEM containing 10% FBS, and were incubated at 37° C. in 10% $CO_2$, or e.g. in protein-free culture medium to aid in the subsequent isolation and purification, or e.g. in Grace's insect medium, express Five® SFM (Life Technologies), or High Five® medium (Life Technologies), YNM medium, YPD broth, or e.g. PichiaPink (Life technologies). For example, expression of the inventive heterodimeric bispecific immunoglobulin molecule in mammalian cells may be done according to the method as described in Methods Mol Biol. 2012; 907:341-58. Insect cells may e.g. also be used for the expression of the inventive heterodimeric bispecific immunoglobulin molecule such as e.g. *Drosophila* S2 cells as described in Journal of Immunological Methods 318 (2007) 37-46. Yeast cells, for example, may also be used for the expression of the inventive heterodimeric bispecific immunoglobulin molecule, such as *Pichia pastoris* as described in Appl Microbiol Biotechnol. 2014 December; 98(24):10023-39, or Biotechnol Lett. 2015 July; 37(7):1347-54.

The host cells of the invention may e.g. be allowed to grow between 12-408 h, e.g. for about 12 to about 400 h, e.g. between 14 h, 16 h, 18 h, 20 h, 24 h, 36 h, 48 h, 72 h, 96 h to about 120 h, 144 h, 168 h, 192, 216 h, 240 h, 264 h, 288 h, 312 h, 336 h, 360 h, 384 h, 408 h. Subsequently, the inventive vNAR or inventive fusion protein may be isolated and purified. For example, the heterodimeric bispecific immunoglobulin molecule of the invention may be purified and isolated by chromatography, e.g. ion-exchange chromatography, size-exclusion chromatography, ammonium sulfate precipitation, or ultrafiltration. For example, the inventive heterodimeric bispecific immunoglobulin molecule may also comprise a signal sequence, which refers to an amino acid sequence which is capable of initiating the passage of a polypeptide, to which it is operably linked, e.g. by a peptide bond, into the endoplasmic reticulum (ER) of a host cell. The signal peptide is generally cleaved off by an endopeptidase (e.g. a specific ER-located signal peptidase) to release the (mature) polypeptide. The length of a signal peptide is typically in the range from about 10 to about 40 amino acids.

In one embodiment the invention provides a heterodimeric bispecific immunoglobulin molecule according to the invention as disclosed above which is obtainable by the inventive method as disclosed above. For example, the heterodimeric bispecific immunoglobulin molecule of the invention as disclosed above may be produced by the inventive method as disclosed above and isolated.

In one embodiment the heterodimeric bispecific immunoglobulin molecule of the invention as disclosed above is covalently coupled to at least one linker. The term "linker" or "linker peptide" refers to a synthetic or artificial amino acid sequence that connects or links two molecules, such as e.g. two polypeptide sequences that link two polypeptide domains, or e.g. a protein and a cytostatic drug, or toxin. The term "synthetic" or "artificial" as used in the present invention refers to amino acid sequences that are not naturally occurring. The linker which is covalently bound to the heterodimeric bispecific immunoglobulin molecule of the invention is cleavable or non-cleavable. The term "cleavable" as used in the present invention refers to linkers which may be cleaved by proteases, acids, or by reduction of a disulfide body (e.g. glutathion-mediated or glutathion sensitive). For example, cleavable linkers may comprise valine-citrulline linkers, hydrazone linkers, or disulfide linkers. Non-cleavable linkers which may e.g. be covalently bound to the amino donor-comprising substrate of the invention comprise maleimidocaproyl linker to MMAF (mc-MMAF), N-maleimidomethylcyclohexane-1-carboxylate (MCC), or mercapto-acetamidocaproyl linkers. For example, the linkers which are covalently coupled to the inventive heterodimeric bispecific immunoglobulin molecule may also include linkers as described in WO 2010/138719, or e.g. those described in WO 2014/093379.

In one embodiment the linker of the heterodimeric bispecific immunoglobulin molecule of the invention as disclosed above is coupled to a dye, radioisotope, or cytotoxin. The term "coupled" as used for the linker as disclosed above refers to the fact that the dye, radioisotope or cytoxin may e.g. be non-covalently via e.g. ionic, or hydrophobic interactions, or covalently attached to the linker molecule as disclosed above. For example, the linker may comprise streptavidin and the dye, radioisotope or cytotoxin may be covalently bound to biotin. For example, the dye which may be covalently linked or coupled to the inventive heterodimeric bispecific immunoglobulin molecule may also be a fluorophore, such as e.g. 1,8-ANS, 4-methylumbelliferone, 7-amino-4-methylcoumarin, 7-hydroxy-4-methylcoumarin, Acridine, Alexa Fluor 350™, Alexa Fluor 405™, AMCA, AMCA-X, ATTO Rho6G, ATTO Rho11, ATTO Rho12, ATTO Rho13, ATTO Rho14, ATTO Rho101, Pacific Blue, Alexa Fluor 430™, Alexa Fluor 480™, Alexa Fluor 488TH, BODIPY 492/515, Alexa Fluor 532™, Alexa Fluor 546™, Alexa Fluor 555™, Alexa Fluor 594™, BODIPY 505/515, Cy2, cyQUANT GR, FITC, Fluo-3, Fluo-4, GFP (EGFP), mHoneydew, Oregon Green™ 488, Oregon Green™ 514, EYFP, DsRed, DsRed2, dTomato, Cy3.5, Phycoerythrin (PE), Rhodamine Red, mTangerine, mStrawberry, mOrange, mBanana, Tetramethylrhodamine (TRITC), R-Phycoerythrin, ROX, DyLight 594, Calcium Crimson, Alexa Fluor 594™, Alexa Fluor 610™, Texas Red, mCherry, mKate, Alexa Fluor 660™, Alexa Fluor 680™ allophycocyanin, DRAQ-5, carboxynaphthofluorescein, C7, DyLight 750, Cellvue NIR780, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxy coumarin, Naphtho fluorescein, PyMPO, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, HEX, 6-JOE, NBD (7-nitrobenz-2-oxa-1, 3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, or La Jolla blue dye. Dyes which may be used in the invention may e.g. also include quantum dots. The term quantum dot as used in the present invention refers to a single spherical nanocrystal of semiconductor material where the radius of the nanocrystal is less than or equal to the size of the exciton Bohr radius for that semiconductor material (the value for the exciton Bohr radius can be calculated from data found in handbooks containing information on semiconductor properties, such as the CRC Handbook of Chemistry and Physics, 83rd ed., Lide, David R. (Editor), CRC Press, Boca Raton, Fla. (2002)). Quantum dots are known in the art, as they are described in references, such as Weller, Angew. Chem. Int. Ed. Engl. 32: 41-53 (1993), Alivisatos, J. Phys. Chem. 100: 13226-13239 (1996), and Alivisatos, Science 271: 933-937 (1996). Quantum dots may e.g. be from about 1 nm to about 1000 nm diameter, e.g. 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm, preferably at least about 2 nm to about 50 nm, more preferably QDs are at least about 2 nm to about 20 nm in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS. Quantum dots may be coupled to the inventive linker, enzyme, or protein by any method known in the art such as e.g. the methods disclosed in Nanotechnology. 2011 Dec. 9; 22(49):494006; Colloids and Surfaces B: Biointerfaces 84 (2011) 360-368. For example, the linker as disclosed above may be covalently bound or coupled to a radioisotope such as e.g. $^{47}$Ca, $^{14}$C, $^{137}$Cs, $^{157}$Cr, $^{57}$Co, $^{60}$Co, $^{67}$Cu, $^{67}$Ga, $^{123}$I, $^{125}$I, $^{129}$I, $^{131}$I, $^{32}$P, $^{75}$Se, $^{85}$Sr, $^{35}$S, $^{201}$Th, $^{3}$H, preferably, the radioisotopes are incorporated into a further molecule, such as e.g. a chelator. Typical chelators that may e.g. be used as a further molecule covalently bound to the amino donor-comprising substrate of the invention are DPTA, EDTA (Ethylenediamine-tetraacetic acid), EGTA (Ethyleneglycol-O, O'-bis(2-aminoethyl)-N, N, N',N'-tetraacetic acid, NTA (Nitrilotriacetic acid), HEDTA (N-(2-Hydroxyethyl)-ethylenediamine-N,N',N'-triacetic acid), DTPA (2-[Bis[2-[bis(carboxymethyl)amino]-ethyl]amino]acetic acid), or DOTA (1,4,7,10-tetraazacyclo-dodecane-1,4,7,10-tetraacetic acid).

For example, the linker may be covalently coupled to a cytotoxin, which may e.g. also be referred to as "payload" (see e.g. Perez et al. Drug Discovery Today Vol 19 (7), July 2014). Cytotoxins which are e.g. suited for covalent attachment to linker molecules may be grouped into two main classes: The first class includes cytotoxins which disrupt microtubule assembly and the second class cytotoxins which target DNA structure. Accordingly, cytotoxins which may e.g. be covalently coupled to the linker as disclosed above include doxorubicin, calicheamicin, auristatin, maytansine duoarmycin and analogs thereof, α-amaitin, tubulysin and analogs thereof. Methods for covalently coupling or attaching cytotoxins to linkers are known in the art and may e.g. be done according to the method disclosed in Mol. Pharmaceutics 2015, 12, 1813-1835.

In one embodiment the at least one linker as disclosed above is covalently coupled to at least one Fab or scFv light chain (VL) of the inventive heterodimeric bispecific immunoglobulin molecule. Accordingly, at least one light chain, e.g. one or two light chains of the inventive heterodimeric bispecific immunoglobulin molecule may be coupled to a linker as disclosed above. For example, covalent coupling may be done by introducing, one or more, e.g. 2, 3, or 4, 5 or 6, additional cysteine residues into the scFv molecule, mainly at the C-terminus, which allow conjugation to sulfhydryl-reactive reagents as disclosed in e.g. Merty et al. Protein Expression and Purification 21, 156-164 (2001); Nataranja, A et al. Bioconjugate Chem. 16, 113-121; Krimner et al. Protein Eng., Des. Sel. 19, 461-470; Albrecht et al. Bioconjugate Chem. 15, 16-26). Cysteine residues can e.g. also be alkylated by reacting them with α-haloketones or Michael acceptors, such as maleimide derivates. Alternatively, the modification of lysine residues may e.g. be utilized which is the oldest of and most straightforward method for labeling proteins via the primary lysine amino groups. The s-amino group of lysine within the protein of interest can be readily reacted with activated esters, sulfonyl chlorides, isocyanates and isothiocyanates to result in the corresponding amides, sulfonamides, ureas and thioureas (see e.g. Takaoka et al., Angew. Chem. Int. Ed. 2013, 52, 4088-4106). Further examples for bioconjugation include the conjugation of fluorescent proteins, dyes, or the tethering with functional molecules, e.g. PEGs, porphyrins, peptides, peptide nucleic acids, and drugs (Takaoka et al., Angew. Chem. Int. Ed. 2013, 52, 4088-4106).

For example, enzyme-mediated conjugation may also be applied for covalently coupling the linker as disclosed above to the inventive heterodimeric bispecific immunoglobulin molecule. For example, WO 2014/001325 A1 discloses the use of sortase A for site-specific bioconjugation to Fc regions of an antibody. Sortase A (SrtA) is a bacterial integral membrane protein first described in *Staphylococcus aureus*. SrtA catalyzes a transpeptidation reaction anchoring proteins to the bacterial cell wall. Upon recognition of a sorting signal LPXTG, (X=D, E, A, N, Q, or K) (SEQ ID NO: 53) a catalytic cysteine cleaves the peptide bond between residues T and G which results in the formation of a thioacyl intermediate. This thioacyl intermediate subsequently then can reacts with an amino-terminal glycine acting as a nucleophile. SrtA accepts N-terminal (oligo) glycine as a nucleophiles, creating a new peptide bond between two molecules. SrtA functions at physiological conditions and has been used for bioconjugation reactions to label proteins with e.g. biotin, or to functionalize a HER2-specific recombinant Fab with the plant cytotoxin gelonin (see e.g. Popp et al. (2011) Angew Chemie Int. Ed. 50: 5024-5032; Kornberger et al (2014) mAbs 6 (2): 354-366). Typically, target proteins such as e.g. the VL and VH chains of the first and/or second Fab or scFv fragments as disclosed above, are labeled carboxyterminally with the LPXTG motif (SEQ ID NO: 54) followed by a purification tag such that the SrtA-mediated transpeptidation removes the purification tag and generates the labeled protein.

In one embodiment the heterodimeric bispecific immunoglobulin molecule according to the invention as disclosed above comprises two linkers covalently coupled to the Fab or scFv light chains of said heterodimeric bispecific immunoglobulin molecule. For example, the linkers may be coupled to the light chain of the VL chain of the first Fab or scFv fragment of the inventive the heterodimeric bispecific immunoglobulin molecule which specifically binds to EGFR as disclosed above and e.g. to the VL chain of the second Fab or scFv fragment of the inventive the heterodimeric bispecific immunoglobulin molecule which specifically binds to c-MET as disclosed above.

In one embodiment the Fab or scFv light chains and/or the CH3 domains and/or the CH2 domains of the heterodimeric bispecific immunoglobulin molecule of the invention as disclosed above are covalently coupled to a linker, whereby said linker is covalently coupled to a dye, radioisotope, or cytotoxin as disclosed above.

For example, the VL chains of the first and second Fab or scFv fragment may be covalently coupled to a linker as disclosed above, whereby the linker is further coupled to a dye radioisotope or cytotoxin as disclosed above, or both engineered CH3 domains of the inventive heterodimeric bispecific immunoglobulin molecule as disclosed above ("AG-SEED", "GA-SEED") may be covalently coupled to a linker as disclosed above, or e.g. the CH2 domains of the heterodimeric bispecific immunoglobulin molecule of the invention as disclosed above, may each be covalently coupled to a linker as disclosed above. Studies with anti-CD30 monoclonal antibody auristatin E (MMAE) conjugates have shown that ADCs with a antibody:drug stoichiometry of 1:2-1:4 are most effective, with a ratio of 1:4 being most preferable (see e.g. Hamblett et al. Clinical Cancer Research (2004) Vol. 10, 7063-7070). Thus, the inventive heterodimeric bispecific immunoglobulin molecule as disclosed above may e.g. comprises 2, 3, or 4 linker molecules which are covalently coupled to the inventive heterodimeric bispecific immunoglobulin molecule, whereby each linker is preferably coupled to a cytotoxin as disclosed above, e.g. the VL chains and the VH chains of the heterodimeric bispecific immunoglobulin molecule of the invention may be coupled to a cytotoxin via a linker as disclosed above. For example, the VH chains and the CH3 domains of the inventive heterodimeric bispecific immunoglobulin molecule as disclosed above may be covalently coupled to a linker, whereby each linker is further coupled to a cytotoxin. Alternatively, the VL chains of the first and second Fab or scFv fragment and the CH3 or CH2 domains of the inventive heterodimeric bispecific immunoglobulin molecule as disclosed above may be covalently coupled to a linker which is further coupled to a cytotoxin as disclosed above.

In one embodiment the heterodimeric bispecific immunoglobulin molecule according to the invention as disclosed above is for use in the treatment of cancer. The term "cancer" as used in the present invention refers to a variety of conditions caused by the abnormal, uncontrolled growth of cells, e.g. cells capable of causing cancer, referred to as "cancer cells", possess characteristic properties such as uncontrolled proliferation, immortality, metastatic potential, rapid growth and proliferation rate, and/or certain typical morphological features. Cancer cells may e.g. be in the form of a tumor, but such cells may also exist singly within a subject, or may be a non-tumorigenic cancer cell. The term cancer as used in the context of the inventive method of treatment may e.g. refer to prostate cancer, breast cancer, adrenal cancer, leukemia, lymphoma, myeloma, bone and connective tissue sarcoma, brain tumors, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinoma, lung cancer, testicular cancer, penal cancer, oral cancer, skin cancer, kidney cancers, Wilms' tumor and bladder cancer, metastatic (mCRC), non-resctable liver metastases, squamous cell carcinoma of the head and neck, non-small cell lung cancer (NSCLC), head and neck squamous cell carcinoma (HNSCC), Merkel cell carcinoma, In one embodiment the invention provides a composition which comprises the heterodimeric bispecific immunoglobulin molecule of the invention as disclosed above and at least one further ingredient. For example, the inventive composition may comprise the heterodimeric bispecific immunoglobulin molecule of the invention as disclosed above and one or more of water, buffer, stabilizer, salt, sugar, preservative (e.g. benzalkonium chloride), lipids, anti-oxidants, carboxylic acids, polyethylene glycol (PEG). For example, the buffer or buffer solution may have a pH from about 5 to about 9, e.g. from about pH 5 to about pH 6, or from about pH 6 to about pH 7, or from about pH 8 to about pH 9, or from about 5.1, 5.2, 5.3, 5.4, 5.5, 5.6, 5.7, 5.8, 5.9, 6.0, 6.1, 6.2, 6.3, 6.5, 6.6, 6.7, 6.8, 6.9, 7.0, 7.1, 7.2, 7.3, 7.4, 7.5, 7.6, 7.7, 7.8 to about 8.0, 8.1, 8.2, 8.3, 8.4, 8.5, 8.6, 8.7, 8.8, 8.9 and may e.g. comprise sodium acetate, histidine, citrate, succinate or phosphate buffers. For example, sodium acetate, histidine, citrate, succinate or phosphate may be present in the composition according to the invention in a concentration of from about 10 mM, 15 mM, 20 mM, 25 mM, 30 mM, 35 mM, 40 mM, 45 mM, 50 mM to about 60 mM, 70 mM, 80 mM, 90 mM, 100 mM, 125 mM, 150 mM. For example, the buffer solutions as disclosed above may be combined with a preservative such as benzalkonium chloride to stabilize the inventive heterodimeric bispecific immunoglobulin molecule as disclosed above. Other ingredients may e.g. include, polyethylene glycol with an average molecular weights of 200-4000 Dalton, e.g. 300, 400, 500, 600, 700, 800, 900, 1000, 1500, 1750, 2000, 2250, 2500, 3000, 3500 Dalton and its derivatives. Polyethylene glycol derivatives may e.g. also be used and may e.g. include polyethylene glycol monolaurate, polyethylene glycol mono-oleate and polyethylene glycol monopalmitate. For example, the composition according to the invention may comprise the inventive heterodimeric bispecific immunoglobulin molecule as disclosed above in aqueous or lyophilized form and at least one further chemotherapeutic agent, wherein the agent is selected from the group comprising capecitabine, 5-fluoro-2'-deoxyuiridine, irinotecan, 6-mercaptopurine (6-MP), cladribine, clofarabine, cytarabine, floxuridine, fludarabine, gemcitabine, hydroxyurea, methotrexate, bleomycin, paclitaxel, chlorambubil, mitoxantrone, camptothecin, topotecan, teniposide, colcemid, colchicine, pemetrexed, pentostatin, thioguanine; leucovorin, cisplatin, carboplatin, oxaliplatin, or a combination of 5-FU, leucovorin, a combination of 5-fluorouracil/folinic acid (5-FU/FA), a combination of 5-fluorouracil/folinic acid (5-FU/FA) and oxaliplatin (FLOX), a combination of 5-FU, leucovorin, oxaliplatin (FOLFOX), or a combination of 5-FU, leucovorin, and irinotecan (FOLFIRI), or a combination of leucovorin, 5-FU, oxaliplatin, and irinotecan (FOLFOXIRI), or a combination of Capecitabine and oxaliplatin (CapeOx).

In one embodiment the present invention provides a pharmaceutical composition which comprises the heterodimeric bispecific immunoglobulin molecule of the invention as disclosed above and at least one further ingredient, or which comprises the inventive composition as disclosed above. For example, the pharmaceutical composition of the invention may comprise the heterodimeric bispecific immunoglobulin molecule of the invention as disclosed above in a concentration from about 10 mg/ml, 20 mg/ml, 25 mg/ml, 30 mg/ml, 35 mg/ml, 40 mg/ml, 45 mg/ml, 50 mg/ml, 55 mg/ml, 60 mg/ml to about 70 mg/ml, 75 mg/ml, 80 mg/ml, 90 mg/ml, 100 mg/ml, 112 mg/ml, 125 mg/ml, 150 mg/ml, 175 mg/ml, 200 mg/ml, or e.g. from about 10 mg/ml to about 20 mg/ml, 25 mg/ml, 30 mg/ml, 35 mg/ml, 40 mg/ml, 45 mg/ml, 50 mg/ml, 55 mg/ml, 60 mg/ml to about 70 mg/ml, 75 mg/ml, 80 mg/ml, 90 mg/ml, 100 mg/ml, 112 mg/ml, 125 mg/ml, 150 mg/ml, 175 mg/ml, 200 mg/ml, or e.g. 20 mg/ml, 25 mg/ml, 30 mg/ml, 35 mg/ml, 40 mg/ml, 45 mg/ml, 50 mg/ml, 55 mg/ml, 60 mg/ml to about 70 mg/ml, 75 mg/ml, 80 mg/ml, 90 mg/ml, 100 mg/ml, 112 mg/ml, 125 mg/ml, 150 mg/ml, 175 mg/ml, 200 mg/ml and e.g. an aqueous buffer as disclosed above. The inventive pharmaceutical composition as disclosed above, may e.g. also comprise surfactants such e.g. anionic surfactants such as e.g. a mixture of sodium alkyl sulfates, cationic surfactants, such as e.g. quaternary ammonium and pyridinium cationic surfactants, or non-ionic surfactants, such as e.g. Sorbitan esters, polysorbates, e.g. Polysorbat 20 (Polyoxyethylen-(20)-sorbitanmonolaurat), Polysorbat 21 (Polyoxyethylen-(4)-sorbitanmonolaurat), Polysorbat 40 (Polyoxyethylen-(20)-sorbitanmonopalmitat), Polysorbat 60 (Polyoxyethylen-(20)-sorbitan-monostearat), Polysorbat 61 (Polyoxyethylen-(4)-sorbitanmonostearat), Polysorbat 65 (Polyoxyethylen-(20)-sorbitantristearat), Polysorbat 80 (Polyoxyethylen-(20)-sorbitanmonooleat), Polysorbat 81 (Polyoxyethylen-(5)-sorbitanmonooleat) Polysorbat 85 (Polyoxyethylen-(20)-sorbitantrioleat), Polysorbat 120 (Polyoxyethylen-(20)-sorbitan monoisostearat), or poloxamers e.g. poloxamer 105, poloxamer 108, poloxamer 122, poloxamer 124, poloxamer 105 benzoate. Preservatives which may be comprised in the pharmaceutical composition according to the invention may be benzalkonium chlorid in a concentration of 0.004% to 0.01%. For example, the inventive pharmaceutical composition may be formulated by use of conventional techniques as discrete dosage forms, such as capsules, a solution or a suspension in an aqueous liquid or a non-aqueous liquid; or as an oil-in-water liquid emulsion or a water-in-oil emulsion and as a bolus; together with suitable pharmaceutically acceptable carrier.

In one embodiment the pharmaceutical composition of the invention as disclosed above is for use in the treatment of cancer. For example, the inventive pharmaceutical composition as disclosed above for use in the treatment of cancer may be administered to a person inflicted with cancer.

In one embodiment the invention provides a method of treatment which comprises administering to a subject a therapeutically effective amount of the inventive pharmaceutical composition as disclosed above. For example, the inventive method of treatment may comprise administering a person in need thereof afflicted with cancer as disclosed above from about 0.001 mg/kg to about 50 mg/kg of the inventive pharmaceutical composition, or from about 0.005 mg/kg to about 45 mg/kg, or from about 0.01 mg/kg to about 40 mg/kg, or from about 0.05 mg/kg to about 35 mg/kg, or from about 0.1 mg/kg, 0.5 mg/kg, 0.75 mg/kg, 1 mg/kg, 1.5 mg/kg, 2 mg/kg, 2.5 mg/kg, 3 mg/kg, 4 mg/kg, 5 mg/kg, 6 mg/kg 7 mg/kg, 8 mg/kg, 9 mg/kg, 10 mg/kg, 12.5 mg/kg, 15 mg/kg, 17.5 mg/kg, 20 mg/kg, 22.5 mg/kg, 25 mg/kg to about 26 mg/kg, 27 mg/kg, 28 mg/kg, 29 mg/kg, 30 mg/kg, 32.5 mg/kg, 35 mg/kg, 37.5 mg/kg, 40 mg/kg, 42.5 mg/kg, 45 mg/kg. As used the term "mg/kg" refers to mg of the inventive pharmaceutical composition/kg body weight in the present invention. For example, a pharmaceutically effective amount of the inventive pharmaceutical composition may be administered to an individual inflicted with cancer. The pharmaceutically effective amount depends on the individual, the type of cancer to be treated, the body weight and age of the individual, the level of the disease or the administration route.

EXAMPLES

Example 1: Generation of Anti c-Met and Anti-EGFR Binders

Generation of c-MET Binders

Panning of naïve phage display antibody gene libraries HAL7/8 against human c-MET was performed according to Hust and colleagues. 36;37 Briefly, after pre-selection with panning buffer (1% skim milk powder, 1% BSA, 0.05% Tween® 20 in PBS) in maxisorp 96 well plates (Nunc), scFv displaying phages were selected on 1 µg immobilized c-MET-Fc (R&D Systems, 358-MT/CF) or c-MET SEMA domain (produced in house) and eluted with trypsin. After two to three rounds of panning, c-MET specific binders were enriched and screened by capture c-MET ELISA of produced scFv.

For affinity maturation, (a) error prone PCR for variable domains was performed using the GeneMorph II Random Mutagenesis Kits (Agilent Technologies) according to the manufacturer's instruction, (b) randomization of complementary-determining region three of the heavy chain (CDR-H3) ordered by GeneArt applying a parsimonious mutagenesis strategy 70, and (c) light chain shuffling using the diversity of the HAL7/8 were conducted. Panning was carried out using phage display and yeast display for F06 and B10, respectively. For clone F06, an off-rate screening strategy was applied by stringent washing (ten times) with 100 µl panning buffer per well as well as adding soluble c-MET for competition (starting in the second round). CS06 was based on rational combination of abundant mutations from approach (a) and (b). B10v5 was derived from approach (c) using yeast surface display as described in e.g. Biotechnol. Bioeng. 2009; 103: 1192-201; Protein Eng Des Sel 2010; 23: 155-9.

Generation of Anti-EGFR Binders

The structure of C225 bound to the extracellular domain of EGFR 42 was optimized with the Rosetta Protein Structure and Design program (version 2.3.0) using a fixed backbone protocol and side chain optimization to minimize the energy of the starting model for design according to the Rosetta energy function. Interfacial water molecules observed in the crystal structure were retained during the minimization, but not during subsequent design calculations. Thirty-seven residues at or near the antibody-antigen interface were selected for a saturating, in silico point mutagenesis. At each of these residues 19 variants were created (wild type and 18 mutations, no cysteine) optimizing the rotamer of the mutated residue while keeping the backbone fixed. Using these preliminary models, neighbour residues were identified as any residue with at least 3 heavy atoms within 5.5 Å of a heavy atom on the design residue. The rotamer of the mutated residue and its neighbours were optimized using the standard Rosetta score function (a linear combination of terms including a Lennard-Jones potential, an orientation-dependent hydrogen bonding potential, an implicit solvation model and statistical terms that capture backbone-dependent amino acid and rotamer preferences. The hydrophobic substitutions will be described elsewhere. The polar substitutions were filtered to only those variants with improvements of at least 0.5 Rosetta energy units in either the orientation-dependent hydrogen bonding score or the pair potential relative to the repacked native to select improved variants. The three affinity enhancing point substitutions were combined into a triple mutant, and this was repacked and scored by Rosetta as described above for the point mutants. The affinity of the selected variants was measured in vitro by surface plasmon resonance. The variants were also transferred to the hu225 scFv and the affinities in this context were verified by biolayer interferometry.

Example 2: Expression and Purification of Bispecific c-MET×EGFR SEEDbodies

Several combinations of EGFR and c-MET antibody fragments according to the invention as disclosed herein were joined to bispecific antibodies using the SEED-technology.

Bispecific c-MET×EGFR SEEDbodies were expressed by transient transfection of Expi293F™ cells (human embryonic kidney cells) according to the manufacturer's instruction of the transfection kit (Invitrogen). Briefly, suspension Expi293F™ cells were cultured in Expi293F™ expression medium (Invitrogen) at 37° C., 5% $CO_2$ and 180 rpm. On the day of the transfection, cells were seeded in fresh medium with a density of final $2\times10^6$ viable cells/ml. DNA-Expi-Fectamine™293 reagent mixture diluted in Opti-MEM® I medium (Invitrogen) was added to the cells. 16 h post transfection, ExpiFectamine™293 transfection enhancer 1 and 2 were added. Cell supernatants containing secreted antibodies were harvested 5 days after transfection by centrifugation at 4,300×g, 4° C. and 20 min and filtration through 0.22 µm Stericup or Steriflip devices (Millipore). Small scale productions were performed in a volume of 25 ml and purification was carried out with PROSEP® A centrifugal Protein A columns (Millipore, #P36486) according to manufacturers' instructions followed by dialysis to PBS pH 7.4 using Pur-A-Lyzer™ Dialysis Kit (Sigma-Aldrich).

Large scale productions were performed in an expression volume of 200 ml. Supernatants were purified by affinity chromatography (5 ml HiTrap MabSelect SuRe, GE Healthcare) on an AKTA Explorer 100 (GE Healthcare) with subsequent preparative size exclusion chromatography (HiLoad 26/60Superdex 200 µg, GE Healthcare). Protein concentrations were determined by UV A280 spectroscopy and purity was analyzed by gel electrophoresis with 4%/8% NuPAGE BisTris gels (Life technologies) and coomassie staining as well as analytical size exclusion high performance liquid chromatography (TSK Super SW3000, Tosoh). Endotoxin levels were assessed by Limulus amebocyte lysate Endosafe® PTS cartridges and Endosafe® PTS reader (Charles River).

Antibody VH and VL sequences for humanized oa 5D5 (MetMAb, onartuzumab), LY2875358 (LA480_vC8H241, emibetuzumab), and h224G11 (ABT-700) were derived from publicly available information (e.g. U.S. Pat. No. 6,214,344B1, U.S. Pat. No. 8,398,974 B2, U.S. Pat. No. 0,273,060A1). Sequences were cloned in mammalian expression vectors containing constant IgG1 light and heavy chain fragments except in case of oa 5D5 knob-into-hole technology was applied (e.g. as disclosed in Protein Eng 1996; 9: 617-21). All anti-c-MET reference antibodies as well as cetuximab (C225, Erbitux) and matuzumab were produced in-house (Merck) in HEK293E cells using standard transfection and purification procedure e.g. as described above.

Example 3: Binding of Bispecific c-MET×EGFR Antibodies to c-MET and EGFR on Cells Bispecific c-MET×EGFR antibodies, one-armed (monovalent) control antibodies (anti-c-MET and anti-EGFR) as well as a non-related isotype control (anti-hen egg lysozyme, anti-HEL) were tested for their binding to c-MET and EGFR expressing NCI-H441 cells (as e.g. shown in FIG. 1, FIG. 15). NCI-H441 cells were detached with trypsin, centrifuged at 250×g for 10 min at 4° C. and resuspended in FACS buffer (1% BSA in 1×PBS). Cells were transferred to in 96 well round bottom plates at a density of 1×10$^5$ cells/well on ice. Purified c-MET×EGFR bispecific antibodies (0.02-200 nM) were added in FACS buffer in triplicates for 1 h on ice. Cells were centrifuged for 1000×g for 5 min at 4° C. and washed 3 times with 100 µl FACS buffer. Cells were incubated with 500 ng/well Fluorescein (FITC)-conjugated goat anti-human Fc gamma fragment IgG specific antibody (Jackson ImmunoResearch) diluted in FACS buffer on ice for 1 h. Cells were washed again 3 times with 100 µl FACS buffer. For counter staining of non-viable cells, centrifuged cells were resuspended in 200 µl propidium iodide solution (Invitrogen) diluted in FACS buffer (1:200). Cell were analyzed for fluorescence at 488 nm using a Guava easyCyte HT cytometer (Millipore). Data were plotted as mean fluorescence intensity (raw fluorescence subtracted by background, e.g. non-stained cell control) against the logarithm of the bispecific antibody concentration and fitted to a sigmoidal dose-response curve with variable slope using GraphPad Prism 4 (GraphPad Software).

Example 4: Epitope Binning of c-MET Binders Using Bio-Layer Interferometry (BLI)

Figure 2:
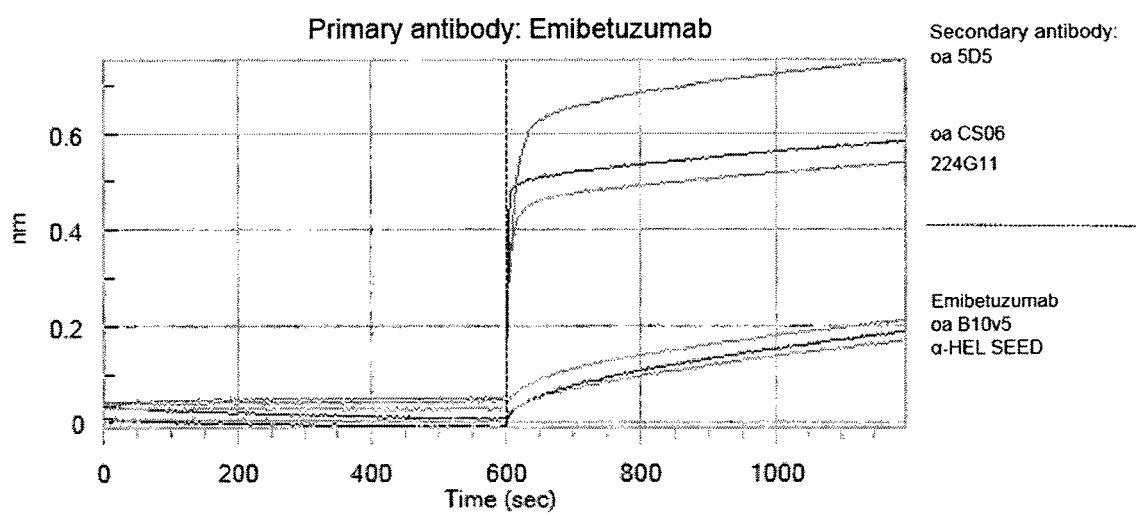
FIG. 2: (A) Epitope binning results, (B) Biosensor experiments using bio-layer interferometry (cf. Example 3).

An epitope binning experiment was carried out with c-MET antibodies which were used in the bispecific antibodies and compared to reference antibodies from the literature (MetMAb, Emibetuzumab, h224G11). Biosensor experiments using bio-layer interferometry were performed on an Octet Red platform (Forté Bio) equipped with anti-human Fc (AHC) biosensor tips (Forté Bio). All data were collected at 30° C. in kinetics buffer (PBS pH 7.4, 0.1% BSA, 0.02% Tween-20. Human c-MET ECD-His (HGFR, hepatocyte growth factor receptor extracellular domain) was produced and purified in-house. Biosensor tips were equilibrated 30 sec in PBS. Then, 25 nM for bivalent IgGs and 50 nM for monovalent one-armed antibodies in PBS were immobilized on biosensor tips for 200 sec as primary antibody. Tips were quenched with 400 nM of a non-related control antibody (anti-hen egg lysozyme, anti-HEL SEED, diluted in PBS) to minimize subsequent binding of secondary antibodies to biosensor tips. Following acquisition of a baseline in kinetics buffer for 60 sec, human c-MET-ECD was subjected to immobilized primary antibodies for 600 sec. Afterwards, interactions of secondary anti-c-MET antibodies to c-MET-ECD bound to immobilized primary antibodies was analyzed for 600 sec. Analysis of secondary antibody binding was analyzed visually by distinguishing simultaneous binding characterized by a higher binding rate [nM] compared to a non-related isotype control (anti-HEL SEED). The results of the epitope binning are depicted in FIG. 2A.

Figure 3:
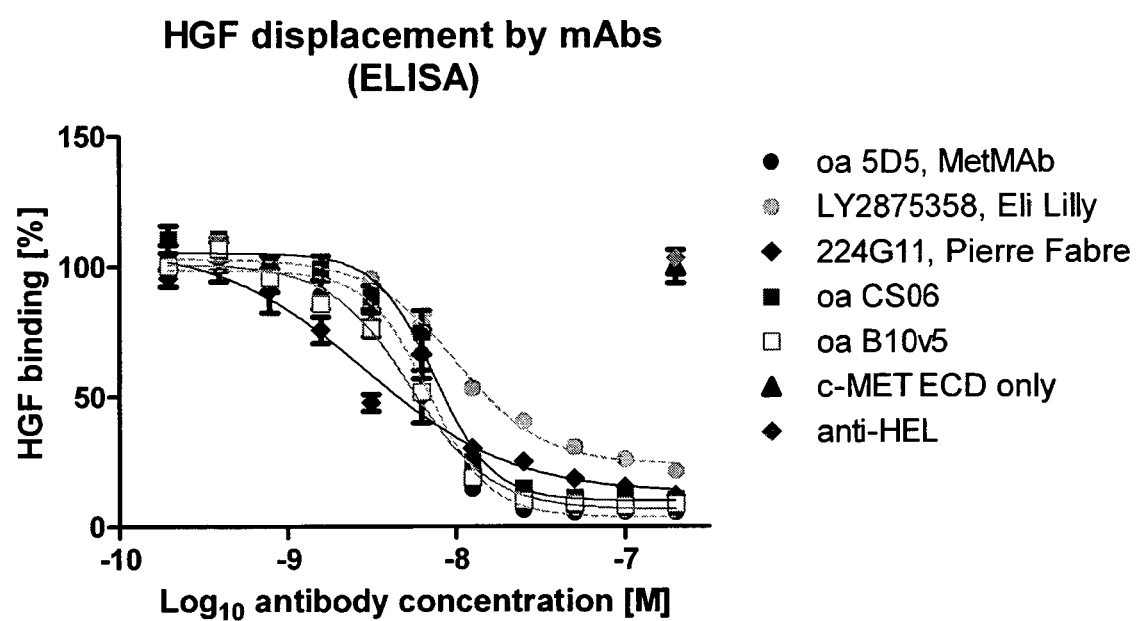
FIG. 3: HGF displacement results.
Figure 4:
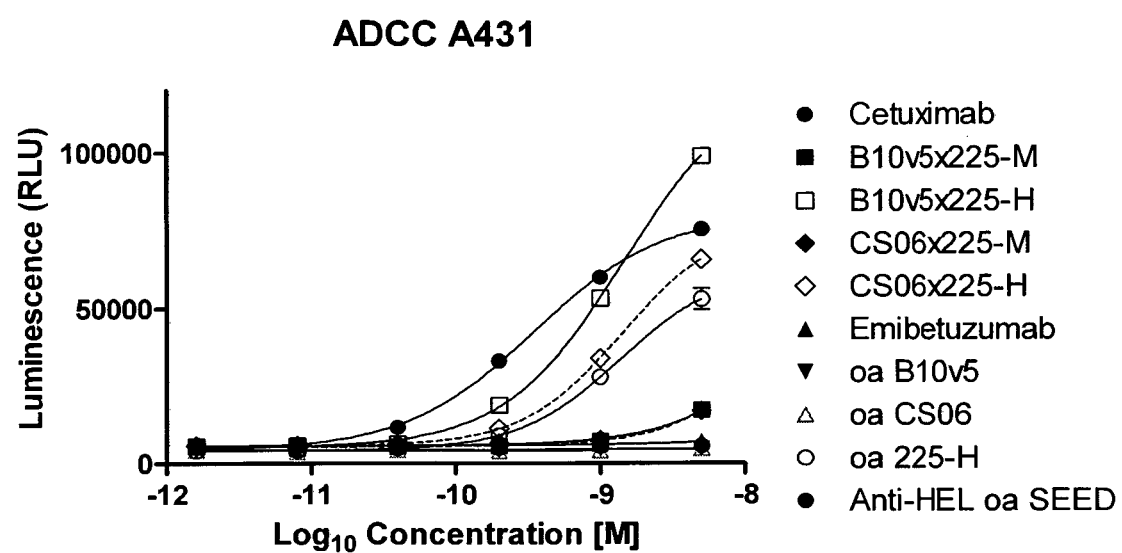
FIG. 4: ADCC experiments on A431 cells using the antibodies as indicated.
Figure 5:
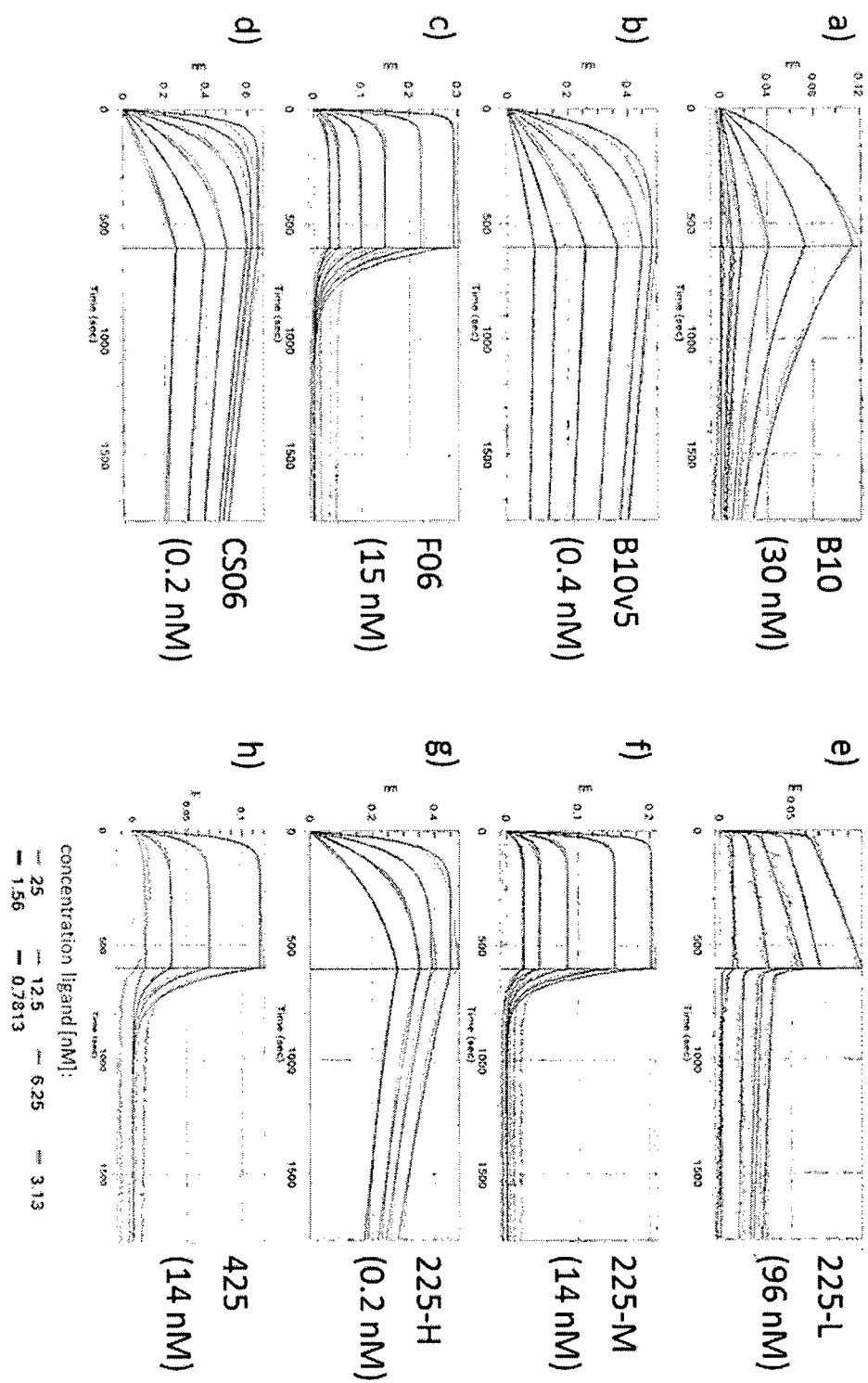
FIG. 5: Octet analysis of one-armed heterodimeric immunoglobulin molecule variants (either Fab or scFv). "225-L", "225-H", "225-H" denote kinetic variants of humanized cetuximab (hu225), "425" denotes Matuzumab.
Figure 13:
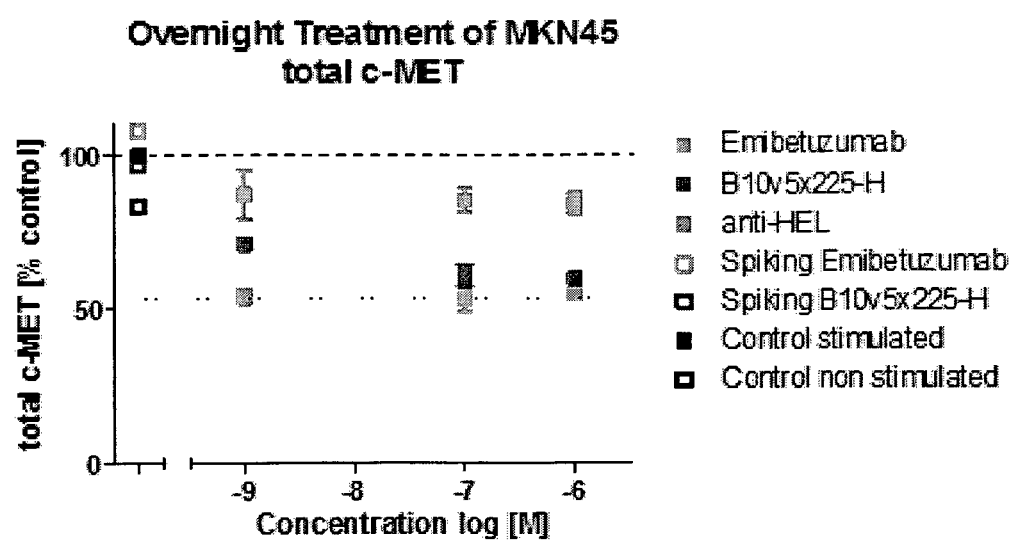
FIG. 13: Enhanced degradation of c-MET following overnight treatment with the inventive B10v5x225-H molecule.
Figure 14:
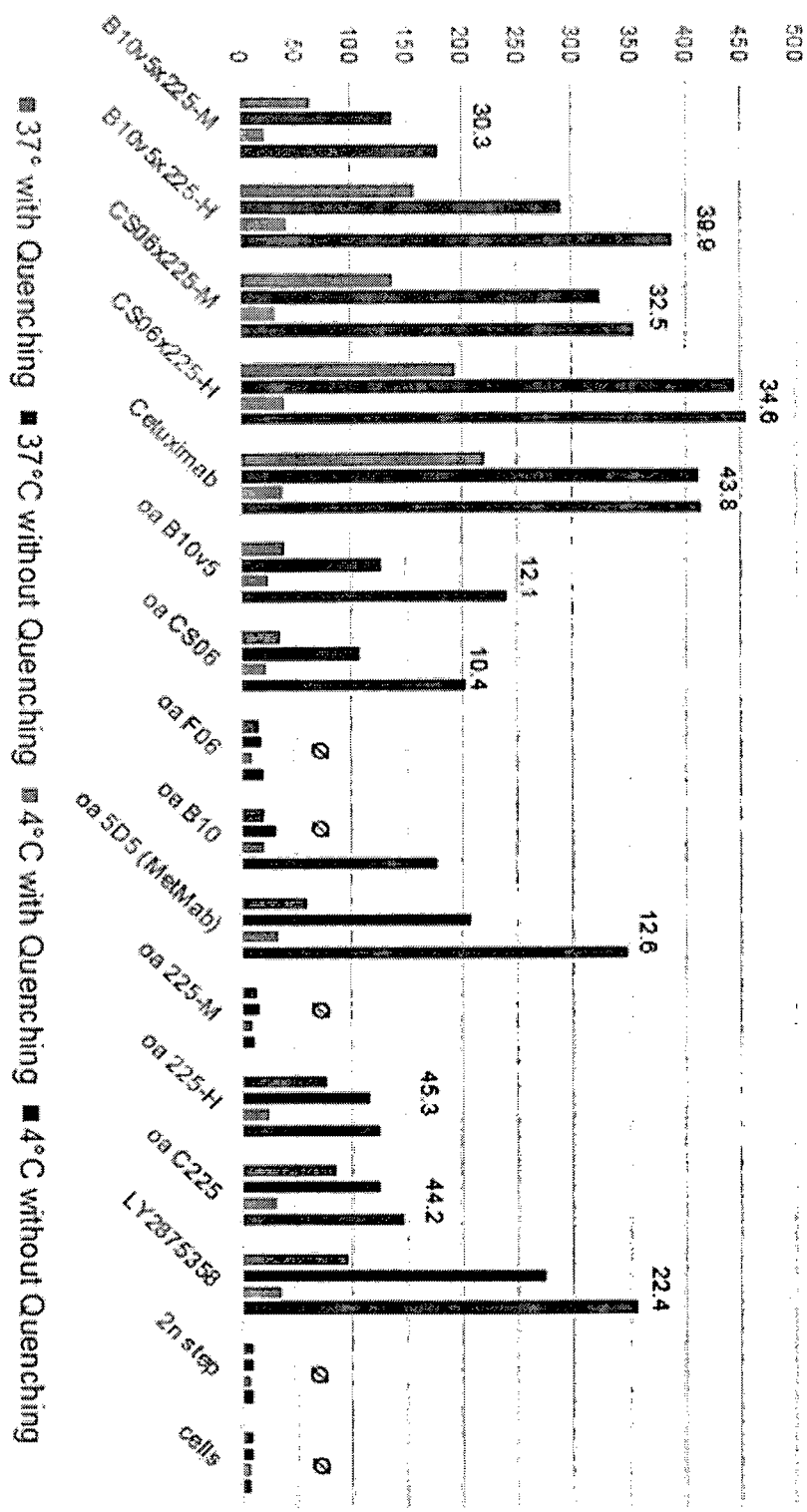
FIG. 14: Internalization assay on NCI-H441 cells using the antibodies and controls as indicated to assess the suitability of individual constructs for their use as ADC.

Example 5: HGF Competition ELISA Assay/HGF Displacement by Monoclonal Antibodies Competition of recombinant human HGF (Hepatocyte growth factor, R&D Systems, 294-HGN/CF) with antibody binding to recombinant human c-MET ECD (HGFR extracellular domain, Hepatocyte growth factor receptor) was detected by ELISA using HGF in solid phase. Recombinant human HGF (1.255 pmol) was immobilized on 96 well Maxisorp plates (Thermo Scientific) overnight at 4° C. After blocking plates with 2% BSA, biotinylated recombinant human c-MET ECD (1.13 pmol) pre-incubated with serial dilutions of antibodies (200 nM to 0.2 nM) were added to plates. Binding was revealed using HRP-conjugated strepatvidin (Merck Millipore) and TMB substrate and sulfuric acid (1 step Ultra TMB ELISA solution). Resulting absorbance for c-MET ECD binding to HGF without addition of anti-c-MET directed antibody was defined as 100% HGF binding. Anti-HEL (hen egg lysozyme) was used as an unrelated isotype control antibody. Data were plotted as % HGF binding against the logarithm of the antibody concentration and fitted to a sigmoidal dose-response curve with variable slope using GraphPad Prism 4 (GraphPad Software). The results of the displacement are depicted in FIG. 3.

Example 6: Cell Titer Glow Assay

Cell viability was quantified using the cell titer glow assay (Promega) and was performed according to the manufacturer's instructions. Briefly, cells were detached and seeded in the inner wells of opaque white tissue culture treated 96 well plates (Perkin&Elmer). The seeding cell number ranged from 8,000 to 15,000 viable cells per well depending on the cell line in 80 µl per well. Cells were allowed to attach at least three hours in a humidified chamber at 37° C., 5% CO2. Then, cells were treated with antibodies in duplicates which were diluted in cell line specific medium (ranging from 60 to 0.01 nM final). Depending on the assay, Fab-toxin conjugates were added in a threefold molar excess (Fab-toxin from Moradec, MMAE or DMSA). After 72 hours, viability of cells was detected by adding 100 µl per well of CellTiter-Glo® reagent (Promega) with subsequent mixing on a plate shaker for two minutes at 350 rpm and 10 min incubation in the dark at room temperature. Luminescence was measured at a Synergy 5 (Biotek) with a read time of 0.5 seconds per well (sensitivity: 170). Background luminescence in wells with only medium with the CellTiter-Glo® reagent (Promega) was subtracted. Data were plotted as percentage of untreated cell viability against the logarithm of antibody concentration and fitted to a sigmoidal dose-response curve with variable slope using GraphPad Prism 4 (GraphPad Software).

Example 7: ADC Generation and Antibody Dependent Cellular Cytotoxicity

ADC Generation

Sortase mediated site-directed conjugation of valine-citrulline (vc)-monomethyl auristatin E (MMAE) to antibody Fc was performed as described elsewhere (see e.g. ACS Chem. Biol. 2015; 10: 2158-65). Briefly, antibodies or the inventive heterodimeric bispecific immunoglobulin molecules carrying enzyme recognition site C-terminally on both heavy chains were generated, transfected and purified by affinity chromatography. Then, one equivalent of antibody was incubated with 11 equivalents of substrate-vc-MMAE conjugate in the presence of 5 µM Sortase and 5 mM CaCl$_2$) in reaction buffer (50 mM Tris, 150 mM NaCl, pH 7.5) for 30 min at 22° C. The reaction was stopped with 10 mM EDTA as calcium ion chelator. The resulting ADC was purified by size exclusion chromatography.

Antibody Dependent Cellular Cytotoxicity.

Capability of the antibodies to induce ADCC was assessed using the ADCC Reporter Bioassay Core Kit (Promega) according to the manufacturer's instruction. Briefly, target cells (A431 cells) were detached and seeded into the inner wells of opaque white tissue culture treated 96 well plates (Perkin&Elmer) with a cell density of 12.500 viable cells per well (100 µl). A431 cells were cultured in ADCC buffer containing RPMI 1640 medium (Gibco) supplement with 4% low IgG fetal bovine serum (FBS, Gibco). Cells were allowed to attach overnight in a humidified chamber at 37° C., 5% CO2. The next day, medium was removed and cells were treated with 25 µl antibodies per well diluted in ADCC buffer (final concentrations ranging from 5 to 0.0016 nM). Afterwards, recombinant Jurkat cells (Promega) were added which function as effector cells (360 µl effector cells diluted in 3.6 ml ADCC buffer, 25 µl per well). After six hours of incubation in a humidified chamber at 37° C., 5% CO2, 75 µl of Bio Glo Luciferase Substrate (Promega), which was equilibrated at room temperature, was added per well. After ten minutes of incubation at room temperature protected from light, luminescence was measured at a Synergy 5 (Biotek) with a read time of 0.5 seconds per well (sensitivity: 170). Background luminescence in wells with only medium was subtracted. Relative luminescence units were plotted against the logarithm of antibody concentration and fitted to a sigmoidal dose-response curve with variable slope using GraphPad Prism 4 (GraphPad Software).

Example 8: Receptor Phosphorylation Assay

Figure 20:
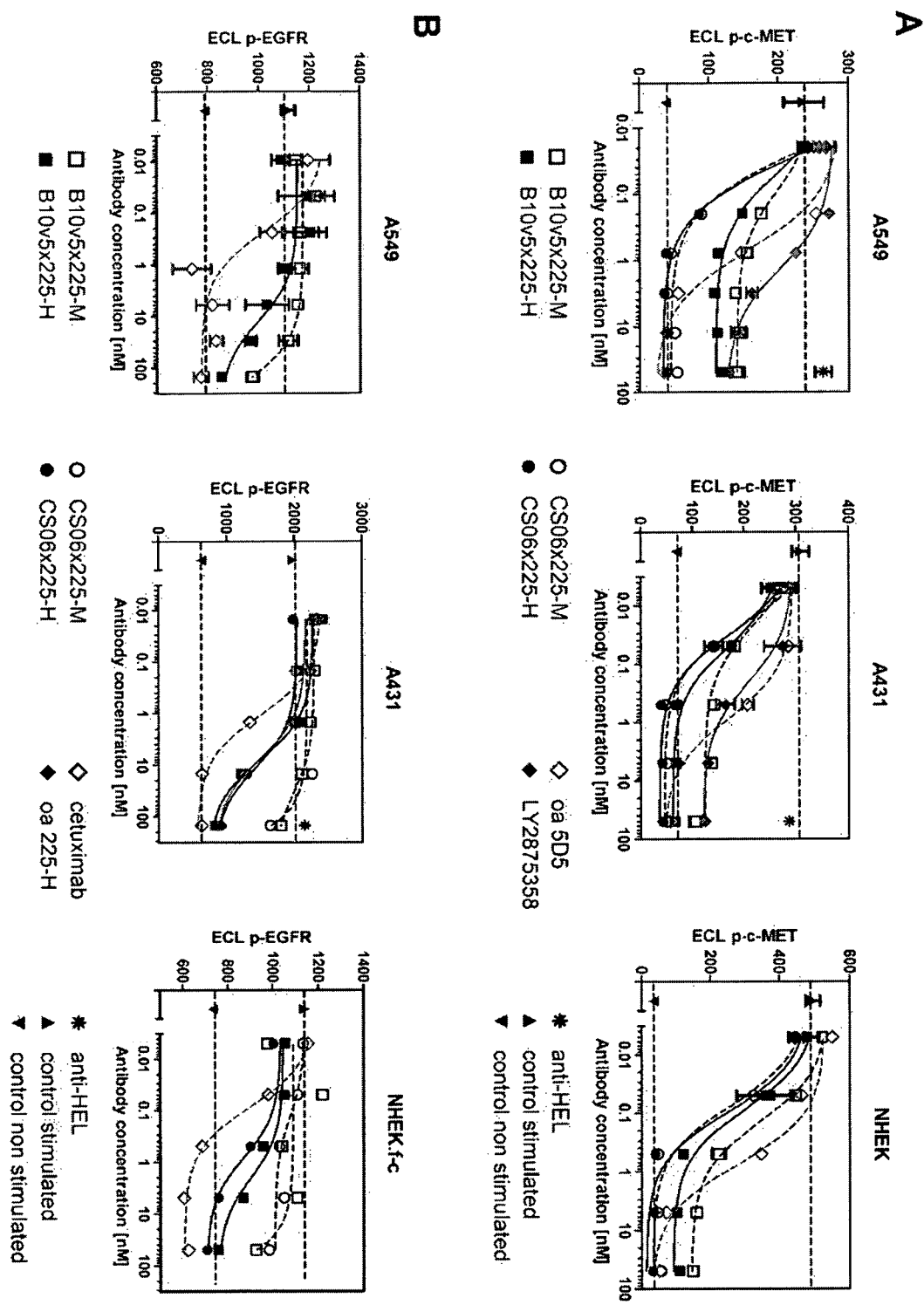
FIG. 20: Inhibition of c-MET and EGFR phosphorylation by c-METxEGFR bsAbs during ligand stimulation. Phosphorylated c-MET (A) and phosphorylated EGFR (B) were quantified in A549, A431 and primary keratinocytes (NHEK) using electrochemiluminescence assay (ECL). Cells were treated with varying concentrations of bsAbs and a non-related isotype SEED control with subsequent stimulation with 100 ng/ml HGF (A) or 100 ng/ml EGF (B). Triangles indicate respective receptor phosphorylation levels for stimulated (upwards triangle) and non-stimulated cells (downwards triangle). Dose response curves were fitted using a 3PL model in GraphPad Prism 5 (GraphPad Software, Inc).
Figure 21:
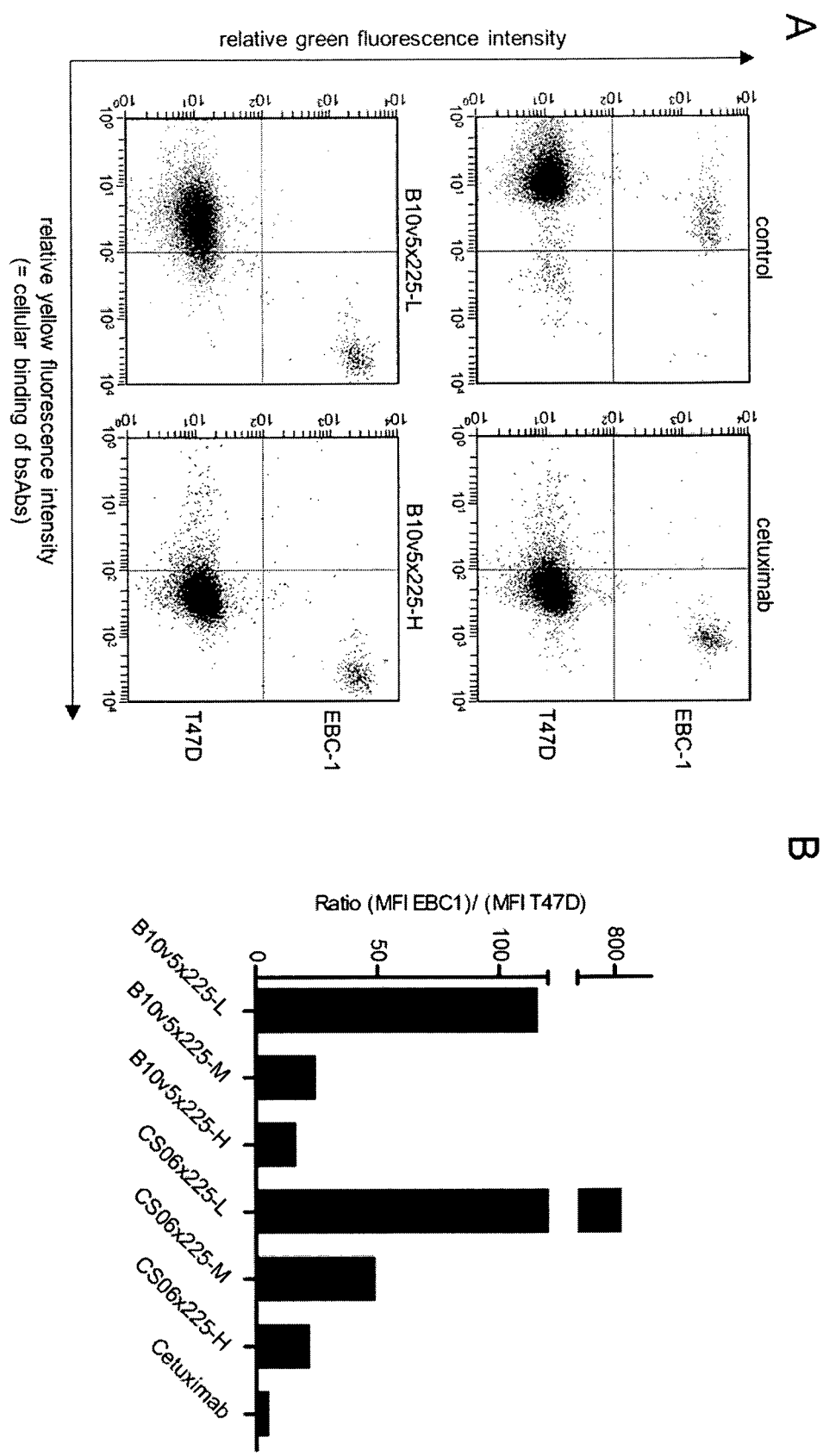
FIG. 21: In vitro selectivity of c-METxEGFR bsAbs in comparison to cetuximab. (A) EBC-1 as tumor model cell line with high to moderate c-MET and EGFR expression and T47D as epithelial model cell line with low EGFR expression and no c-MET expression were mixed in a ratio of 1:30. In order to distinguish the two cell lines, EBC-1 cells were stained with the green membrane dye PKH2. The cell mixture was incubated with 300 nM of bsAb and cetuximab and subjected to flow cytometric analysis. Antibody binding was detected by FITC-labeled anti-hu Fc secondary antibody. Representative dot plots for green vs. yellow fluorescence are shown. (B) In vitro selectivity was defined as the ratio of mean fluorescence intensity of the EBC-1 and the T47D cell population.
Figure 22:
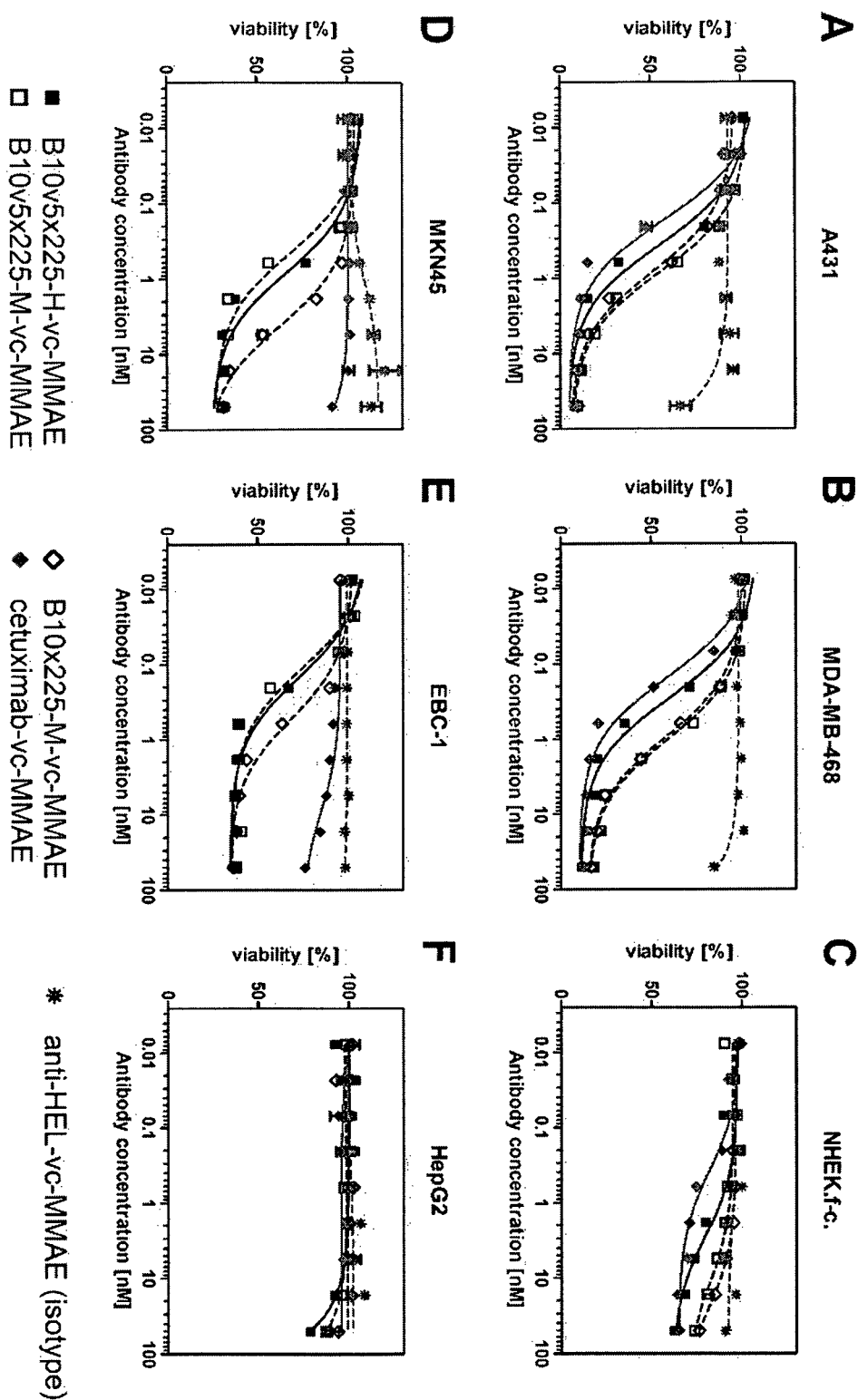
FIG. 22: Cytotoxicity of c-METxEGFR bispecific SEED antibody-drug conjugates generated by covalent, site-directed conjugation of the tubulin inhibitor MMAE C-terminally to both heavy chains in comparison to cetuximab as ADC and anti-hen egg lysozyme (HEL) ADC as corresponding reference constructs. Cytotoxicity was assessed on EGFR overexpressing tumor cells A431 (A) and MDA-MB-468 (B), on primary keratinocytes (NHEK.f-c., C) as normal epithelial cell line, on c-MET overexpressing cells MKN45 (D) and EBC-1 (E) as well as HepG2 (F) as liver cell line. Assay was run in duplicates in three independent experiments and curves were fitted by sigmoidal curve fitting using GraphPad Prism 5 (GraphPad Software, Inc).
Figure 24:
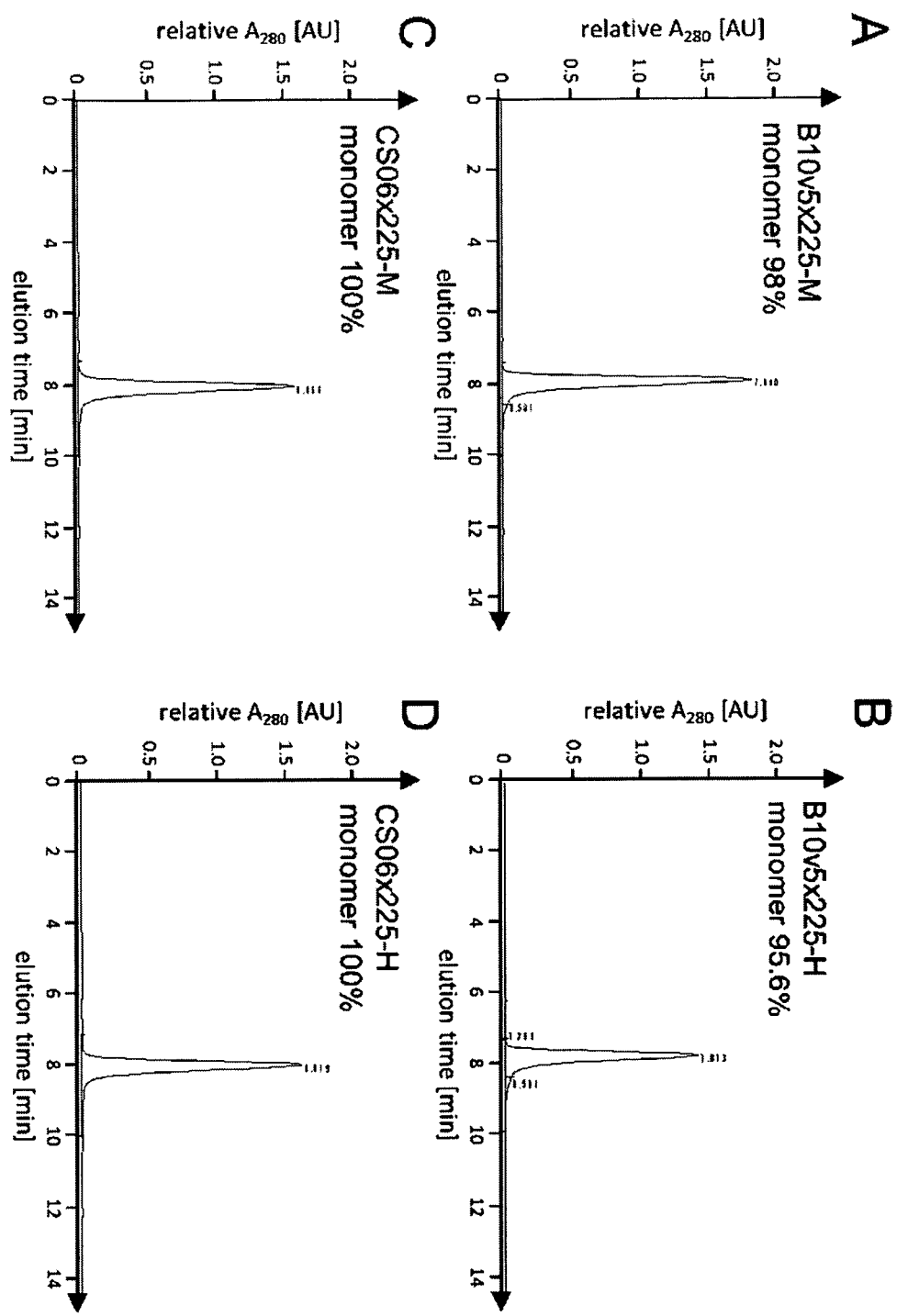
FIG. 24: Analytical SE-HPLC indicates a purity >95% of four exemplary bispecific antibodies (bsAb) following purification: (A) B10v5x225-M, (B) B10v5x225-H, (C) CS06x225-M and (D) CS06x225-H.
Figure 26:
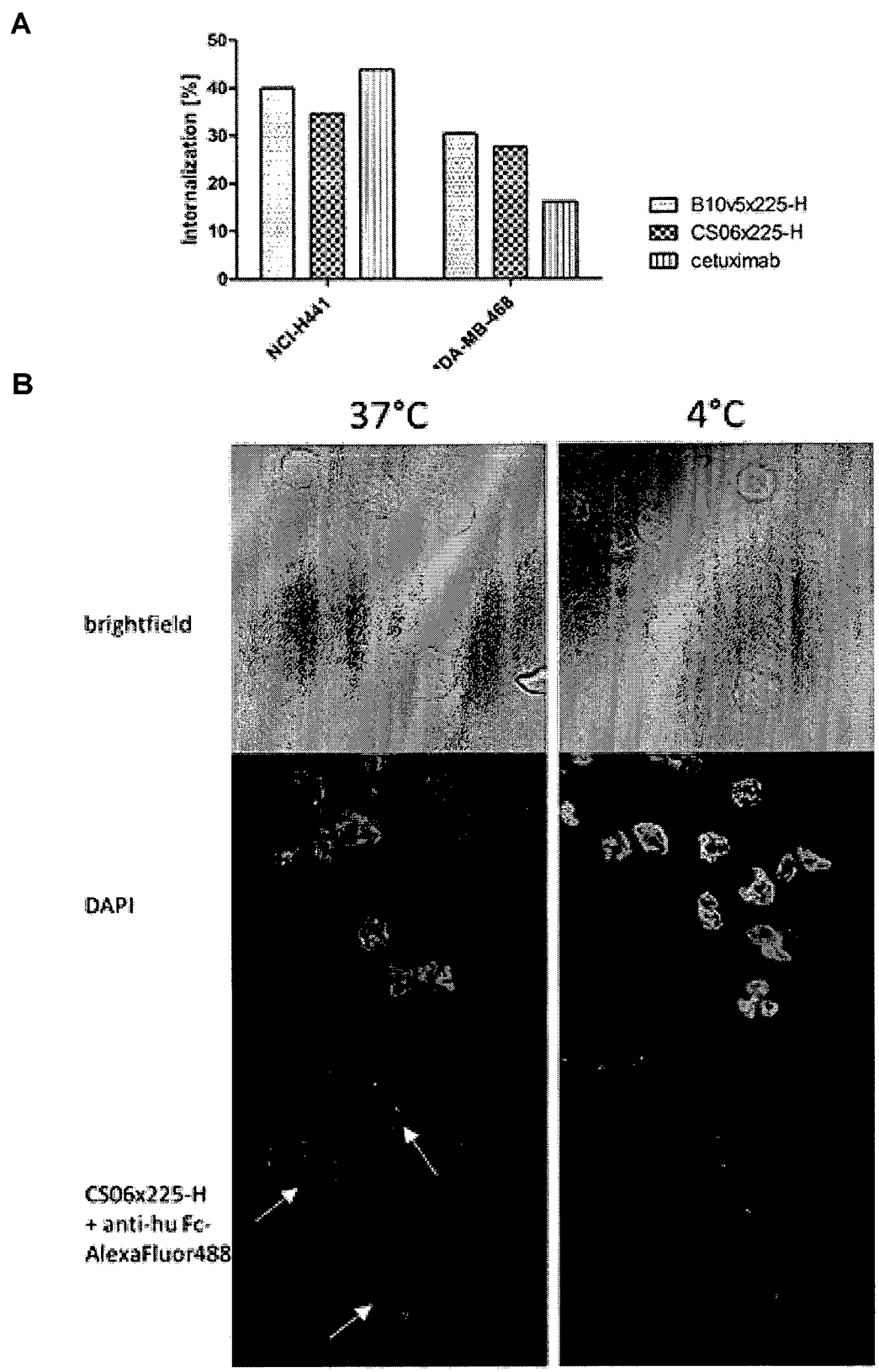
FIG. 26: Internalization of bispecific antibodies (bsAbs) as determined by flow cytometry and confocal fluorescence microscopy. (A) Internalization was quantified by flow cytometric analysis employing 100 nM bsAbs which were detected with anti-human Fc-AlexaFluor488 conjugate at 37° C. for 1 h in comparison to cells incubated at 4° C. Residual cell surface binding was quenched by anti-AlexaFluor488 antibody. (B) EBC-1 cells were incubated with 100 nM CS06x225-H and detected with anti-human Fc-AlexaFluor488 conjugate at 37° C. or 4° C. Surface staining was removed by acidic wash.
Figure 27:
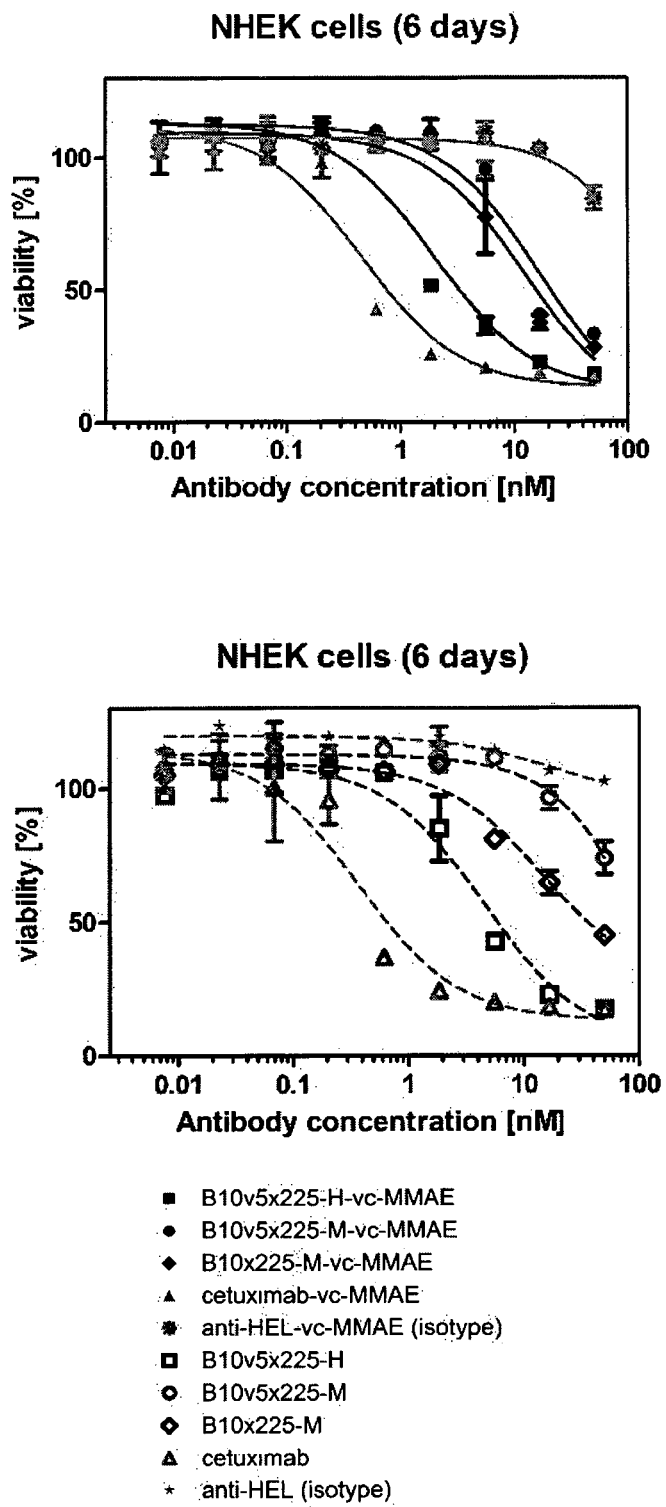
FIG. 27: Cytotoxicity of bispecific ADCs and bsAb on NHEK after 6 days. Primary keratinocytes (NHEK) were incubated with varying concentrations of bispecific ADC or alternatively with bsAbs for 6 days, in order to exclude that the slow division rate of keratinocytes in comparison to tumor cells influenced cytotoxicity of the tubulin inhibitor MMAE. Curves were plotted using 3PL fitting in GraphPad Prism 5 (GraphPad Software, Inc.).

To assess the effect of binding of the inventive heterodimeric bispecific immunoglobulin molecules on c-MET and EGFR-mediated signaling phosphorylation levels of both c-MET and EGFR were determined by c-MET or EGFR capture electrochemiluminescence (ECL) ELISA (MSD assay). All reagents were obtained from Meso Scale Discovery and prepared according to the manufacturer's instructions. Briefly, cells were plated in 96-well tissue culture plates (Sigma-Aldrich) one day before treatment, serum starved and treated with serially diluted antibodies (0-167 nM in starvation medium) for 1 h at 37° C., 5% CO$_2$. Upon stimulation with either 100 ng/ml HGF and/or EGF (both R&D Systems) for 5 min at 37° C., cells were lysed with ice-cold lysis buffer supplemented with protease and phosphatase inhibitors (Calbiochem). High bind 96-well plates including electrodes (Meso Scale Discovery) were coated with capture anti-total c-MET (Cell Signaling Technologies) or anti-total EGFR antibodies (Abcam) followed by blocking with 3% Block A in PBS supplemented with 0.05% Tween® 20. After incubation with cell lysates, detection was carried out with anti-phospho c-MET (Cell Signaling Technologies), anti-phospho-tyrosine antibodies (R&D Systems) and by the supplier recommended detection substances. Measurements were performed with the SECTOR® Imager 6000 (Meso Scale Discovery). For quantification of phospho-AKT levels, the Phospho(Ser473)/Total AKT Assay Whole Cell Lyate Kit (Meso Scale Discovery) was used. Dose response curves were plotted as the logarithm of antibody concentration versus ECL signal. IC$_{50}$ values were calculated by a 3PL fitting model using GraphPad Prism 5 (GraphPad Software, Inc.). Data from at least two experiments were used to calculate mean IC$_{50}$±standard deviation (s.d.), see e.g. FIG. 20, FIG. 25 (A).

Example 9: Quantification of Cell Surface Receptor Density

Receptor surface expression levels on selected cell lines were determined using the QFIKIT (Dako K0078) employing flow cytometry, the results of which are shown in FIG. 18. Briefly, five populations of calibration beads presenting different numbers of mouse mAb molecules on their surfaces were used as a calibration standard. 1.5×105 cells/well were labeled with primary mouse anti-EGFR (ab187287, Abcam) and mouse anti-c-MET antibodies (MAB3582, R&D Systems) at saturating doses (5 µg/ml). Then, beads and cells were stained with secondary goat anti-mouse Fc F(ab')2 FITC conjugate (10 µg/ml, Jackson Immuno Research) and were subjected to flow cytometry measurement using a Guava easyCyte HT cytometer (Millipore). Beads and cells were measured on the same day using the same settings. Based on a calibration line for fluorescence of beads versus bead surface density, antigen cell surface densities for c-MET and EGFR were calculated.

Example 10: Internailzation Assay

Internalization of the inventive heterodimeric bispecific immunoglobulin molecules was either determined by flow cytometry using an anti-Alexa Fluor 488 quenching antibody or by confocal microscopy applying pH stripping. For flow cytometry, cells (1×105) were incubated with 100 nM bsAbs followed by Alexa Fluor 488 conjugated anti human Fc (Fcγ specific, Jackson Immuno Research). After washing with FACS buffer, cells were incubated at either 37° C. or 4° C. for 1 h allowing internalization. Afterwards, residual surface binding of bsAb was quenched by anti-Alexa Fluor 488 IgG (Life Technologies) and cells were fixated with 4% (w/v) formaldehyde (Calbiochem) and subjected to flow cytometric analysis. Internalization was calculated as following:

$$rel.interalization\ [\%] = \frac{(37°\ C.\ with\ quench) - (4°\ C.\ with\ quench)}{(37°\ C.\ without\ quench) \times 100}$$

For fluorescence microscopy, cells (3×10$^5$) were grown on glass coverslips (Menzel Glaser) placed in 6 well plates. Two days later, cells were kept on ice and treated with 100 nM bsAbs followed by detection with Alexa Fluor 488 conjugated anti human Fc Fab fragment. After washing with 1% BSA in PBS, cells were incubated in respective medium at either 37° C. or 4° C. for 1 h allowing internalization. By addition of ice-cold low pH buffer (50 mM glycine, 150 mM NaCl, pH 2.7 adjusted with HCl), residual bsAbs on the cell surface were removed. Finally, cells were fixated with 4% (w/v) formaldehyde and mounted on object slides with ProLong Diamond Antifade Mountant with DAPI (Life Technologies). Analysis was carried out with a Leica TCS SPS confocal microscope equipped with a 100× objective (Leica Microsystems).

Example 11: Cell Culture

Human cancer cell lines which were used according to the present invention were obtained from the American Type Culture Collection (A431, A549, MDA-MB-468, NCI-H1975, NCI-H441, NCI-H596), the Riken Bioresourse Center Cell Bank (EBC-1, KP-4), Lipha (HepG2), and German Collection of Microorganims and Cell Cultures (MKN45) and maintained according to standard culture conditions (37° C., 5% CO$_2$, 95% humidity) using recommended media formulations. A549 and A431 were cultivated in Dulbecco's Modified Eagle's Medium (DMEM, Life Technologies) containing 10% Fetal Bovine Serum (FBS, Life Technologies). MDA-MB-468, NCI-H1975, HepG2, and MKN45 were maintained in RPMI-1640 (Life Technologies) supplemented with 10% FBS, 2 mM L-glutamine and 1 mM sodium pyruvate (both Life Technologies). NCI-H441, NCI-H596 were cultivated in RPMI-1640 with 10% FBS, 2 mM L-glutamine, 1 mM sodium pyruvate, 2.5 g/L D(+)-glucose (Sigma-Aldrich) and 10 mM HEPES (Life Technologies). KP-4 cells were cultivated in DMEM/F-12 with 10% FBS. EBC-1 cells were maintained in Minimal Essential Medium (MEM) with 10% FBS and 2 mM L-glutamine. NHEK.f.-c. (PromoCell, #C-12007) were obtained from PromoCell and propagated in recommended keratinocyte growth medium with supplements (PromoCell, #C-20111) and with the DetachKit (PromoCell, #C-41210) for cell detachment. Expi293F™ cells were purchased from Life Technologies and cultivated in corresponding Expi293 expression medium. All cell lines were shown to be sterile, certified *mycoplasma*-free, and never exceeded passage 20.

Example 12: Surface Plasmon Resonance

Affinity and kinetic parameters of in silico designed C225 variants was verified by surface plasmon resonance. Computationally guided substitutions were introduced into the wild-type C225 using the QuikChangeII kit (Stratagene) with mutagenic primers. The variant antibodies were expressed in HEK-293-6E cells. Cleared supernatant was purified by affinity chromatography using protein A. The antibody concentration was determined by absorbance at 280 nm, and the purity was verified by SDS-PAGE analysis. Surface plasmon resonance was performed on a Biacore A-100 (GE Healthcare). CM5 chips were coupled with goat anti-human IgG antibody (Jackson ImmunoResearch, Inc., 109-005-098) and used to capture the wild-type C225 or designed variants. Human EGFR (extracellular domain, R&D Systems, 1095-ER) was used as analyte. The affinity was determined by titrating the analyte from 0 to 40 nM and determining kinetic rate constants using the BiaEvaluation software to fit the association and dissociation phases using a 1:1 Langmuir binding model. The KD was determined as the ratio of the kinetic constants.

Example 13: Thermal Shift Assay

Thermal stability of the inventive heterodimeric bispecific immunoglobulin molecules, as well as of controls (C225 (cetuximab), matuzumab and "one-armed" (oa) constructs) was measured using a StepOnePlus Real-Time PCR System (Life Technologies) according to the manufacturer's instructions, the results of which are shown in FIG. 17 and the corresponding description. Briefly, 1 µM protein was mixed with a 20 fold excess of SYPRO Orange (Life Technologies) in PBS pH 7.4. Melting curves were recorded from 25° C. to 99° C. with an increment of 1° C.160 s. Data were analyzed with the Protein Thermal Shift™ Software (Life technologies) by calculating the maximum of the second derivative curve.

The invention claimed is:

1. A heterodimeric bispecific immunoglobulin molecule, comprising:
    a first Fab or scFv fragment which specifically binds to EGFR,
    a second Fab or scFv fragment which specifically binds to c-MET, and
    an antibody hinge region, an antibody CH2 domain and an antibody CH3 domain comprising a hybrid protein-protein interaction interface domain wherein each of said interaction interface domain is formed by an amino acid segment of the CH3 domain of a first member and an amino acid segment of the CH3 domain of a second member,
    wherein said protein-protein interface domain of the first chain is interacting with the protein-protein-interface of the second chain by homodimerization of a corresponding amino acid segment of the same member of an immunoglobulin superfamily within said interaction domains,
    wherein a first or second engineered immunoglobulin chain has a polypeptide sequence ("AG-SEED"):
    GQPFRPEVHLLPPSREEMTKNQVSLTCLARGFYPX$_1$ DIAVEWESNGQPENNYKTTPSR QEPSQGTT TFAV-TSKLTX$_2$DKSRWQQGNVFSCSVMHEALHNHYTQKX$_3$ ISL (SEQ ID NO:1), wherein X$_1$, X$_2$ and X$_3$ may be any amino acid, wherein the first Fab or scFv fragment comprises
a VL sequence selected from the group consisting of SEQ ID NO: 9, SEQ ID NO:10, SEQ ID NO: 44, and SEQ ID NO: 46; and
a VH sequence selected from the group consisting of SEQ ID NO: 11, SEQ ID NO: 12, SEQ ID NO: 43, SEQ ID NO: 45;
wherein second Fab or scFv fragment comprises
a VL sequence selected from the group consisting of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 47, SEQ ID NO: 49, and SEQ ID NO: 51; and
a VH sequence selected from the group consisting of SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 48, SEQ ID NO: 50, and SEQ ID NO: 52.

2. The heterodimeric bispecific immunoglobulin molecule according to claim 1, wherein
a first member of the immunoglobulin super family is IgG and a second member is IgA.

3. The heterodimeric bispecific immunoglobulin molecule according to claim 2, wherein
$X_1$ is K or S,
$X_2$ is V or T, and
$X_3$ is T or S (SEQ ID NO: 2).

4. The heterodimeric bispecific immunoglobulin molecule according to claim 1, wherein
the first or second engineered immunoglobulin chain has the polypeptide sequence ("GA-SEED"):
GQPREPQVYTLPPPSEELALNEX1VTLTCLVKGFYPSDIAVEWLQGSQELPRE
KYLTWX2PVX3DSD
GSX4FLYSILRVX5AX6DWKKGDTFSCSVMHEALHNHYTQKSLDR, wherein $X_1$,
$X_2$, $X_3$, $X_4$, $X_5$ and $X_6$ may be any amino acid (SEQ ID NO: 3).

5. The heterodimeric bispecific immunoglobulin molecule according to claim 4, wherein
$X_1$ is L or Q,
$X_2$ is A or T,
$X_3$ is L, V, D or T;
$X_4$ is F, A, D, E, G, H, K, N, P, Q, R, S or T;
$X_5$ is A or T, and
$X_6$ is E or D (SEQ ID NO: 4).

6. The heterodimeric bispecific immunoglobulin molecule according to claim 1, wherein
the first engineered immunoglobulin chain has the polypeptide sequence ("AG-SEED"):
GQPFRPEVHLLPPSREEMTKNQVSLTCLARGFYPKDIAVEWESNGQPENNYKTTPSR QEPSQGTT TFAVTSKLTVDKSRWQQGNVFSCSVMHEALHNHYTQKTISL (SEQ ID NO: 5) and the second engineered immunoglobulin chain has the polypeptide sequence ("GA-SEED"):
GQPREPQVYTLPPPSEELALNELVTLTCLVKGFYPSDIAVEWLQGSQELPREKYLTW APVLDSDG SFFLYSILRVAAEDWKKGDTFSCSVMHEALHNHYTQKSLDR (SEQ ID NO: 6).

7. The heterodimeric bispecific immunoglobulin molecule according to claim 1, wherein
the first engineered immunoglobulin chain comprises the polypeptide sequence ("AG-SEED"):
GQPFEPEVHTLPPSREEMTKNQVSLTCLVRGFYPSDIAVEWESNGQPENNYKT TPSRLEPSQGTT TFAVTSKLTVDKSRWQQGNVFSCSVMHEALHNHYTQKSLSL (SEQ ID NO: 7) and the second engineered immunoglobulin chain comprises the polypeptide sequence ("GA-SEED"):
GQPREPQVYTLPPPSEELALNNQVTLTCLVKGFYPSDIAVEWESNGQPEPREK YLTWAPVLDSDG SFFLYSILRVDASRWQQGNVFSCSVMHEALHNHYTQKSLSL (SEQ ID NO: 8).

8. The heterodimeric bispecific immunoglobulin molecule according to claim 1, wherein
the first Fab fragment binds EGFR with an $K_D$ of at least $5 \times 10^{-8}$M.

9. The heterodimeric bispecific immunoglobulin molecule according to claim 1, wherein
the second Fab fragment binds c-MET with an $K_D$ of at least $5 \times 10^{-8}$ M.

10. The heterodimeric bispecific immunoglobulin molecule according to claim 9, wherein
the first Fab or scFv fragment is derived from cetuximab (C225).

11. The heterodimeric bispecific immunoglobulin molecule according to claim 1, wherein
the first and second Fab or scFv fragments comprise at least one amino acid sequence selected from the group consisting of SEQ ID NO: 9, SEQ ID NO: 43, SEQ ID NO: 17, SEQ ID NO:18, or SEQ ID NO: 47, SEQ ID NO: 48(225 L, B10), or (225M, B10v5) SEQ ID NO: 11, SEQ ID NO: 44, SEQ ID NO: 31, SEQ ID NO: 51, SEQ ID NO:32, or (225H, F06) SEQ ID NO:45, SEQ ID NO: 46, SEQ ID NO: 29, SEQ ID NO: 49, SEQ ID NO: 30, SEQ ID NO: 50, or (225H, CS06) SEQ ID NO: 45, SEQ ID NO: 46, SEQ ID NO: 33, SEQ ID NO: 34, SEQ ID NO: 52, or (225M, CS06) SEQ ID NO: 11, SEQ ID NO: 44, SEQ ID NO: 33, SEQ ID NO: 34, and SEQ ID NO: 52.

12. The heterodimeric bispecific immunoglobulin molecule according to claim 11, wherein
the first and second Fab or scFv fragments comprise amino acid sequences (225M, CS06) SEQ ID NO: 11, SEQ ID NO: 44, SEQ ID NO: 33, SEQ ID NO: 34, SEQ ID NO: 52, or (225H, CS06) SEQ ID NO:45, SEQ ID NO: 46, SEQ ID NO: 29, SEQ ID NO: 49, SEQ ID NO: 30, or SEQ ID NO: 50.

13. The heterodimeric bispecific immunoglobulin molecule according to claim 1, wherein
a Fc domain interacts with FcRn.

14. The heterodimeric bispecific immunoglobulin molecule according to claim 1, wherein
an amino acid which interacts with FcRn is derived from human IgG1.

15. The heterodimeric bispecific immunoglobulin molecule according to claim 1, wherein
the bispecific immunoglobulin mediates antibody-dependent cellular cytotoxicity.

16. A method for producing a heterodimeric bispecific immunoglobulin molecule according to claim 1, the method comprising:
culturing at least one host cell under conditions sufficient for heterologous expression of said heterodimeric bispecific immunoglobulin molecule, and
purifying said heterodimeric bispecific immunoglobulin molecule, wherein
said host cell comprises at least one polynucleotide which encodes at least one amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO:17, SEQ ID NO: 18, SEQ ID NO: 19, SEQ ID NO:20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO:40, SEQ ID NO: 41, SEQ ID NO:42, SEQ ID NO:43, SEQ ID NO:44, SEQ ID NO:45, SEQ ID NO:46, SEQ ID NO: 47, SEQ ID NO: 48, SEQ ID NO: 49, SEQ ID NO: 50, SEQ ID NO:51, and SEQ ID NO: 52.

17. A heterodimeric bispecific immunoglobulin molecule obtainable by a method according to claim 16.

18. The heterodimeric bispecific immunoglobulin molecule according to claim 1, wherein
said heterodimeric bispecific immunoglobulin molecule is covalently coupled to at least one linker.

19. The heterodimeric bispecific immunoglobulin molecule according to claim 18, wherein
the linker of said heterodimeric bispecific immunoglobulin molecule is coupled to a dye, radioisotope, or cytotoxin.

20. The heterodimeric bispecific immunoglobulin molecule according to claim 19, wherein
the at least one linker is covalently coupled to at least one of the Fab or scFv light chains of said heterodimeric bispecific immunoglobulin molecule.

21. The heterodimeric bispecific immunoglobulin molecule according to claim 20, wherein
said heterodimeric bispecific immunoglobulin molecule comprises two linkers covalently coupled to the Fab or scFv light chains of said heterodimeric bispecific immunoglobulin molecule.

22. The heterodimeric bispecific immunoglobulin molecule according to claim 21, wherein
the Fab or scFv light chains and/or the CH3 domains and/or the CH2 domains are covalently coupled to a linker,
wherein said linker is covalently coupled to a dye, radioisotope, or cytotoxin.

23. A method of treating cancer, the method comprising:
administering, to a subject in need thereof, the heterodimeric bispecific immunoglobulin molecule according to claim 1.

24. The method according to claim 23, wherein
the cancer is at least one cancer selected from the group consisting of prostate cancer, breast cancer, adrenal cancer, leukemia, lymphoma, myeloma, bone and connective tissue sarcoma, a brain tumor, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinoma, lung cancer, testicular cancer, penal cancer, oral cancer, skin cancer, kidney cancers, Wilms' tumor and bladder cancer, metastatic (mCRC), non-resectable liver metastases, squamous cell carcinoma of the head and neck, non-small cell lung cancer (NSCLC), and head and neck squamous cell carcinoma (HNSCC).

25. A composition, comprising:
the heterodimeric bispecific immunoglobulin molecule according to claim 1; and
at least one further ingredient.

26. The composition according to claim 25, which is a pharmaceutical composition.

27. A method of treating a subject in need thereof inflicted with cancer, the method comprising:
administering to said subject a therapeutically effective amount of the pharmaceutical composition according to claim 26.

28. A method of treating cancer, the method comprising:
administering, to a subject in need thereof, the heterodimeric bispecific immunoglobulin molecule according to claim 19.

* * * * *